(12) United States Patent
Patel et al.

(10) Patent No.: US 10,451,595 B2
(45) Date of Patent: Oct. 22, 2019

(54) INDICATING DEVICES BASED ON LATERAL DIFFUSION OF A MOBILE PHASE THROUGH A NON-POROUS STATIONARY PHASE

(71) Applicant: JP LABORATORIES, INC, Middlesex, NJ (US)

(72) Inventors: Gordhanbhai N Patel, Somerset, NJ (US); Julia Koleda, Linden, NJ (US)

(73) Assignee: JP LABORATORIES, INC, Middlesex, NJ (US)

( * ) Notice: Subject to any disclaimer, the term of this patent is extended or adjusted under 35 U.S.C. 154(b) by 84 days.

(21) Appl. No.: 15/113,953

(22) PCT Filed: Jan. 22, 2015

(86) PCT No.: PCT/US2015/012396
§ 371 (c)(1),
(2) Date: Jul. 25, 2016

(87) PCT Pub. No.: WO2015/112679
PCT Pub. Date: Jul. 30, 2015

(65) Prior Publication Data
US 2016/0349224 A1    Dec. 1, 2016

Related U.S. Application Data

(60) Provisional application No. 62/022,907, filed on Jul. 10, 2014, provisional application No. 61/932,107, filed on Jan. 27, 2014.

(51) Int. Cl.
*G01K 3/04* (2006.01)
*G04F 1/00* (2006.01)
*G07C 1/00* (2006.01)
*G01N 31/22* (2006.01)

(52) U.S. Cl.
CPC ............. *G01N 31/229* (2013.01); *G01K 3/04* (2013.01); *G04F 1/00* (2013.01); *G07C 1/00* (2013.01); *G01N 31/22* (2013.01)

(58) Field of Classification Search
CPC ........ G01N 31/229; G01N 31/22; G01K 3/04; G04F 1/00; G07C 1/00
USPC .................................. 116/206–207, 216–220
See application file for complete search history.

(56) References Cited

U.S. PATENT DOCUMENTS

| | | | | |
|---|---|---|---|---|
| 5,053,339 A | * | 10/1991 | Patel ........................ | G01K 3/04 116/206 |
| 5,158,363 A | * | 10/1992 | Speelman ................. | A61L 2/28 374/102 |
| 5,204,579 A | * | 4/1993 | Oshima ................. | C04B 35/111 313/143 |
| 5,602,804 A | * | 2/1997 | Haas ........................ | G01K 3/04 116/206 |

(Continued)

*Primary Examiner* — R. A. Smith
*Assistant Examiner* — Tania Courson
(74) *Attorney, Agent, or Firm* — Barbara B Maurer

(57) ABSTRACT

This invention relates to indicating devices, such as time-temperature indicators based on lateral diffusion of a vapor of a solid and/or liquid mobile phase (e.g., a sublimeable dye or an activator) through a non-porous stationary phase, such as a thin layer of a polymeric material. The lateral diffusion of the mobile phase creates a noticeable boundary in the stationary phase whose movement depends upon processes, such as time and temperature.

21 Claims, 22 Drawing Sheets

(a) Cross sectional view (b) Top View

(56) References Cited

U.S. PATENT DOCUMENTS

| | | | | |
|---|---|---|---|---|
| 5,622,137 A * | 4/1997 | Lupton, Jr. | G01K 11/16 | 116/217 |
| 5,633,836 A * | 5/1997 | Langer | B41M 3/005 | 116/200 |
| 6,435,128 B2 * | 8/2002 | Qiu | G01K 3/04 | 116/207 |
| 6,514,462 B1 * | 2/2003 | Simons | G01K 3/04 | 116/206 |
| 6,701,864 B2 * | 3/2004 | Watson, Jr. | G01N 31/22 | 116/206 |
| 6,741,523 B1 * | 5/2004 | Bommarito | G01K 3/04 | 116/220 |
| 7,063,041 B2 * | 6/2006 | Odashiro | G01K 1/02 | 116/217 |
| 7,430,982 B2 * | 10/2008 | Koivukunnas | G01K 3/04 | 116/207 |
| 7,434,535 B2 * | 10/2008 | Adamy | G01K 3/04 | 116/206 |
| 7,921,798 B2 * | 4/2011 | Kodama | G01N 31/225 | 116/206 |
| 8,056,498 B2 * | 11/2011 | Holt | G04F 1/00 | 116/206 |
| 8,166,906 B2 * | 5/2012 | Ambrozy | G01K 3/04 | 116/206 |
| 8,343,437 B2 * | 1/2013 | Patel | G01K 3/04 | 252/408.1 |
| 8,671,871 B2 * | 3/2014 | Huffman | G01K 3/04 | 116/207 |
| 9,448,182 B2 * | 9/2016 | Haarer | G01K 3/04 | |
| 9,744,742 B2 * | 8/2017 | Deng | G01K 3/04 | |
| 10,145,826 B2 * | 12/2018 | Haarer | G01N 31/229 | |
| 2005/0249899 A1 * | 11/2005 | Bonutti | B32B 27/00 | 428/35.2 |
| 2006/0032427 A1 * | 2/2006 | Ishii | B65D 79/02 | 116/217 |
| 2008/0025154 A1 * | 1/2008 | MacDonald | A61F 13/42 | 368/89 |
| 2012/0079981 A1 * | 4/2012 | Huffman | G01K 3/04 | 116/207 |

* cited by examiner (a) Cross sectional view
(b) Top View

INDICATING DEVICES BASED ON LATERAL DIFFUSION OF A MOBILE PHASE THROUGH A NON-POROUS STATIONARY PHASE

This application claims the benefit of U.S. Provisional Applications No. 61/932,102, filed Jan. 27, 2014 and No. 62/022,907 filed Jul. 10, 2014.

The present invention relates to an indicating device such as a time, temperature, time-temperature, food doneness, thaw and sterilization indicator based on lateral diffusion of a mobile phase through a non-porous stationary phase, such as a thin layer of a polymeric material. The lateral diffusion of the mobile phase creates a boundary whose movement depends upon processes, such as time and temperature.

BACKGROUND OF THE INVENTION

Perishable products have measurable shelf-lives, which are usually expressed within specified limits as the time left for available end use. The term "perishable(s)" or "perishable product(s)" is meant herein to include perishable foods, such as fresh, refrigerated, and frozen, vegetables, fruits, meats, fish, poultry, dairy products, bakery products, juices, pre-cooked foods, soft and alcoholic beverages, and also including nonfood items having shelf lives ranging from a few hours to several years including pharmaceuticals, vaccines, sera, blood, blood plasma, cosmetics, reactive chemical compounds, bio-chemicals, bio-products, and batteries which have a measurable shelf life.

Whenever a clock or timer is impractical or too expensive to use, color changing time indicators or indicating devices in forms of labels, stickers or badges are used. Indicators for monitoring the passage of a relative amount of time are referred herein to as time indicator (TI) or time indicating device including but not limited to visual validation of time, safety sticker, self-timing retail sticker, biological industrial process monitoring, self-expiring stickers to prevent re-use, employee ID and security ID labels, visitors badges, self-expiring parking tags, package and shipping labels, wrist bands, time indicating tickets for trains, buses, sport events, theaters etc., self-expiring passes for tours, emergency rooms, hospitals, museums, and other locations, event passes, security labels for screened luggage, purses, bags at airports to show the aircraft control people that the particular items were inspected, unmanned but video controlled entrances for visitors where the self-expiring visitor label issued electronically. It also includes limited use items for consumers where once opened or in use should be used within certain period, including but not limited to drinks, food items, health, personal and family care products.

Time-temperature indicator(s) (TTI) devices provide a way of indicating a cumulative exposure to time and temperature. A TTI device may be capable of indicating whether a commodity has been exposed to a temperature greater than a predetermined temperature for a period of time or to an integral value of time and temperature. For example, a TTI device might indicate exposure to an excessive temperature for an excessive period of time or both. A large number of time-temperature indicating devices and time indicating devices for monitoring thermal degradation of perishables and self-expiring labels, tickets and badges have been reported in patent literature. Many of these devices are based on diffusion of a chemical from one matrix to the other, sometimes through a permeable layer, to introduce a color change in the indicator layer. The other TTIs are based on chemical reactions, such as the solid state polymerization of diacetylenes, change in pH and change in photochromism and thermochromism.

A large number of patents have been issued for devices that monitor time and integral value of time and temperature.

Patel, in U.S. Pat. No. 5,053,339 discloses a color changing device for monitoring the time-temperature storage history, i.e. shelf life of perishable products. The device is composed of (1) an activator tape, containing an activator composition and matrix on a substrate, (2) an indicator tape, containing an indicating composition, matrix and (3) an optional permeable layer. The permeable layer is often referred to as a barrier layer. The device is activated by applying the activator tape over the indicator tape. This and similar devices in general are often referred herein to as two-tape devices, two-tape TTI and TI.

Haas and his co-inventors in a series of U.S. Pat. Nos. 4,903,254; 5,053,339; 5,446,705; 5,602,804; 5,633,835; 5,699,326; 5,715,215; 5,719,828; 5,785,354; 5,822,280; 5,862,101; 5,873,606; 5,930,206; 6,446,865; 6,452,873; 6,752,430; 7,139,226; and 7,263,037 have disclosed time monitoring devices and related processes. These devices are also based on diffusion of an activator (which also includes a dye) through a medium. The indicator has a matrix, e.g., an ink which has a binder.

The following patents are some other representative examples of TI and TTI devices: U.S. Pat. Nos. 2,896,568; 3,018,611; 3,046,786; 3,078,182; 3,311,084; 3,520,124; 3,921,318; 3,954,011; 3,962,920; 3,999,946; 4,154,107; 4,195,058; 4,212,153; 4,382,063; 4,404,922; 4,432,630; 4,432,656; 4,448,548; 4,480,749; 4,542,982; 4,573,711; 4,629,330; 4,643,122; 4,643,588; 4,646,066; 4,737,463; 4,779,120; 4,812,053; 4,846,095; 4,846,502; 4,917,503; 5,053,339; 5,058,088; 5,120,137; 5,293,648; 5,317,980; 5,364,132; 5,378,430; 5,446,705; 5,602,804; 5,633,836; 5,667,303; 5,699,326; 5,709,472; 5,715,215; 5,719,828; 5,785,354; 5,822,280; 5,862,101; 5,873,606; 5,930,206; 5,957,458; 5,974,003; 5,997,927; 6,042,264; 6,103,351; 6,214,623; 6,254,969; 6,514,462; 6,524,000; 6,536,370; 6,614,728; 6,752,430; 6,822,931; 6,916,116; 7,156,597; 7,157,048; 7,209,042; 7,280,441; 7,290,925 and 7,294,379.

Pre-cooked, ready-to-eat frozen foods are widely used today. The pre-cooked frozen food is heated either in a conventional oven (for example, heated with natural gas or electricity) or more conveniently in a microwave oven. A microwave oven does not heat the food uniformly. Some portions of food may not be done while the other portions may be over heated. Hence, there is a need for an indicating device that changes color when steam is emitted by the food.

There are a variety of threshold and defrost indicating devices reported in the literature, including those in the following patents: U.S. Pat. Nos. 3,233,459; 3,702,077; 3,786,777; 4,038,936; 4,114,443; 4,120,818; 4,144,834; 4,163,427; 4,280,361; 4,735,745; 4,892,677; 5,267,794; 5,685,641 and 5,695,284. This type of indicating devices undergo a color change with time and temperature when the product temperature undesirably exceeded above a predetermined temperature, e.g., about 0° C. These devices have not proven entirely satisfactory due either to deficiencies in their visual perceptual character or in the danger of their use, in their sensitivity to thawing conditions or in their complexity of manufacture or use. The shortcomings of such devices are that they often fail in practice.

A wide variety of medical supplies and other items are sterilized with materials and techniques, such as steam, dry heat, ethylene oxide, plasma, peracetic acid, formaldehyde and high-energy radiation. Kitchenware, such as dishes, cutlery, and utensils used at home and restaurants are also sterilized in dishwashers with hot water and hot air usually around 90° C. It is essential to assure that these items are sterilized or meet required specifications. A number of sterilization indicating devices, dosimeters and monitors are proposed in the literature. They include biological and chemical indicating devices. The color changing chemical indicating devices are inexpensive and are widely used.

A wide variety of foods especially canned foods, pharmaceuticals, hospital and medical supplies are sterilized. These and other products, such as linens are sterilized to kill living organisms to an acceptable level. Direct testing for sterility is destructive and expensive and hence indirect testing methods, such as color changing indicating devices are used.

Pressurized steam is used in hospitals to sterilize reusable medical equipment and supplies, such as gowns and linens. To differentiate between a tray containing sterilized goods and one containing non-sterile goods, which may not have been processed, an indicating device is used. The process of sterilization causes the device to change color. Often the original color is light, and the color after processing is dark. The change in color is caused by a chemical reaction in the ink. The indicating device may be in the form of a strip, card, or tape. By observation of the color of the sterilization indicating device, one can determine whether or not the package has been passed through the sterilization cycle.

Many steam sterilization indicating devices are reported in the literature and some of them are used for monitoring sterilization. A few of them use heavy and toxic metal compounds, such as those of lead or bismuth. For example, U.S. Pat. No. 3,523,011 describes an indicating device material consisting of calcium sulfide and lead carbonate. A number of patents are issued based on color changing sterilization indicating devices (e.g., those for steam, dry heat, ethylene oxide, plasma, peracetic acid, formaldehyde and high-energy radiation) using inorganic and organic compounds, including a variety of dyes and pigments. They include the following U.S. Patents: U.S. Pat. Nos. 2,798,885; 2,826,073; 3,098,751; 3,360,337; 3,360,338; 3,360,339; 3,386,807; 3,471,422; 3,568,627; 3,852,034; 3,862,824; 3,932,134; 3,981,683; 4,094,642; 4,121,714; 4,138,216; 4,195,055; 4,407,960; 4,410,493; 4,436,819; 4,486,387; 4,514,361; 4,576,795; 4,579,715; 4,596,696; 4,692,307; 4,678,640; 5,064,576; 5,087,659; 5,158,363; 5,200,147; 5,223,401; 5,252,484; 5,258,065; 5,451,372; 5,788,925; 5,801,010; 5,866,356; 5,916,816; 5,990,199; 6,063,631; 6,485,978; 6,589,479; 6,659,036; 6,800,124; 6,884,394; 7,141,214 and 7,189,355.

Many of the above mentioned devices are also based on vertical diffusion of a liquid or vapor through a permeable barrier which is usually very thin, typically less than 100 microns.

Thin layer chromatography (TLC) is a chromatography technique used for separation of a non-volatile mixture of compounds, often referred as analytes. Thin layer chromatography is performed on a substrate material, such as a sheet of glass, plastic, or aluminum foil, which is coated with a thin layer of adsorbent material, usually silica gel, aluminum oxide or cellulose. This layer of adsorbent and/or absorbent is known as the stationary phase (SP). After a sample of analytes has been applied on the plate, a solvent or solvent mixture, known as the mobile phase (MP) is drawn up the plate via capillary action or wicking. Because different analytes ascend the TLC plate at different rates, separation is achieved.

Moving boundary devices for monitoring variety processes such time-temperature and sterilization based essentially on principal of TLC are proposed. They include the following:

U.S. Pat. No. 3,479,877 discloses an indicator device for showing the length of time an environment has been at or above a predetermined temperature. A fusible tablet of temperature indicator substance enclosed by a protective rigid cap is positioned at one end of a wick which is attached to but spaced from a heat-conducting base sheet. When the predetermined temperature is reached, the indicator substance melts and flows along the wick, the distance of flow indicating the length of exposure time.

U.S. Pat. No. 3,981,683 discloses a sterility indicator comprising a backing strip of a dimensionally stable material e.g. aluminum foil having mounted thereon an organic compound containing oxygen or nitrogen in intimate contact with a wicking means and a cover strip bonded to the backing strip overlaying the organic compound and wicking means. The cover strip is a polymeric rate controlling film which permits water vapor to pass through at a rate sufficient to make the device operative at a temperature to be monitored U.S. Pat. No. 4,044,707 discloses a time-temperature indicator comprising: a fluid source and an interruptible wick in contact with said fluid source upon activation of said time-temperature indicator, said wick being interruptible through severance at a weakened area after activation of said indicator, and said fluid source containing an indicating substance which has a defined melting range and a set rate of migration along said wick when melted and after activation of said indicator U.S. Pat. No. 4,353,990 discloses a device for monitoring thermal energy input and displaying the relationship of the thermal energy input to a selected time/temperature relationship. The device employs an indicating material which, when melted, expands and flows into a narrow channel to provide an irreversible, visible indication of the thermal energy to which the device has been exposed.

U.S. Pat. No. 4,382,700 discloses an indicator comprising a material, as for example a mineral jelly, which is in contact with a wick, such as a paper strip, such that the mineral jelly diffuses into the paper in accordance with changes in ambient temperature over a period of time. The amount of diffusion is indicated by an apparent change in color of the paper and is analogous to a change in the useful characteristic of the perishable goods.

U.S. Pat. Nos. 4,195,055 and 4,195,057 describe a vapor-phase moving-boundary indicator which is useful for monitoring the time-temperature histories of perishable articles. The device functions by allowing a vapor to permeate through a porous substrate coated with an indicating solid which undergoes a color change upon contact with the vapor. As the vapor permeates through the substrate, a visible moving boundary is created between two colors and it advances as a function of time and temperature. This provides a visual record of the time-temperature exposure of the article. In this case SP is coated but coated with solid and SP still remains porous.

U.S. Pat. Nos. 4,195,056 and 4,195,058 describe a time-temperature indicator (t-T indicator) which is constructed of a vapor-permeable barrier positioned between a vapor and an indicator, both housed in a vapor-impermeable container. The device is activated just prior to the monitoring period by providing vapor to the container, as for example, by rupturing a solvent-filled frangible reservoir. The indicator, upon contact with the vapor produces a visual color response, and the vapor is constrained to permeate through the vapor-permeable barrier before contacting the indicator, thus creating a characteristic induction period before a color response occurs. In this case SP is coated but coated with solid and SP still remains porous.

U.S. Pat. No. 4,410,493 discloses an indicator device which comprises a backing member, an indicator chemical, such as sebacic acid, which has the capability of wicking through a wick material, wicking means having one end of said wicking means in physical contact with said indicator chemical, said indicator chemical and wicking means being contained within a polypropylene envelope with the top and bottom interfaces of said envelope being sealed together to mechanically bond the wicking means and indicator chemical at the film envelope interfaces.

U.S. Pat. No. 4,448,548 discloses a steam sterilization indicator comprising a fusible material, in tablet form, deposited in an embossment in one end of a thin aluminum backing. A wicking strip is attached to the backing with one end of the strip being in close proximity to the fusible tablet. A clear plastic material covers the tablet and the strip and is adhered to the backing. The melting point of the fusible tablet is depressed in the presence of saturated steam. Upon melt, the material in the tablet is absorbed by the wicking strip, producing a color front to provide an indication of the integration of time and temperature in the presence of steam.

U.S. Pat. No. 5,045,283 discloses a moving boundary device constructed of an activator tape, containing an activator composition in an activator matrix, an indicating tape, containing an indicating composition in an indicator matrix in which the matrices are adhered together to form a wedge-shaped composite matrix, preferably by means of a pressure sensitive adhesive. The color change appears as a moving boundary at the color/non-color interface which moves transversely along the length of the device toward the thicker end of the composite matrix. The diffusion of the activator is vertical.

U.S. Pat. No. 5,180,598 discloses a liquid activated indicators comprising a porous structure which generates a first color by effects which include optical interference when pores of the structure are gas-filled, and a second contrasting color when the pores of the structure are liquid filled. The porous structure is covered with a transparent or translucent cover which is unattached in certain areas to allow for capillary movement of liquid between the cover and the porous structure. An entrance permits liquid to enter between the cover and the porous structure. When contacted with liquid, the liquid is drawn into the device and produces an expanding area of contrasting color which is used to indicate the elapse of time.

U.S. Pat. No. 5,723,336 discloses an indicator comprises a base substrate and two transparent polymeric layers on top of the base substrate in adhesive contact with each other. The indicator further comprises a valve member which is restrictive of the flow of dye therethrough, which valve is interposed between the two polymer layers such that there is no adhesive contact between the two polymer layers in the area of the valve. A deposit of colored dye is either on the lower polymeric layer, in which case the valve may be in physical contact with the dye, or on the base substrate. In either case the dye is visible through the polymeric layers, with the dye being positioned directly below the valve member, however, so that the valve member at least partially obstructs visibility of the dye deposit.

U.S. Pat. No. 7,232,253 discloses a time indicator comprising a first reservoir, a migration medium and activating means for bringing liquid from the first reservoir in contact with the migration medium so that after activation the liquid migrates through the migration medium producing a color change therein, characterized in that the activating means comprises a second reservoir connected between the first reservoir and the migration medium whereby after activation the liquid travels relatively rapidly from the first reservoir to the second reservoir and then migrates relatively slowly along the length of the migration medium over time; wherein the second reservoir is in the form if an inflatable pocket which inflates after activation.

U.S. Pat. No. 7,280,441 discloses a timer indicator or chronograph comprising: an indicator panel having a region with a number of visually distinct sections arrayed spatially relative to each other, said visually distinct sections each having at least one colorant different from an adjacent section, and having at least a reservoir containing an activating agent that constitutes a mobile phase that interacts with said indicator panel, and which transports said colorant along said indicator panel at a rate less than a rate of progression of said mobile phase for monitoring relative passage of time, and said reservoir being in controlled communication with said indicator panel.

U.S. Pat. No. 7,517,146 discloses an excess temperature indicator can provide a visual indication of past exposure of perishable, maturing and other host products to an elevated temperature exceeding a threshold temperature. The indicator can have an upper layer provided with a viewing window and a wick attached to the upper layer. A reservoir of heat-fusible indicator material can be disposed in contact with the wick, to fuse and move along the wick changing the visual appearance of a first portion of the wick viewable through the window, in response to an excess temperature event.

U.S. Pat. Nos. 7,562,811; 8,091,776 and 8,196,821 disclose a quality management system for products comprising: a multiplicity of product unit specific indicators each operative to provide a machine-readable indication of exceedance of at least one threshold by at least one product quality determining parameter, said machine-readable indication comprising a variable bar code having a first readable state and at least a second readable state, said first readable state and said at least a second readable state extending along a single axis, each readable state including digital indicia and at least start and stop code indicia, at least two digital indicia being different between said second readable state and said first readable state, wherein at least one of said start and stop code indicia which appear in said first readable state form part of said digital indicia in said second readable state and said second readable state includes additional indicia that appear at least one of before the digital indicia and after the digital indicia when the exceedance occurs; an indicator reader operative to read said product unit specific indicators and to provide output indications; and a product type specific indication interpreter operative to receive said output indications and to provide human sensible, product unit specific, product quality status outputs.

US Pat. Application No. 20120079981 discloses a temperature-activable time-temperature indicator that can be used to monitor the historical exposure of a host product to ambient temperatures includes an optically readable, thermally sensitive indicator element. The indicator element can be inactive below a base temperature and is intrinsically thermally responsive at or above an activation temperature which is equal to or greater than the base temperature. The indicator can record cumulative ambient temperature exposure above the activation temperature irreversibly with respect to time. The indicator element can include a synthetic polymeric material, and optionally, a dye. A side-chain crystallizable polymer, such as poly(hexadecylmethacrylate) that is solid below the base temperature and is a viscous liquid above the activation temperature can be employed.

US Pat. Application No. 20120236900 discloses a time-temperature indicator comprising: an indicator liquid reservoir; a migration medium; and a trigger; wherein the trigger is operable to release an indicator liquid from the reservoir upon activation of the trigger into an entrance of a channel defined within the migration medium, wherein the extent of migration of indicator liquid from the trigger area through the channel can be determined by a change in color or brightness of the migration medium and is an indication of one or both of differences in temperature and a passage of time; wherein the migration medium comprises a planar medium, having first and second major surfaces, which can absorb the indicator liquid; wherein the channel is defined within the migration medium by a rapidly cured de-wicking ink and is defined at the surface of the first and second major planes of the migration medium by first and second impermeable lamination media; and wherein at least one of the impermeable media is transparent such that a change in color or brightness can be determined, as between a trigger area of the migration path and a distal portion of the migration channel.

US Pat. Application No. 20130287059 discloses a dosimeter comprising a wick in contact with a separate reservoir containing a mix of a colored dye, a wax and an amorphous polymer to indicate a distinct temperature range when the mix melts. The wicks are preferably made of porous paper with a pore size around 8 microns to allow for proper capillary action along its length. An adhesive, except where each wick contacts its respective reservoir and at a vent, preferably seals each wick.

In known art moving boundary indicating devices, the stationary phase (SP) is a porous material, such as paper and the mobile phase (MP) is a liquid. MP in these devices is a liquid and hence the movement of the boundary is fast and the maximum service life is short, e.g., maximum of about a couple weeks at room temperature. The known devices are difficult to make as a special construction of the liquid reservoir is required and devices require sealing, usually heat sealed at the edges to control the movement of the liquid. It is also difficult to make small, e.g., smaller than a centimeter devices. In the known moving boundary devices, the mobile phase moves as a liquid and not as a vapor. There is no report on indicating devices based on diffusion of vapor of a MP (e.g., vapor of a solid compound which sublimes) through a non-porous polymeric SP.

Thus there remains a need for moving boundary devices that have longer lifetimes, are easier to make and have improved reliability.

OBJECTIVES OF THE INVENTION

Accordingly, a main objective of the current invention is to develop a variety of indicating devices, such as time, temperature, time-temperature, food doneness, thaw, humidity and sterilization indicators based on lateral diffusion of a vapor of a solid or liquid MP through a non-porous, non-absorbing and/or non-adsorbing SP.

Another main objective of the invention is to make indicating devices based on lateral diffusion of a solution, liquid or solid MP through a layer of a group comprising non-porous, non-adsorbing and non-absorbing SP.

Another main objective of the invention to make indicating devices based on lateral diffusion of a MP through a layer of non-porous polymeric SP.

Another main objective of the invention is to make indicating devices based on lateral diffusion of a MP through a layer of an adhesive as a SP.

Another main objective of the invention is to make indicating devices based on lateral diffusion of a MP through a layer of a pressure sensitive adhesive as a SP.

Another main objective of the invention is to make indicating devices based on lateral diffusion of a MP through a layer of a hot melt adhesive as a SP.

Another main objective of the invention is to select a material as MP which has ability to rapidly diffuse through a layer of a non-porous SP.

Another main objective of the invention is to make moving boundary indicating devices wherein diffusion of a MP creates a noticeable boundary in a layer of a non-porous SP.

Another main objective of the invention is to make indicating devices based on lateral diffusion of a MP through a layer of a non-porous SP which creates or destroys a message, image, barcode and alike.

Another main objective of the invention is to make mini (e.g., smaller than a few centimeter) indicating devices based on lateral diffusion of a MP through a layer of a non-porous SP.

Another main objective of the invention is to make indicating devices based on lateral diffusion of a MP through a layer of a non-porous SP where SP and MP are separated by a barrier layer.

Another main objective of the invention is to make indicating devices based on lateral diffusion of a MP through a layer of a non-porous SP where SP and MP are separated by a non-permeable barrier layer.

Another main objective of the invention is to make indicating devices based on lateral diffusion of a MP through a layer of a non-porous SP where SP and MP are separated by a non-permeable barrier layer having at least one release layer.

Another main objective of the invention is to make indicating devices based on lateral diffusion of a MP through a layer of a non-porous SP where SP and MP are separated by a permeable barrier layer.

Another main objective of the invention is to make indicating devices based on lateral diffusion of a MP through a layer of a non-porous SP where SP and MP are separated by a wedge shaped permeable barrier layer.

Another main objective of the invention is to make indicating devices based on lateral diffusion of a MP through a layer of a non-porous SP where the devices have a mask to prevent movement of the boundary being noticed for a pre-determined time.

Another main objective of the invention is to make indicating devices based on lateral diffusion of a MP through a layer of a non-porous SP where in there is an additional layer of indicator or activator on or below SP layer.

Another main objective of the invention is to vary service life, rate of movement of boundary, rate of reaction and activation energy of indicating devices based on lateral diffusion of a MP through a layer of a non-porous SP by varying parameters, such as thickness, concentration, quantity and/or nature of MP, SP, barrier, activator, indicator, pre-cursor, additional layers and additives.

Another main objective of the invention is to make indicating devices based on lateral diffusion of a MP through a layer of non-porous SP made from a porous SP by filling the pours with a solid, solution or liquid including plasticizers, low molecular weight compounds and polymeric materials such as adhesives.

Another main objective of the invention is to make indicating devices based on lateral diffusion of a coloring material such as dye through a layer of a non-porous SP.

Another main objective of the invention is to make indicating devices based on lateral diffusion of a MP comprising an activator, through a layer of a non-porous SP comprising an indicator, or vice versa.

Another main objective of the invention is to make indicating devices based on lateral diffusion of a MP, comprising an acid or base as an activator through a layer of a non-porous SP comprising a pH sensitive dye, or vice versa.

Another main objective of the invention is to make indicating devices based on lateral diffusion of a MP comprising a chelating agent as an activator through a layer of a non-porous SP comprising a metal salt or organo metallic compound as an indicator or vice versa.

Another main objective of the invention is to make indicating devices based on lateral diffusion of a MP composed or comprising a volatile or sublimeable composition through a layer of a non-porous SP.

Another main objective of the invention is to make indicating devices based on lateral diffusion of a MP comprising or composed of a sublimeable coloring composition through a layer of a non-porous SP.

Another main objective of the invention is to make indicating devices based on lateral diffusion of a MP comprising a sublimeable dye or activator through a layer of a non-porous SP.

Yet another main of the invention is to increase the rate of diffusion of a MP through a non-porous SP by adding a composition in MP and/or SP.

Yet another main objective of the invention is to increase the rate of diffusion of a MP through a non-porous SP by adding a sublimeable or volatile composition in MP.

Yet another main objective of the invention is to increase the rate of diffusion of a MP through a non-porous SP by adding a composition such as solvents, plasticizers, oligomer, low molecular weight polymers, compounds which melt between −20° C. and 200° C. and nano or microns sized particles, which softens SP.

Yet another main objective of the invention is to decrease the rate of diffusion of a MP through a non-porous SP by adding a composition in a MP and/or a SP.

Yet another main objective of the invention is to decrease the rate of diffusion of a MP through a non-porous SP by adding a composition which consumes, neutralizes, reacts, absorbs, hardens or crosslinks a SP and/or MP.

Yet another main objective of the invention is to control the rate of diffusion of a MP through a non-porous SP by controlling the amount and nature of accelerator or retarder in MP and/or SP.

Yet another main objective of the invention is to control the rate of release of a MP by adding an additive in MP.

Yet another main objective of the invention is to control the rate of release of a MP by adding an additive in MP wherein the additive is an oligomer or a polymer.

Another main objective of the invention is to make indicating devices based on lateral diffusion of a MP through a layer of a non-porous SP wherein MP is composed of one or more of activator, indicator, coloring composition, accelerator, retarder, controller, volatile, subliming solid and additive.

Another main objective of the invention is to make indicating devices based on lateral diffusion of a MP through a layer of a non-porous SP wherein SP is composed of polymeric binder and one or more of activator, indicator, coloring composition, accelerator, retarder, controller, volatile, subliming solid and additive.

Yet another objective of the invention is to make indicating devices based on lateral diffusion of a MP through a layer of a non-porous SP.

Yet another objective of the invention is to make an activator tape or MP tape composed of at least one MP or an activator with or without a polymeric matrix on a substrate, such as a plastic film.

Yet another objective of the invention is to make an indicator tape or SP tape composed of at least one SP or an indicator in a polymeric binder on a substrate, such as a plastic film.

Yet another objective of the invention is to make two tape indicating devices composed of (1) an activator tape or MP tape (2) an indicator tape or SP tape which can be activated by applying one tape over the other, wherein the indicator or mobile phase come in contact with activator or stationary phase.

Another objective is to provide a device for indicating two or more of freeze, thaw, temperature and time-temperature.

BRIEF SUMMARY OF THE INVENTION

This invention relates to an indicating device based on lateral diffusion of a mobile phase through a layer of a non-porous stationary phase comprised of a mobile phase layer; and a non-porous, non-adsorbing or non-absorbing stationary phase layer; wherein a vapor of the mobile phase laterally diffuses through the stationary phase layer and creates a noticeable or measurable boundary.

In one embodiment of the invention the mobile phase is a solid, liquid or mixture thereof.

The mobile phase layer is substantially smaller in area than the stationary phase layer. The mobile phase and stationary phase are either coated on the same or different substrate.

In another embodiment the stationary phase layer and mobile phase layer are sandwiched between two substrates.

In another embodiment the mobile phase layer is in the form of a dot, bar or line either in the middle or at one end of the stationary phase layer.

In another embodiment the mobile phase is capable of diffusing through the stationary phase.

In yet another embodiment the mobile phase is a coloring material. The coloring material may be a dye or pigment.

The indicating devise of the invention is capable of producing a noticeable or measurable change, including a change in conductivity, resistivity, phase, state or optical such as color, fluorescence, clarity and opacity.

In another embodiment the mobile phase is a part of an activator-indicator pair. The activator and indicator are capable of reacting to produce a coloring material or noticeable change. The mobile phase can be a part of a pair of (i) an acid, base, or salt and a pH dye, or (ii) metal ion or metal complex and a chelate.

In another embodiment n the mobile phase layer is comprised of a mobile phase, a binder, a coloring material, either an activator or an indicator, and a controller.

In another embodiment the stationary phase is a polymeric material permeable to the mobile phase. The polymeric material is an adhesive, such as a pressure sensitive or hot melt. It can also be a polymer or copolymer of an acrylic, ether, imide, imine, urethane, cyanoacrylate, olefin, vinyl, styrene, silicone or epoxy.

In another embodiment the indicating device further comprises a controller which is an adjuvant additive which can control, adjust, or modify the properties and performance including rate of reaction, rate of movement of the mobile phase, rate of movement of the boundary and activation energy of the indicating device.

In another embodiment the stationary phase is comprised of a polymeric material, an indicator or an activator and a controller. The controller can be a solvent, volatile or subliming solid, oligomer, plasticizer, viscosity modifier, crosslinking agent, retarder or accelerator.

In yet another embodiment of the invention a marker, scale, mask or message is printed on any surface of a layer of the indicating device. In a preferred embodiment the layer is a substrate. The scale can be in the form of open or solid circles, lines, barcodes, or numbers. The mask can be a solid opaque coating in the form of a circle or bar capable of masking or making the boundary invisible or unmeasurable for a pre-determined period. The device can have one or more messages which appear, disappear or are blocked. The message can be a word or symbol, two messages which do not start to become observable at the same time, one which indicates a condition or treatment, one message indicates un-doneness, freshness, usability, acceptability of the item and a second message alone or in combination with the first indicates doneness, spoilage, unusability and unacceptability of the item after a treatment or where the first message indicates non-sterility, non-usability, unacceptability of the item and the second message alone or in combination with the first indicates doneness, sterility, usability and acceptability of the item after a treatment.

In another embodiment the service life, rate of reaction, rate of permeation, rate of movement of boundary, and activation energy of the indicating devices can be varied by varying parameters selected from the group of: nature and thickness of a stationary phase, nature and concentration or amount of the mobile phase or co-mobile phase, nature and concentration of an activator, nature and concentration of an indicator, nature and thickness of a layer of the device in a permeable layer and the nature and concentration of a controller. The controller can be capable of changing a viscoelastic property or mobility of molecules of the mobile phase and/or stationary phase.

In another embodiment indicating device has activation energy between 0 and 60 kcal/mole and time for the boundary to travel a predetermined distance is between 1 hour and 10 years.

In yet another embodiment the device comprises a mobile phase tape composed of a mobile phase, an activator or an indicator, a binder and a controller on a substrate. The substrate can be a plastic film.

In another embodiment the device comprises a stationary phase tape comprised of a stationary phase, an indicator or an activator, and a controller on a substrate, wherein for example, the substrate is a plastic film.

Another embodiment relates to a device comprising (1) a mobile phase tape (2) a stationary phase tape which can be activated by applying one tape over the other so that the mobile phase comes in contact with the stationary phase.

In another embodiment the device is a sealed or unsealed circular, long sealing tape or a small rectangular device.

In another embodiment device of the invention further comprises an extra layer selected from permeable layer, non-permeable barrier layer, reactive layer, destroyable or degradable barrier layer, an expiration indicating layer, a tamper indicating layer, an activation indicating layer, a message or image creating layer, a separating layer, mask layer, a removable layer, a disappearing layer, an appearing layer, an activator layer, an indicator, a microencapsulated layer, a thermally printable layer, and a whole, partial or discontinuous layer, in form of a pattern, message or image. The extra layer may contain an indicator layer or activator layer adjacent to stationary phase layer.

In another embodiment the indicating device is based on lateral diffusion of a mobile phase through a layer of a non-porous stationary phase comprising a stationary phase, a mobile phase, an activator, an indicator, an additive, a controller and at least one additional layer selected from the group consisting of a substrate, a permeable layer, a wedge shaped permeable layer, a barrier layer, a reactive layer, destroyable or degradable barrier layer, an expiration indicating layer, a tamper indicating layer, an activation indicating layer, a message or image creating layer, separating layer, removable layer, a microencapsulated layer and a printable layer.

Another embodiment relates to a process of monitoring a change which comprises using an indicating device based on lateral diffusion of a mobile phase through a layer of a non-porous stationary phase to indicate a change in time, temperature, time-temperature, freeze, thaw, heating, cooling, humidity, doneness of food, microwave and sterilization including sterilization with steam, ethylene oxide, a peroxide, plasmas of a peroxide, formaldehyde and dry heat by monitoring a change in the indicating device.

In yet another embodiment the process of monitoring a change comprises using an indicating device based on lateral diffusion of a mobile phase through a layer of a non-porous stationary wherein a change of time-temperature indicating the shelf life of perishables is monitored by monitoring a change in the indicating device. The perishables can be selected from one or more of fresh, refrigerated, or frozen, vegetables, fruits, meats, fish, poultry, dairy products, bakery products, juices, pre-cooked foods, soft and alcoholic beverages, pharmaceutical, vaccine, biological sample, cosmetics and reactive chemicals.

In another embodiment of the invention, the device can have a service life of from about 1 hour to about 10 years, preferably from about 1 to about 30 days. The device can be used at a temperature of from about −40° C. to about 200° C., preferably from about −20° C. to about 60° C.

In another embodiment the concentration of mobile phase can from about 20% to 100%, preferably from about 70% to 100%.

In another embodiment the concentration of the controller can be from about 5% to about 95%, preferably from about 55 to about 50%.

In another embodiment, the quantity of mobile phase can be from about 0.1 mg to about 1 g depending upon the size of the device. Preferably the weight is from about 1 mg to about 10 mg.

In another embodiment the size of mobile phase depends on the shape of the device. The shape can be circular and the size of mobile phase can be from about 0.1 mm$^2$ to about 5 cm$^2$, preferably from about 1 mm$^2$ to about 10 mm$^2$.

In another embodiment the thickness of the stationary phase layer is from about 10 nm to about 1 mm, preferably from about 10 microns to about 100 microns.

In another embodiment the thickness of substrates is from about 10 microns to about 1 mm, preferably from about 10 microns to about 100 microns.

In another embodiment the activation energy of the device is from essentially zero kcal/mole to about 100 kcal/mole, preferably from about 20 to about 40 kcal/mole for time-temperature indicating devices, 40-100 kcal/mole for steam sterilization indicator and 0-15 kcal/mole for time indicating devices.

In another embodiment the device is a time, temperature, time-temperature, threshold time-temperature, thaw, humidity, food doneness or sterilization indicator.

Another embodiment relates to an indicating device based on lateral diffusion of a mobile phase through a layer of a non-porous stationary phase comprised of a mobile phase layer; and a non-porous, non-adsorbing or non-absorbing stationary phase layer which indicates the status of a perishable wherein the perishable is a food item, such as fresh, refrigerated, or frozen, vegetables, fruits, meats, fish, poultry, dairy products, bakery products, juices, pre-cooked foods, soft and alcoholic beverages, or a nonfood item, such as a pharmaceutical, vaccine, biological sample, such as sera, blood, or blood plasma, cosmetics, battery, reactive chemical compound or a biochemical product.

Yet another embodiment relates to an indicating device based on lateral diffusion of a mobile phase through a layer of a non-porous stationary phase comprised of a mobile phase layer; and a non-porous, non-adsorbing or non-absorbing stationary phase layer which is used as or on a safety sticker, self-timing retail sticker, biological industrial process monitor, self-expiring sticker to prevent re-use, security ID label, visitors badge, self-expiring parking tag, package and shipping label, wrist band, time indicating ticket for trains, buses, spot events, theaters etc., self-expiring pass for tours, emergency rooms, hospitals, museums, and other locations, race track pass, security label for screened luggage, purse, bag at airports to indicate that such items have been inspected, and at unmanned but video controlled entrances for visitors where a self-expiring visitor label is issued electronically.

Another embodiment relates to an indicating device based on lateral diffusion of a mobile phase through a layer of a non-porous stationary phase comprised of a mobile phase layer; and a non-porous, non-adsorbing or non-absorbing stationary phase layer which is used as a sterilization indicator. The sterilization can be with steam or dry heat.

In another embodiment the mobile phase is coated at periphery of the device and the boundary moves towards the center of the stationary phase.

In another embodiment the indicating device has multiple mobile phases having different rates of diffusion through the stationary phase.

In another embodiment the device further comprises a freeze, thaw or temperature indicator.

In another embodiment the device has a boundary that is self-shape correcting.

Yet another embodiment relates to an indicating device comprising a substantially solid mobile phase located substantially in the middle of a non-porous, non-adsorbing or non-absorbing stationary phase wherein a vapor of the mobile phase laterally permeates through the stationary phase and creates a noticeable or measurable boundary.

Another embodiment relates to a device wherein a vapor of substantially solid mobile phase first permeates vertically followed by lateral permeation in a substantially non-porous, non-adsorbing or non-absorbing solid phase and creates a noticeable or measurable boundary.

In another embodiment the boundary moves in all lateral directions or in opposing two lateral directions.

In another embodiment the device is self-sealing either by pressure or heat on entire device.

In another embodiment the device is self-sealing and additionally not sealed at the edges.

In another embodiment the components of the device are unaffected by undesired ambient effects including humidity, water, and sunlight.

Another embodiment relates to a process of applying the devices on perishables.

In another embodiment the nonporous stationary phase is created by filling the pores of a porous stationary phase such as a polymer, plasticizer, adhesive or solvent.

In another embodiment the movement of the boundary is linear with time.

In another embodiment the device becomes a time-temperature indicator above a predetermined or a narrow range of temperature.

BRIEF DESCRIPTION OF FIGURES

The objects, features and advantages of the present inventions will be apparent from the following description of the invention as illustrated in the accompanying drawings, examples and preferred embodiments.

DETAILED DESCRIPTION OF THE INVENTION

Figure 1:
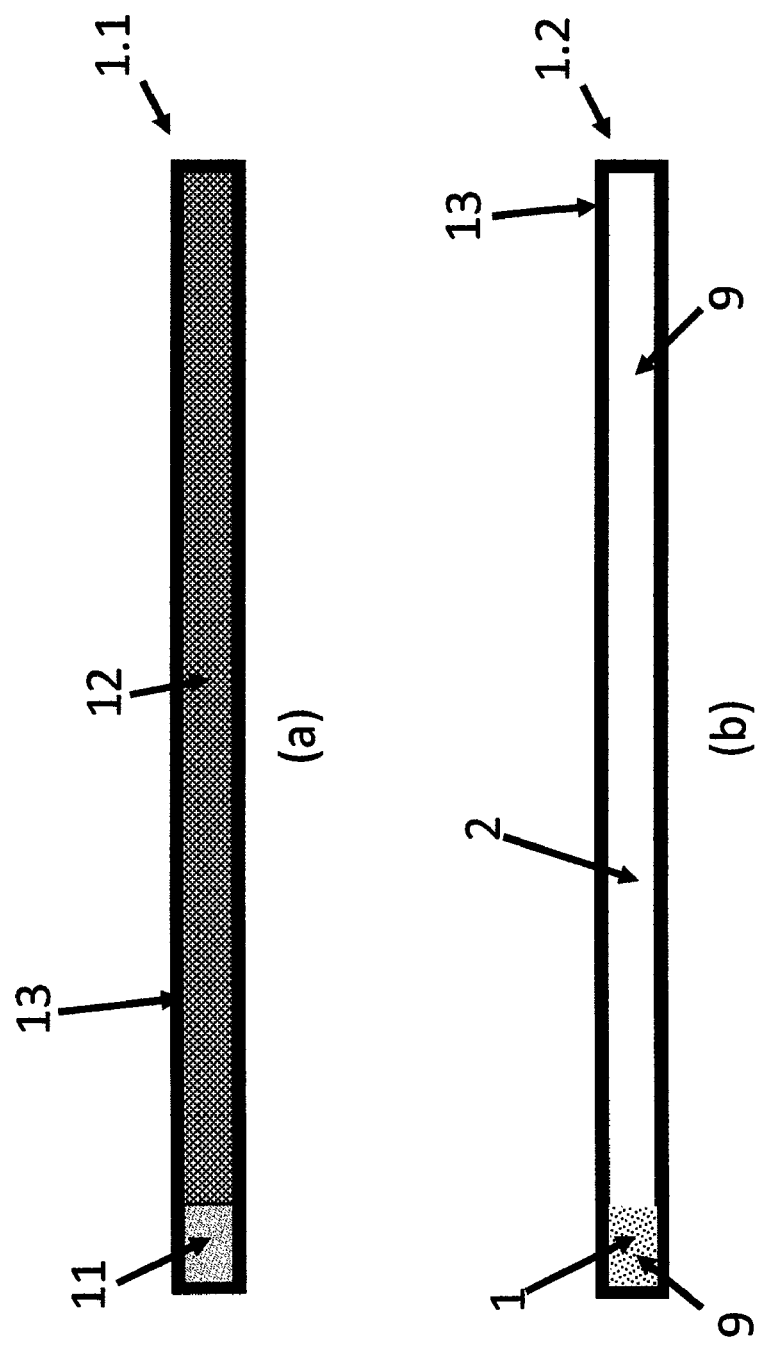
FIG. 1 is a cross sectional schematic presentation of moving boundary devices of (*a*) a known art and (*b*) a current invention.

This invention relates to an indicating system based on diffusion of a MP through a non-porous SP. The indicating devices are capable of indicating various influences on a subject, such as time, temperature, time-temperature, food doneness, thawing, humidity and sterilization indicators. The indicating devices are based on lateral diffusion of a solution, liquid or solid MP through a layer of a group comprising non-porous, non-adsorbing and non-absorbing SP.

In order to more fully understand the invention, the following definitions of terms are set forth:

Accelerator: A composition which can increase the diffusion of a mobile phase through a stationary phase. An example of an accelerator is a sublimeable solid, solvent for MP, high viscosity liquids, a low melting compound such as a wax or a plasticizer for SP. An accelerator can be a liquid and can be in MP and/or SP.

Activated device: When an activator tape or mobile phase tape is applied on to indicator or stationary phase tape wherein the activator or mobile phase come in contact with indicator or stationary phase.

Activator tape or mobile phase tape: A tape composed of at least one mobile phase or an activator on a substrate, such as a plastic film.

Activator: A material which when reacts with an indicator develops a noticeable change, e.g., color, fluorescence or other measurable change. The activator can be in either the mobile or the stationary phase.

Controller: An accelerator or retarder which controls the diffusion of a mobile phase in the stationary phase.

Diffusion: A process of migration of a mobile phase through a stationary phase. The words diffusion, permeation, movement or migration are used interchangeably herein.

Circular device: A device of current invention in which an MP is spotted in form of a dot on a SP or applied on to a SP and migration of MP occurs in all lateral directions in SP.

Indicating devices: Devices or systems for monitoring materials and processes, such as time, temperature, time-temperature, humidity, doneness of foods, sterilization (including steam, ethylene oxide, formaldehydes, peroxide and plasmas), toxic chemicals and the like.

Indicator tape or stationary phase tape: A tape composed of at least one stationary phase or an indicator on a substrate, such as a plastic film.

Indicator: A material which when reacts with an activator develops a noticeable change, e.g., color, fluorescence or other measurable changes. Indicator can be in either mobile or stationary phase.

Lateral diffusion: Diffusion of a mobile phase along the length or flat plane of a stationary phase, i.e., in the horizontal, in plane, parallel, flat or sideways of a stationary phase.

Mobile phase (MP): A composition which has an ability to diffuse or permeate through a stationary phase, either by itself or with an aid of other materials such as accelerator. An example of a mobile phase is usually a solid dye, an indicator, an activator, a sublimeable compound or very viscous low molecular weight compound. A mobile phase can also be composed of or can contain other compositions, such as a solvent, accelerator, retarder and/or other additives. It can also be a liquid, solution or a solid dissolved in a liquid.

Moving boundary device: An indicating device or system in which a boundary, border, edge or ring is created by a mobile phase when it moves along the flat surface of a stationary phase.

Non-porous: A solid material, such as a plastic film or a layer of an adhesive which does not have pores similar to that of a paper, and it can let a vapor, liquid, solution or sublimed solid pass/diffuse/permeate through. This definition includes a porous material whose pores are substantially filled with a solid, liquid or solution and has no substantial ability to absorb or adsorb other materials.

Porous: A solid material, such as paper (including a coating of fine particle of a porous composition, such as silica gel) which has pores which can be microscopic and has ability to hold a material, usually a liquid due to processes, such as absorption, adsorption and alike. The movement of a liquid in a porous substrate, such as paper is usually by a process called capillary action or wicking.

Retarder: A composition which can decrease the diffusion of a mobile phase through a stationary phase. An example of retarder is a crosslinking agent, absorbing or adsorbing material or a neutralizing agent.

Service life: It is the maximum usable time the indicating device can be used at a given temperature. In case of a moving boundary device, service life is the time required for the boundary to move from one end of the device to the other or at a predetermined distance. Once the device is activated, the service life and shelf-life are the same.

Stationary phase (SP): A composition, usually polymeric through which a mobile phase can diffuse or permeate. An example of a stationary phase is a thin layer of a pressure sensitive or hot melt adhesive, or a polymeric layer such as plastic film or coating.

Stationary phase may contain other compositions, such as accelerator, retarder, indicator or activator and other additives. The SP is usually applied on a substrate and can be sandwiched between two substrates.

Two tape device: An indicating device or system composed of (1) an indicator tape or stationary phase tape and (2) an activator tape or mobile phase tape. It can be activated (applied one over the other) or stored in an un-activated form (e.g., kept separated).

Un-activated device: Usually referred to a two tape device wherein indicator tape or mobile phase tape are not in direct contact with each other.

Vertical diffusing device: An indicating device or system in which diffusion of a composition occurs in perpendicular or vertical direction to the flat surface of the device.

Vertical diffusion: Diffusion of a mobile phase perpendicular to flat surface of a stationary phase, i.e., in the vertical, perpendicular or across a stationary phase.

The above definitions are of broad and of general nature and not specific.

Figure 2:
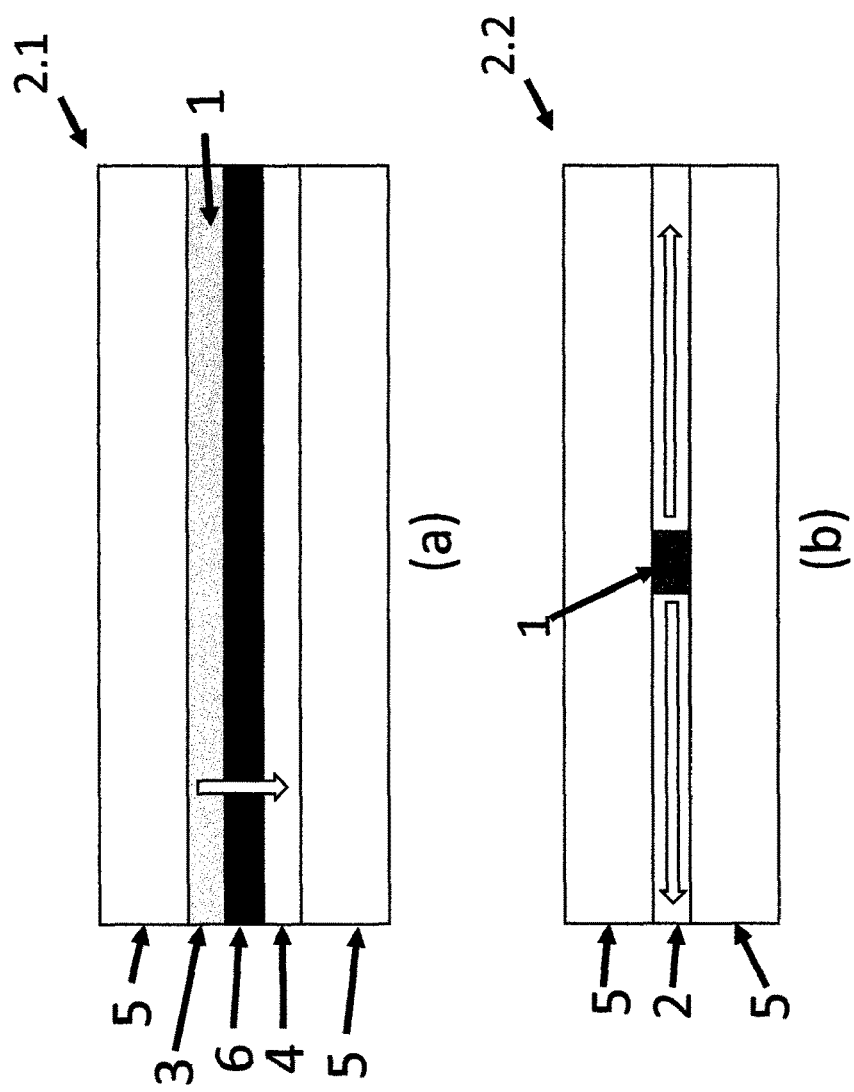
FIG. 2 is a cross sectional schematic presentation of indicating devices of (*a*) a known art where diffusion of MP is vertical and (*b*) a current invention where diffusion of MP is horizontal. Direction of diffusion of MP is indicated by hollow arrows.
Figure 4:
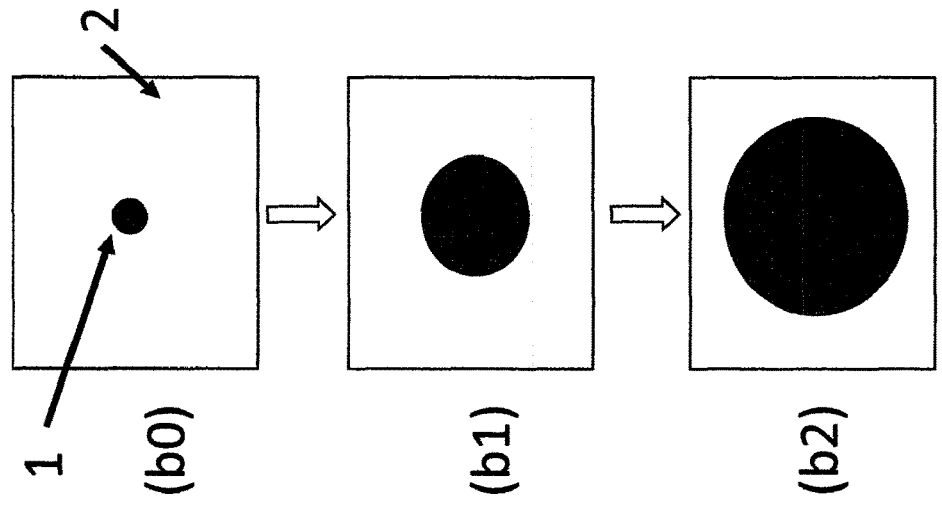
FIG. 4 is (*a*) a cross sectional and (*b*) top views of a two tape type (*a*1) un-activated and (*a*2) activated device wherein MP moves in lateral two dimensions to create a circle.
Figure 4:
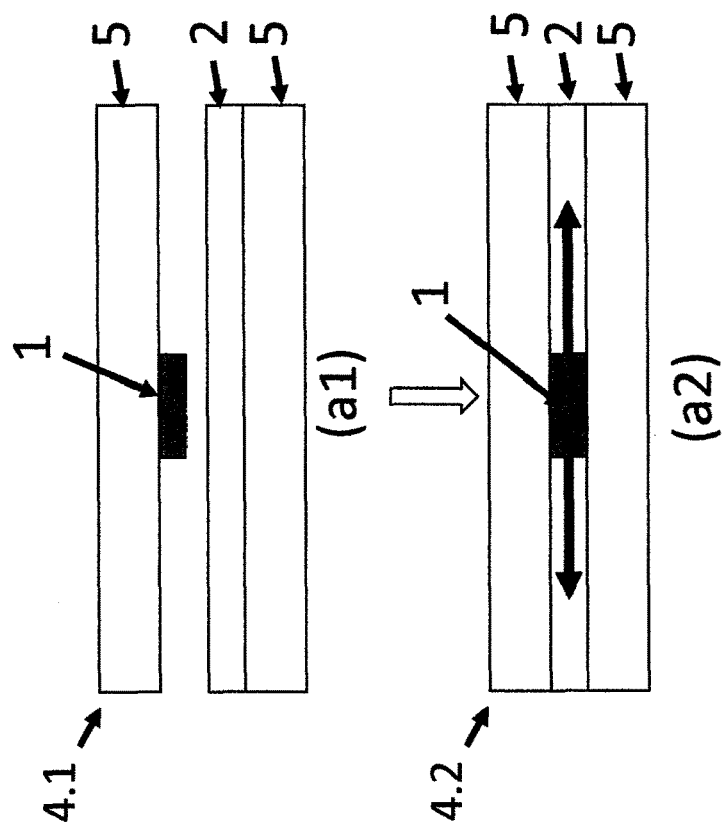
Figure 5:
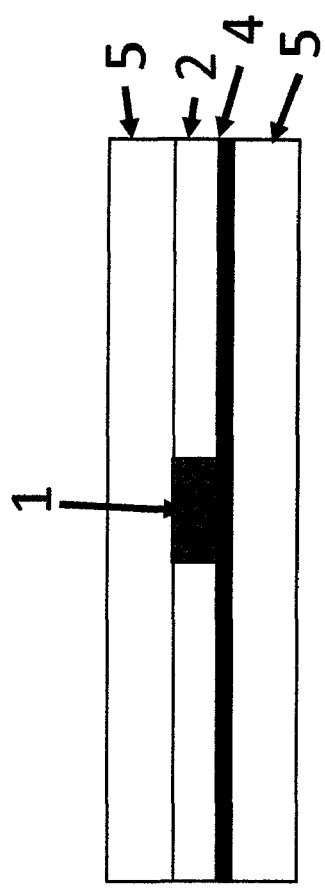
FIG. 5 is a cross sectional schematic presentation of an activated two tape device having an indicator layer under the SP layer.

In a major embodiment, the indicating system of the invention is comprised of a MP and a layer of substantially non-porous SP on a substrate or between substrates, wherein vapor of MP diffuses laterally through a layer of the SP as shown schematically in FIGS. 2(b), 4 and 5. The devices are based on diffusion of a vapor of solid or liquid MP through a solid SP in lateral direction. The diffusion is through a non-porous material like a polymeric layer such as a pressure sensitive adhesive, typically sandwiched between two plastic films.

In one embodiment, the MP is comprised of an agent whose vapor is capable of diffusing through the SP.

In another embodiment, the MP is a coloring material which creates a visible boundary in the SP layer. The movement of the boundary is initially linear mainly because there is constant supply of mobile phase and very little is used in the SP. When the SP is porous, significant quantity of MP is used to fill the pores.

A preferred coloring MP is a dye, more preferably liquid, volatile, diffusible or sublimeable dye. The preferred MP is relatively a small molecule of about 200-500 g/mole so it can easily diffuse through the SP but preferably not through the substrates of the indicating device. The coloring material may further comprise a liquid or a sublimeable accelerator. A number of organic, inorganic and organo metallic compounds, including some dyes are sublimeable and diffusible or permeable through a polymeric material that can be used for the current inventions.

In another embodiment, the MP is a colorless activator capable of producing coloring material when it diffuses through the SP, for example by reacting with an indicator dispersed or dissolve in or adjacent to the layer of the SP.

A coloring material as MP is preferred but a non-coloring activator which when reacts with an indicator in SP produces a coloring material can also be used as MP.

In case of wicking a liquid or very viscous liquid diffuses through porous media such as paper via capillary action.

As MP diffusing through a polymer layer, especially through PSA or soft polymers, movement is controlled by volatility and permeability of MP and additives and/or softness of SP. Silicone type PSA are more flexible and the rate is faster. SP can be a hot melt adhesive. In order to make the devices insensitive to undesired effect of ambient conditions such as light humidity, one can select MP, SP and additives which not sensitive to the undesirable ambient conditions.

Another main embodiment relates to indicating devices based on lateral diffusion of a MP through a layer of non-porous polymeric SP.

Another main embodiment relates to indicating devices based on lateral diffusion of a MP through a layer of an adhesive as a SP.

Another main embodiment relates to indicating devices based on lateral diffusion of a MP through a layer of a pressure sensitive adhesive as a SP.

Another main embodiment relates to indicating devices based on lateral diffusion of a MP through a layer of a hot melt adhesive as a SP.

Another main embodiment relates to a material as MP which has ability to rapidly diffuse through a layer of a non-porous SP.

Another main embodiment relates to moving boundary indicating devices wherein diffusion of a MP creates a noticeable boundary in a layer of a non-porous SP.

Another main embodiment relates to indicating devices based on lateral diffusion of a MP through a layer of a non-porous SP which creates or destroys a message, image, barcode and alike.

Another main embodiment relates to mini (e.g., smaller than a few centimeter) indicating devices based on lateral diffusion of a MP through a layer of a non-porous SP.

Another main embodiment relates to indicating devices based on lateral diffusion of a MP through a layer of a non-porous SP where SP and MP are separated by a barrier layer.

Another main embodiment relates to indicating devices based on lateral diffusion of a MP through a layer of a non-porous SP where SP and MP are separated by a non-permeable barrier layer.

Another main embodiment relates to indicating devices based on lateral diffusion of a MP through a layer of a non-porous SP where SP and MP are separated by a non-permeable barrier layer having at least one release layer.

Another main embodiment relates to indicating devices based on lateral diffusion of a MP through a layer of a non-porous SP where SP and MP are separated by a permeable barrier layer.

Another main embodiment relates to indicating devices based on lateral diffusion of a MP through a layer of a non-porous SP where SP and MP are separated by a wedge shaped permeable barrier layer.

Another main embodiment relates to indicating devices based on lateral diffusion of a MP through a layer of a non-porous SP where the devices have a mask to prevent movement of the boundary being noticed for a pre-determined time.

Another main embodiment relates to indicating devices based on lateral diffusion of a MP through a layer of a non-porous SP where in there is an additional layer of indicator or activator on or below SP layer.

Another main embodiment relates to service life, rate of movement of boundary, rate of reaction and activation energy of indicating devices based on lateral diffusion of a MP through a layer of a non-porous SP by varying parameters, such as thickness, concentration, quantity and/or nature of MP, SP, barrier, activator, indicator, pre-cursor, additional layers and additives.

Another main embodiment relates to indicating devices based on lateral diffusion of a MP through a layer of non-porous SP made from a porous SP by filling the pours with a solid, solution or liquid.

Another main embodiment relates to indicating devices based on lateral diffusion of a coloring material such as dye through a layer of a non-porous SP.

Another main embodiment relates to indicating devices based on lateral diffusion of a MP comprising an activator, through a layer of a non-porous SP comprising an indicator, or vice versa.

Another main embodiment relates to indicating devices based on lateral diffusion of a MP, comprising an acid or base as an activator through a layer of a non-porous SP comprising a pH sensitive dye, or vice versa.

Another main embodiment relates to indicating devices based on lateral diffusion of a MP comprising a chelating agent as an activator through a layer of a non-porous SP comprising metal salt or organo metallic compound as an indicator or vice versa.

Another main embodiment relates to indicating devices based on lateral diffusion of a MP composed or comprising a volatile or sublimeable composition through a layer of a non-porous SP.

Another main embodiment relates to indicating devices based on lateral diffusion of a MP comprising or composed of a sublimeable coloring composition through a layer of a non-porous SP.

Another main embodiment relates to indicating devices based on lateral diffusion of a MP comprising a sublimeable dye or activator through a layer of a non-porous SP.

Yet another main embodiment relates to the increase the rate of diffusion of a MP through a non-porous SP by adding a composition in MP and/or SP.

Yet another main embodiment relates to the increase the rate of diffusion of a MP through a non-porous SP by adding a sublimeable or volatile composition in MP.

Yet another main embodiment relates to the increase of the rate of diffusion of a MP through a non-porous SP by adding a composition such as solvents or plasticizer which softens SP.

Yet another main embodiment relates to the decrease of the rate of diffusion of a MP through a non-porous SP by adding a composition in a MP and/or a SP.

Yet another main embodiment relates to the decrease of the rate of diffusion of a MP through a non-porous SP by adding a composition which consumes, neutralizes, reacts, absorbs, hardens or crosslinks a SP and/or MP.

Yet another main embodiment relates to the control of the rate of diffusion of a MP through a non-porous SP by controlling the amount and nature of accelerator or retarder in MP and/or SP.

Yet another main embodiment relates to the control of the rate of release of a MP by adding an additive in MP.

Yet another main embodiment relates to the control of the rate of release of a MP by adding an additive in MP wherein the additive is an oligomer or a polymer.

Another main embodiment relates to indicating devices based on lateral diffusion of a MP through a layer of a non-porous SP wherein MP is composed of one or more of activator, indicator, coloring composition, accelerator, retarder, controller, volatile, subliming solid and additive.

Another main embodiment relates to indicating devices based on lateral diffusion of a MP through a layer of a non-porous SP wherein SP is composed of polymeric binder and one or more of activator, indicator, coloring composition, accelerator, retarder, controller, volatile, subliming solid and additive.

Yet another main embodiment relates to indicating devices based on lateral diffusion of a MP through a layer of a non-porous SP as exemplified in FIGS. 1(b), 2(b), and 4 through 12.

Yet another embodiment relates to an activator tape or MP tape composed of at least one MP or an activator with or without a polymeric matrix on a substrate, such as a plastic film.

Yet another embodiment relates to an indicator tape or SP tape composed of at least one SP or an indicator in a polymeric binder on a substrate, such as a plastic film.

Yet another embodiment relates to two tape indicating devices composed of (1) an activator tape or MP tape (2) an indicator tape or SP tape which can be activated by applying one tape over the other, wherein the indicator or mobile phase come in contact with activator or stationary phase.

Another embodiment relates to a device for indicating two or more of freeze, thaw, temperature and time-temperature.

Another embodiment relates to a chromatographic technique which is based diffusion of a vapor through a non-porous, non-adsorbing, non-absorbing SP, in this case the SP is polymeric, especially an adhesive. MP swells SP but does not dissolve the SP.

An activator MP of the invention comprises any composition that can react with an indicator to cause a color change, preferably irreversible color change. More particularly, activators of the invention comprise acids, bases, salts, chemical or biological agents and chelates that readily react with indicator composition such as a pH dye to produce a color change can be used for the indicating systems. Also contemplated within the invention are precursors of the activators, that is, compositions that can be acted on by additional components of the indicating system to form the activators of the invention. A MP can be dissolved or dispersed in a binder or non-SP porous material.

The stationary phase can be any non-porous, preferably polymeric material. Pressure sensitive adhesives (PSA) and hot melt adhesives are the most preferred SP. PSA can bond with the substrates. Many low molecular weight dyes can diffuse through the polymeric layer. If an activator is used as MP, one need to dissolve or disperse an indicator in or adjacent to the SP layer.

Another embodiment of the invention relates to an indicating system which comprises a) a MP tape and b) a SP tape, wherein the MP tape comprises a substrate to which is affixed at least one MP and the SP tape comprises at least one layer of a non-porous SP.

Yet another embodiment of the invention relates to an indicating system which comprises a composite of an indicator tape and an activator tape, bonded together with at least one bonding layer wherein the MP tape comprises a substrate to which is affixed at least one MP and the SP tape comprises a layer of the SP.

In another embodiment, the indicating devices can also have an adhesive layer on a substrate to attach the indicating system to the item to be monitored.

The invention also relates to a process of making the indicating systems of the invention. In one embodiment, the indicating tape of the invention can be made by laminating an MP tape on an SP tape. In another embodiment a layer of MP is coated on a layer of SP with and without a permeable layer. In another embodiment, additional layers can be added to the indicating system.

Another embodiment of the indicating system of the invention comprises a system wherein an additional one or more layers are added to the system, wherein the layers are selected from a binder layer, a layer permeable to MP, a wedge shaped layer permeable to MP, a barrier to permeation of MP, reactive layer, destroyable or degradable barrier layer, an expiration indicating layer, a tamper indicating layer, an activation indicating layer, a message or image creating layer or a separating layer, a removable layer, a disappearing layer, an appearing layer, an activable layer, masking layer, a microencapsulated layer, thermally printable layer, and like, and others known in the art.

Yet another embodiment of the invention comprises an indicating sealing tape, a very longer version of the indicating system. It can be further comprising a two tape dispenser for the MP tape and the SP tape, wherein the two tapes are dispensed simultaneously when applying the sealing tape on a container.

Another embodiment relates to the indicating system wherein the service life of the system is varied or adjusted by changing one or more of the parameters selected from the group of: thickness of SP layer, quantity of MP, thickness of a permeable barrier layer if used, concentration of an activator and co-activator, concentration of an indicator and co-indicator, concentration of accelerator, concentration of a precursor if used and concentration of an additive.

Another embodiment relates to the indicating system wherein the service life and/or activation energy of the system is varied or adjusted by changing one or more of the parameters selected from the group of: nature of a SP, nature of MP, nature of an activator, nature of an indicator, nature of accelerator, nature of a permeable layer if used and nature of an additive.

Another embodiment of the invention relates to the indicating system which can monitor a material or a process. More preferred is the indicating system wherein the material to be monitored is water, water vapor, a chemical agent and the process to be monitored is time, temperature, time-temperature, freeze, thaw, humidity, doneness of food, microwave, pressure, radiation and sterilization including, for example, sterilization with steam, ethylene oxide, peroxides, plasmas of peroxides, formaldehyde and other aldehydes, dry heat and ionizing radiation.

In another embodiment of the invention relates to the indicating system which can be used to indicate the status of a perishable wherein the perishable is a food item, such as fresh, refrigerated, or frozen, vegetables, fruits, meats, fish, poultry, dairy products, bakery products, juices, pre-cooked foods, soft and alcoholic beverages, or a nonfood item, such as a pharmaceutical, vaccine, biological sample, such as sera, blood, or blood plasma, cosmetics, battery, reactive chemical compound or a biochemical product.

Another embodiment of the invention relates to the indicating system which can be used as, for example, for or on a safety sticker, self-timing retail sticker, biological industrial process monitor, self-expiring sticker to prevent re-use, security ID label, visitors badge, self-expiring parking tag, package and shipping label, wrist band, time indicating ticket for trains, buses, spot events, theaters etc., self-expiring pass for tours, emergency rooms, hospitals, museums, and other locations, race track pass, security label for screened luggage, purse, bag at airports to indicate that such items have been inspected, and at unmanned but video controlled entrances for visitors where a self-expiring visitor label is issued electronically. In addition, the indicating system can be used to indicate limited time consumer use for items that have been opened or in use and should be used within certain period, including but not limited to drinks, food items, health, personal and family care products. Also included are "gimmick" type applications, such as in toys, gimmick, messages, patterns, designs, gift cards, and greeting cards.

Another embodiment relates to the indicating system which can be used for or applied on medical products, food, biological waste, or to monitor the sterilization of such items.

Another embodiment of the invention relates to the process of using the indicating system of the invention on an object containing items to be processed or monitored.

Another embodiment of the invention relates to a process to monitor the status of medical products, food, or biological waste which comprises placing the indicating system on the packaging of such medical products, food, or biological waste.

Another embodiment relates to a process to monitor a perishable item by placing the indicating system on or near the perishable item wherein the perishable item is a food item, or a nonfood item. More particularly one can monitor the limited time consumer use for items that have been on or the item to be monitored, wherein the item is selected from the group of drinks, food items, health, personal and family care products.

Yet another embodiment relates to the indicating system for different classes of sterilization.

A MP in the form of vapor is required for migration of MP or activator. The MP should be capable of diffusing through solid SP. Solids which do not generate vapor may not be very effective MPs. However, a solid dissolved in another solvent/liquid or sublimeable solid (co-MP or accelerator) which can be carried along with the vapor of co-MP or accelerator can be effective and can be used.

The use of liquid MP is possible if it or its vapor does not significantly dissolve the nonporous SP.

If the composition resulting from the reaction of activator and indicator is volatile, diffusible, it can create a front/boundary. If the composition is less volatile, the boundary/border may not be created. Dyes which are one color at low concentration and another color(s) at higher concentration can create a ring or line at the front of the boundary.

In case of iron as indicator and chelate as activator, the complex formed can diffuse faster than chelate or be pushed by the vapor of chelate and similarly for other subliming compounds. One normally can expect that the boundary diffuses as it advances farther but in current invention the boundary can remain essentially of the same color or get stronger and darker and can also create a line, front or edge. If the product is a liquid or a volatile solid it is relatively easier for the activator to push the product at the front.

If the product of indicator and activator does not migrate, colored area will remain dark and if the product migrates it create a boarder/line. By adding an indicator in SP, the boundary remains essentially of the same nature, i.e., sharp. It is darker to begin with as it advances, proportionally more material is available from indicator in SP.

A coloring or indicator material which can be migrated by a MP, can be printed adjacent to MP, preferably printed on SP or on a substrate of SP. When MP reaches the coloring material, it will dissolve the coloring material and migrate towards the other end, a process similar to migration of an analyte in thin layer chromatography with a solvent.

The boundary of the indicating system is often sharp because even there is a gradient in concentration of activator, i.e., highest at the center and lowest at its edge but sufficient to give a dark color at the edges. Once full color is developed there cannot be more color intensification as the concentration of indicator is very low and cannot produce more color and hence the boundary is sharp and the circle is of almost uniformly solid colored. This process is equally applicable to all type SP including porous paper, SP containing dye/indicator and sharp melting activator/MP.

The MP, activator, indicator or the product of reactions, preferably should not substantially permeate through the substrates. A substrate for the device which is substantially impermeable to the components of the device is a preferred substrate.

Linearity of movement of the boundary is mainly depend upon supply of activator/MP, distance traveled, rate of generation of vapor of MP, shape of the device etc. For certain initial distance, the boundary moves linearly. As the amount of MP available decreases and the distance traveled increases, the movement of the boundary can slow down. Devices can be designed to make use of initial linear movement of the device.

Migration and linear movement of the boundary also depends on the nature of MP and also on the shape and design of SP. Less quantity of MP can only travel a shorter distance while large quantity can make the boundary move a longer distance and can be linear at the early stages of movement. The movement is linear for longer time if MP is directed to move in one direction (e.g., a narrow rectangular device) compared to in all direction in two dimensions, e.g., MP at the center of a circular SP.

The rate of movement of the boundary of the devices also depends on whether the diffusion is in all direction as in case of MP at the center of SP, directed at one location as in case of MP moving from periphery to center when MP coated at the periphery, two directions as in case of MP in the middle of strip or in one direction as in case of MP being at one end of a strip.

The speed of movement of the boundary also depends upon many other parameters such as nature and thickness of a SP, nature and concentration of MP, nature and concentration of an activator, nature and concentration of an indicator, nature and concentration of accelerator, nature of a permeable layer and other layer used and nature and concentration of an additive.

A solvatochromic composition which changes color when it comes in contact with a liquid or its vapor, e.g., some partially polymerized diacetylenes which change color from blue-to-red or vice versa with an activator or MP can be used as an indicator.

Activator and indicator both can be volatile or migratable. It is preferred that an activator MP is more volatile than indicator or additives in SP.

In another embodiment, the indicating system of the invention can also have at least one message which appears, disappears or blocked as a word or symbol on at least on one side of any layer or substrate, e.g., substrate of the indicator layer. The message can be in color. A message can be on or inside surfaces of any layer of the indicating system. In certain instances the system can contain at least two messages which do not start to become observable at the same time. An example is an indicator of the status or quality of an item when the indicating system is applied on or before the treatment of the item and a second message alone or in combination with the first indicating status or quality of the item after its treatment, such as, where the first message indicates un-doneness, freshness, usability, acceptability of the item and the second message alone or in combination with the first indicates doneness, spoilage, not usability and unacceptability of the item after a treatment or where the first message indicates non-sterile, non-usability, not-acceptability of the item and the second message alone or in combination with the first indicates doneness, sterile, usability and acceptability of the item after a treatment.

The surface of substrate contacting SP can be printed with indicator either continuously or selected areas, e.g, lines or numbers. When the vapor of activator reaches the indicator it will introduce a color change. If a colorless indicator is printed in form of a message, e.g., lines or number, they will become visible, invisible or disappear. The message could be in form of concentric circles with or without numbers, or can be one or two dimensional barcode. The barcode could be colored.

It is contemplated that any layer of the indicating system can contain a message or writing on either side of each layer. Printing on the indicating system of the invention, more especially on a substrate of the system, can be any process and material known in the art, including flexo, gravure, letter press, ink jet, laser, thermal and direct thermal printing and their inks.

It is not necessary to have an indicator in SP and activator in MP. Activator and indicator can be in MP. One can also add an indicator in MP and spot the mixture on SP or spot a mixture of indicator and activator (if one of them is also MP) on SP. In one experiment, colored iron complexes as indicators were added in chelates as MP and spotted on a layer of an adhesive, S85 as SP. S85 is a an acrylic pressure sensitive solvent based adhesive (S8510) supplied by Avery Dennison, Painesville, Ohio In another experiment, dyes were dissolved in sublimeable solids and spotted on S85 as SP. Yet in another experiment, mixtures of activators and indicators were spotted on S85 as SP.

The indicating system of the present invention can best be more fully described by reference to the figures. For simplicity and clarity of illustration, figures are not necessarily drawn to scale. The invention is further described below in conjunction with the figures.

FIG. 1 is cross sectional schematic presentations of moving boundary devices of (a) a known art, 1.1 and (b) a current invention 1.2. In the known art devices, the SP, 12 is a porous material, such as a paper and MP, 11 usually a liquid diffuses through the porous SP by wetting it and moves via wicking or capillary action. MP is a liquid containing a coloring material, such as a dye and hence requires sealing, 13 from all sides. Migration of the MP in known art devices is generally controlled by viscosity of MP while it is controlled by vapor pressure of MP, 1 in the current invention. Dyes are usually solid and hence need to be dissolved in a viscous liquid medium to use as MP in known art while sublimeable or readily diffusing solid dyes or activators are used in the current invention and vapor of the dyes migrate or diffuses through non-porous SP, 2 in the current devices. In order to fill the pores and wet the porous SP, relatively larger amount of MP is required for the known art devices. As the MP is a liquid, a complex design and a reservoir is required for the known art devices.

The SP, 2 in the current invention devices is non-porous, typically a highly amorphous layer of a polymer with or without additives such as plasticizers. SP of the current invention is in a glassy solid state, i.e., neither a liquid nor a crystalline solid. It has some properties of liquid but is not a liquid. MP, 1 in the current invention does not substantially wet SP. MP does not move as a liquid but its vapor diffuses through a non-porous SP. MP can be a solid or solid solution having some vapor pressure. As there are no pores to fill and MP does not need to wet the SP or fill the pores, relatively smaller amount of MP is required for the current invention. As the MP is usually a solid or semi-solid, the design of the current invention is simple, it does not need sealing the edges and made by coating or printing followed by lamination.

The results indicate that the quantity of MP required for the current invention is significantly lower, almost ten times lower than the known art devices. The linearity of movement of the boundary, at least for the early stages of movement of the boundary indicates that MP is not used up in significant quantity in wetting or dissolving SP. Many MPs have no or very little ability to dissolve or swell SP in a meaningful way and still they migrate through SP. In the devices of current invention, movement of MP is possible without the capillary action or significantly dissolving, swelling or wetting SP because the SP is significantly amorphous, a glassy state.

Lateral diffusion of vapor of a solid or liquid MP through a non-porous SP, often without significantly dissolving or wetting the SP is novel for an indicating device and is a preferred embodiment of this invention.

Known art devices, 2.1 based on vertical diffusion of an indicator or MP, 1 dissolved in a binder 3 diffuse through a permeable barrier, 6 is shown schematically in FIG. 2(a). In the known art devices of this type, 2.1 the diffusion of MP is in vertical direction (shown by an arrow) either through a binder 3 or through a barrier layer. The known art device can have an indicator layer 4 and substrates 5. In the devices of the current invention, 2.2 the diffusion of MP, 1 is not or very little in vertical direction but it is in lateral directions as shown by arrows in FIG. 2(b). The thickness of the permeable barrier, 6 in this type of known art devices is very thin, usually 20-100 microns. The permeable barrier in this type of known art devices have much higher Tg (glass transition temperature) and significantly less permeable to MP. The thickness of the SP, 2 which is highly permeable to MP of the current invention is also very thin, usually 20-100 microns but it is very wide or long in lateral directions as shown schematically in FIG. 2(b) and FIG. 4. The MP, 1 and SP, 2 are sandwiched between two substrates 5. The permeable barrier of the current invention has much lower Tg and is much softer. Use of non-porous and highly permeable SP in an indicating device is a preferred embodiment of this invention.

Figure 3:
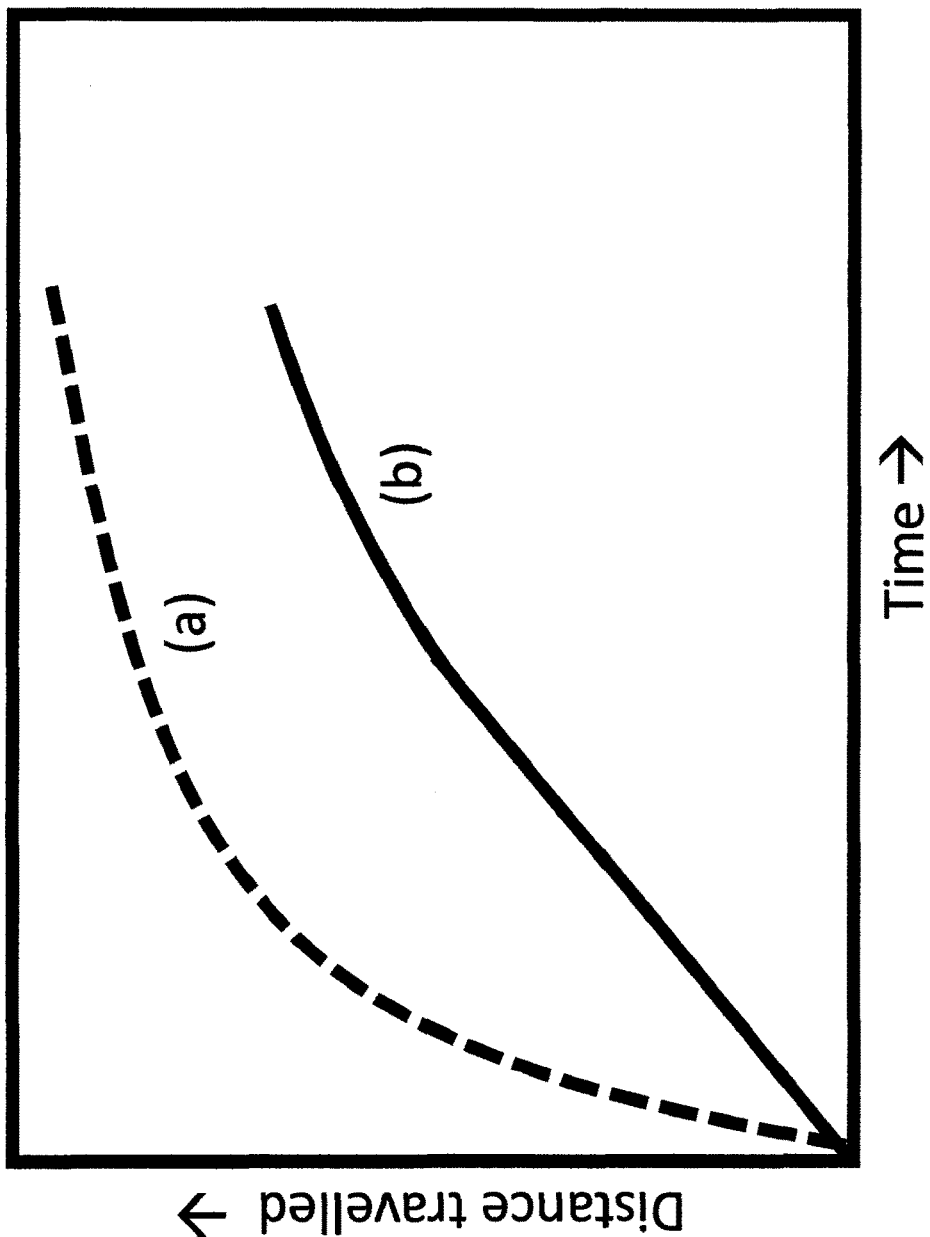
FIG. 3 is a schematic presentations of distance traveled by indicating devices of known art (*a*) and current invention (*b*).

FIG. 3 shows typical plots of movement of the boundary versus time after the activation of the known art and current devices. Typically, the movement of the boundary of the known art devices is asymptotic as shown schematically in FIG. 3(a), which is rapid in the beginning and gradually slowing down. This is mainly because MP is used up in wetting and filling voids of MP. The results (e.g., FIGS. 13-20) indicate that movement of the boundary in the current devices is almost linear initially and becomes asymptotic with time and distance traveled as shown schematically in FIG. 3(b). Linear or almost linear diffusion of a MP through a SP is novel for an indicating device and is a preferred embodiment of this invention. Results of comparison experiments on devices of the known art and current invention are shown in Example 1 and FIG. 13.

The moving boundary devices of known art use liquid or solution of a coloring material and hence they are complex and require special equipment to make them. The devices of the current inventions are essentially solid, easy to make with commercially available coating and laminating equipment. Making of moving boundary devices without using a liquid and essentially made of solid materials is novel for an indicating device and is a preferred embodiment of this invention.

The devices of the current art can be in form of two tapes, 4.1 as shown schematically in FIG. 4(a) for a circular device. The un-activated device (FIG. 4(a1)) is composed of two tapes. An activator tape comprises a small MP layer, 1 on a substrate, 5 and an indicator tape comprising a SP layer, 2, preferably a PSA layer on a substrate, 5. MP can be a sublimeable dye with or without a binder or additive. MP can contain or can be an activator and SP can contain an indicator. The device is activated, 4.2 as shown schematically in FIG. 4(a2) by applying the activator tape on to the indicator tape. When MP contacts SP, MP will start diffusing in and through SP. As the layer of SP is very thin, for example, ~50 microns thick and very permeable, the vertical diffusion of MP will occur within a very short period, e.g., within $1/1,000^{th}$ of useable life of the device. The MP then can only diffuse through SP in lateral directions.

FIG. 4(b) shows a top views of the device at different stages (b0, b1 and b2) of service life after its activation (device of FIG. 4(a)). When the device is activated by applying an activator tape on to the indicator tape, the device shows a small dot, b0 as shown in FIG. 4(b). The MP will start diffusing laterally and a circle is created and the boundary of the circle migrates outwards with time and temperature of annealing as shown schematically as FIGS. 4(b1) and 4(b2). This invention offers a simple way of making, e.g., by coating and activating (e.g., by lamination) of the device. As the boundary moves farther, it covers more area and hence it may slow down with time. Circular devices are especially suitable for application on the top of the caps of perishable containers, such as small vials.

MP can be spotted on SP followed by lamination with a substrate such as a plastic film.

The devices can be of any size and shape, e.g., from a few millimeter to a 1,000 cm² and circular, square, triangular, rectangular, spiral etc.

If MP is a coloring material, the movement of the boundary can be easily seen. The current invention is not limited to use color coloring materials as MP. The MP can be an activator and indicator. If MP is an activator, the indicator can be in SP and vice versa. A colorless MP (e.g., activator) will react with the indicator in SP and produce color. A large number of pairs of materials which produce coloring materials when they react can be used as activator and indicator for the devices. A common example of activator indicator pairs are an acid and a pH dye or a base and a pH dye.

It is not necessary to add an indicator in the SP layer. There are many ways to incorporate indicator composition in the device in addition to an indicator being in SP. The indicator, 4 can be in form of a layer below or above SP, 2 as shown schematically in FIG. 5. In this type of devices, 5.1 the activator will be in the MP or MP can be an activator. As MP or activator, 1 diffuses through SP, 2, it will react with indicator layer, 4 adjacent to it and introduce a color change and will create a boundary. The indicator can be in form of fine particles of metal in a SP or a layer of metal above or below SP and MP can be a material which reacts with the metal.

The devices shown here can have a barrier layer between the activator and indicator layer.

Figure 6:
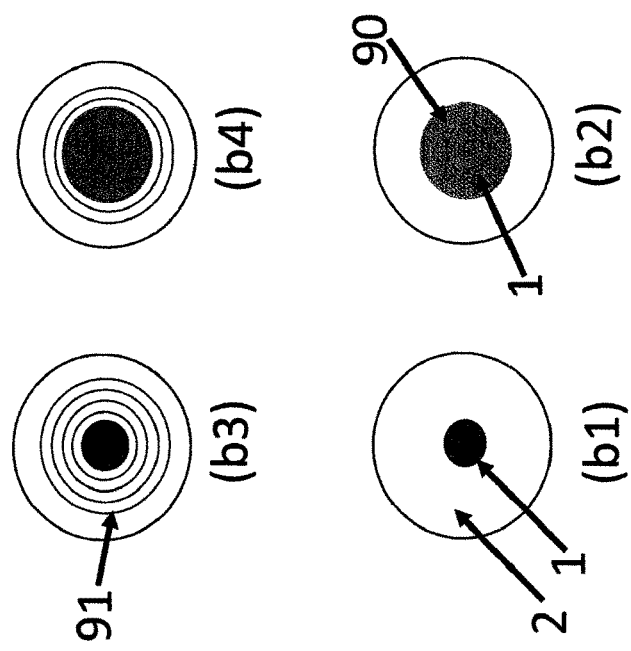
FIG. 6 is (*a*) a cross sectional schematic presentation of different modifications of the indicating device and (*b*) top views of some modifications.
Figure 6:
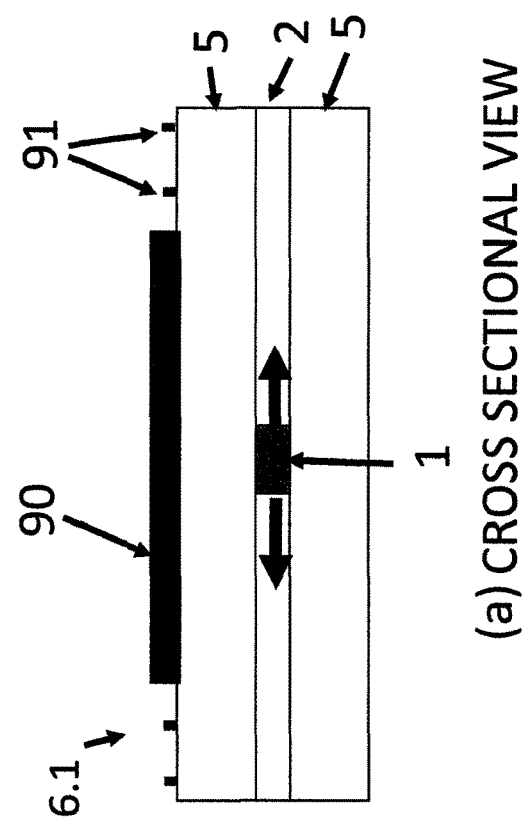

The indicating device can be modified, 6.1 in many ways. FIG. 6 is (a) cross sectional schematic presentation of different modifications of the indicating device and (b) top views of those modifications. In a simplest form, a dot of MP, 1 will grow into a circle as shown in FIG. 6(b1). The devices can have a mask, 90 to make movement of the boundary not visible for a certain period, referred here as induction period. Shape and size of the mask will depend upon the shape of the device and induction period required to make the boundary visible. The shape and size of the mask will depend on the shape of the device. A mask as shown in FIG. 6(b1) can be printed on one of the surfaces of substrates 5. The MP circle will become visible when it grows larger than the mask, thereby creating a go/no-go type device. Measurement of movement of the boundary can be done by printing a scale 91, numbers or concentric circles (as shown in FIG. 6(b3)) on any surface of the device. The device could have mask and circles as shown in FIG. 5(b4).

Figure 7:
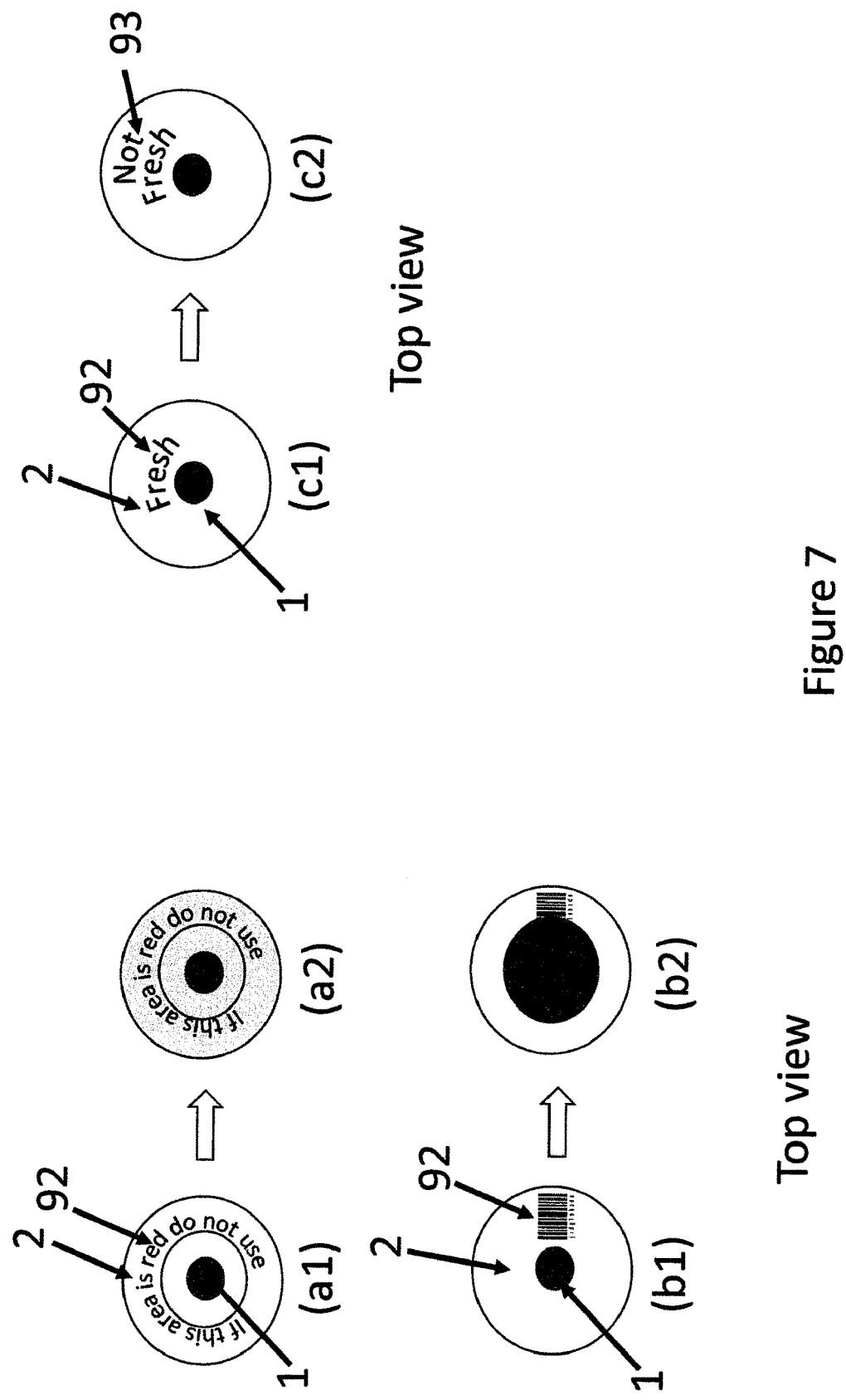
FIG. 7 shows top views of additional modifications of the indicating devices.

FIG. 7 shows top views of additional modifications of the indicating devices. It is relatively easy to modify the device for different applications just printing the messages, 92 on different layers of the devices as shown in FIG. 7. For example, a message, e.g., "if this area is red, do not use" as shown in FIG. 7(a1). When the MP spot grows out of the mask, the color of MP/dye will appear as shown in FIG. 7(a2). In order to make it machine readable, one can print a barcode as shown in FIG. 7(b1). When the MP dot, preferably of blue or black color grows, it will make a portion or whole barcode unreadable as shown in FIG. 7(b2). In another modification, a barcode can be made readable. Barcode could be two dimensional. One can print a message, e.g., "Fresh", 92 (as shown in FIG. 7(c1)) and "Not", 93 with a colorless indicator, e.g., a leuco dye. When the MP/activator grows and reaches the colorless dye, the message "Not" will become visible.

Figure 8:
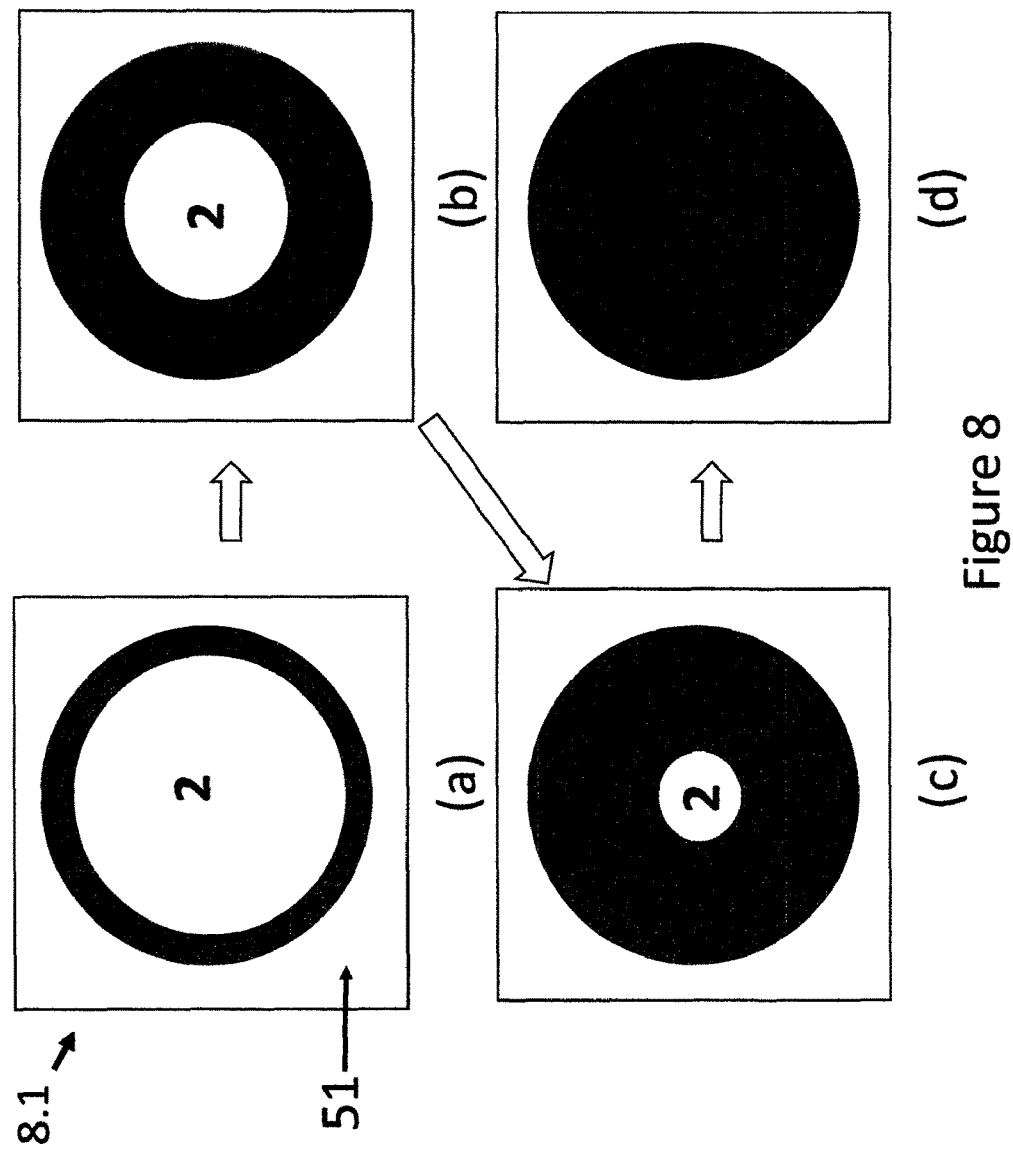
FIG. 8 shows top views of different stages of a circular indicating device wherein the MP is at the periphery and migrates towards the center of the device.

A MP can be applied at the periphery of the device, 8.1 as shown schematically in FIG. 8(a) for a circular device having a ring of MP. FIG. 8 shows top views of different stages of a circular indicating device wherein the MP is at the periphery and migrates towards the center of the device. The movement of the boundary will be towards the center if MP, 1 is in form of a ring as shown schematically in FIGS. 8(b), 8(c) and 8(d). In order to direct the movement of MP towards the center, this type of devices require sealing 51. In this case, the movement of the boundary can increase with time and temperature. As the boundary moves towards center, it has to cover lesser area and hence it can speed up with time. By controlling size and shape, it is possible to make movement of the boundary linear with time. This type of devices will require sealing at the edges/periphery. An MP at the periphery of a device, e.g., in form of a ring and the boundary moving towards center wherein the speed of movement of the boundary increasing with time, irrespective of nature and applications of the device is novel and is a preferred embodiment of this invention.

Figure 9:
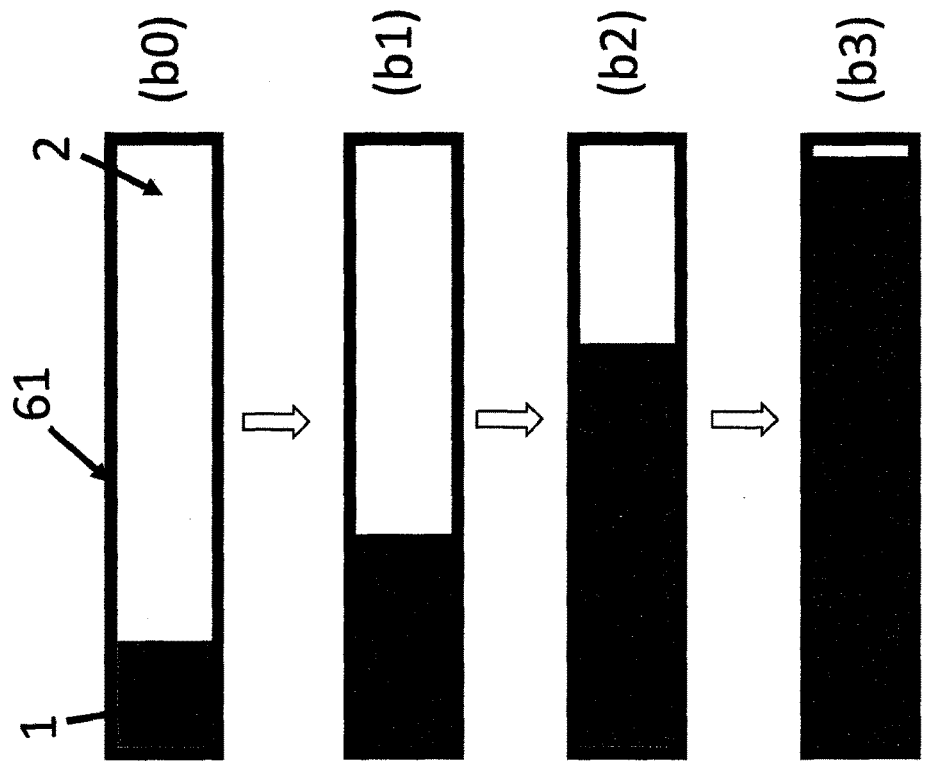
FIG. 9 shows a schematic presentations of a two tape strip type moving boundary device wherein migration of MP is directed in one direction, (*a*) cross sectional views of un-activated (*a*1), and activated (*a*2) devices and (*b*) top views of different stages of movement of the boundary of the activated device.
Figure 9:
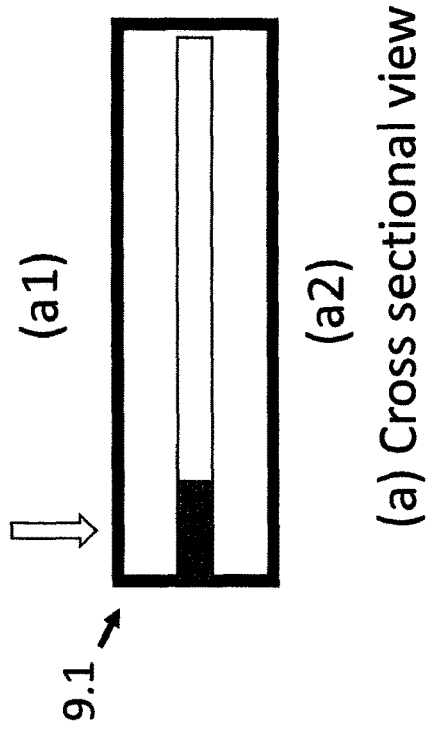

Another preferred design of the moving boundary device is rectangular as shown schematically in FIG. 9. FIG. 9 shows a schematic presentations of a two tape strip type moving boundary device wherein migration of MP is directed in one direction, (a) cross sectional views of 9.1 un-activated (a1), and 9.2 activated (a2) devices and (b) top views of different stages of movement of the boundary of the activated device. In case of the rectangular device, MP, 1 will be at one end of SP, 2 of the device as shown schematically in an un-activated device in FIG. 9(a) and activated and sealed at the edges, 61 in FIG. 9(b). Once activated, a boundary will be created and the boundary will move towards the other end as shown schematically in FIG. 9(b0-b3). The rectangular devices will require sealing, 61 at the edges. In case of sealed device in which movement of MP is restricted and directed in one direction, amount of MP required will be less and initial movement of the boundary can be linear with time.

Figure 10:
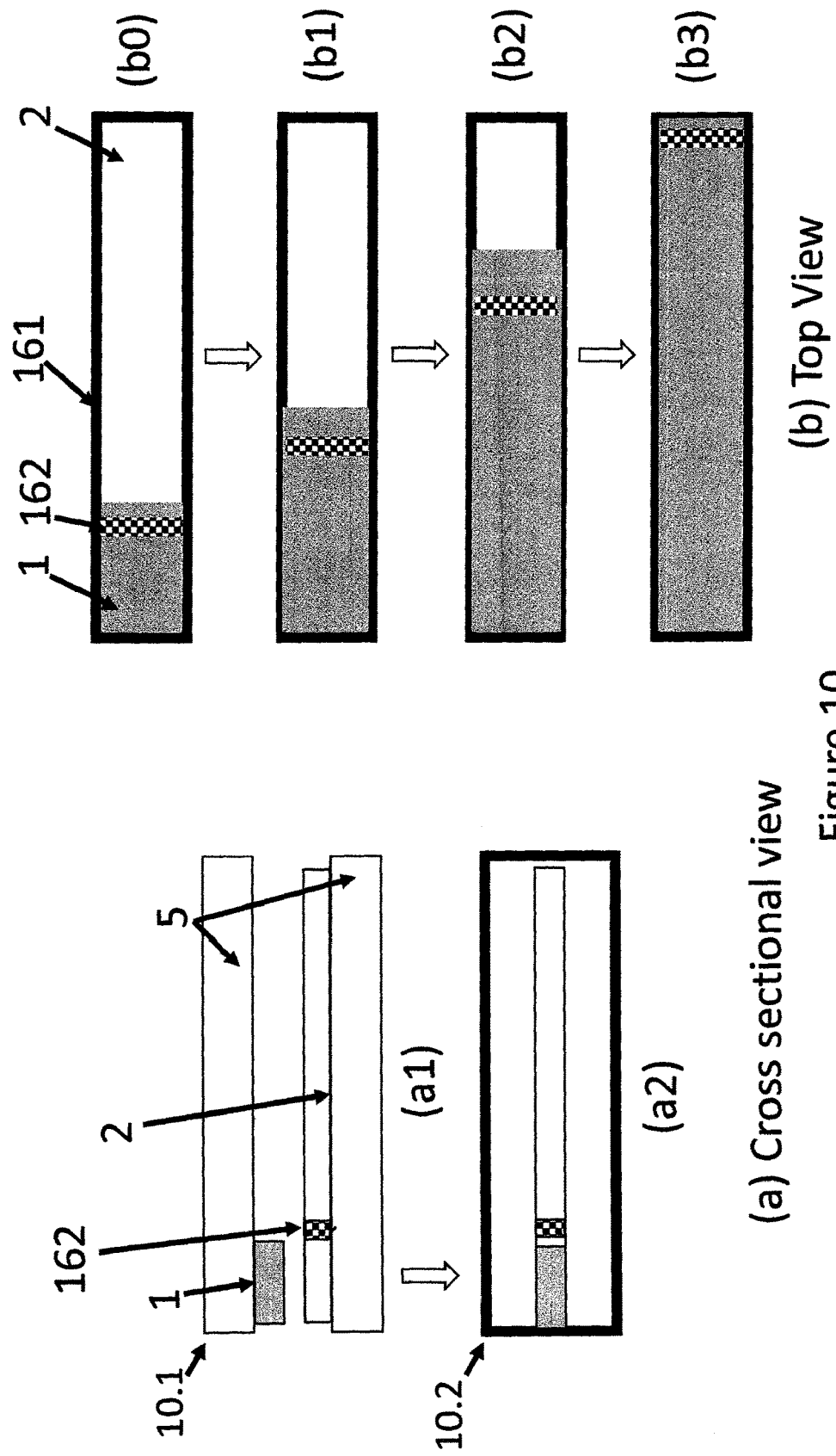
FIG. 10 shows a schematic presentations of a two tape strip type moving boundary device having a thin strip of indicator adjacent to MP wherein migration of MP is directed in one direction, (*a*) cross sectional views of un-activated (*a*1), and activated (*a*2) devices and (*b*) top views of different stages of movement of the indicator boundary of the activated device.

FIG. 10 shows a schematic presentations of a two tape strip type moving boundary device having line of indicator, 162 adjacent to MP, 1 wherein migration of MP, 1 is directed in one direction, 10(a) cross sectional views of un-activated, 10.1 and activated devices, 10.2 and 10(b) top views of different stages (FIG. 10b0-10b3) of movement of the boundary of the activated device. A coloring material such as a dye, 162 which can be migrated by a MP, 1 can be printed adjacent to MP, preferably printed on SP or on a substrate of SP. When MP reaches the coloring material, it will dissolve the coloring material and migrate towards the other end, a process similar to migration of an analyte in thin layer chromatography with a solvent. In the current devices, the movement of the dye is carried out by vapor of MP.

The device of FIGS. 9 and 10 will require sealing at the edges, can have more layers, can have scale or messages printed for monitoring movement of the boundary and other features of the circular devices.

Figure 11:
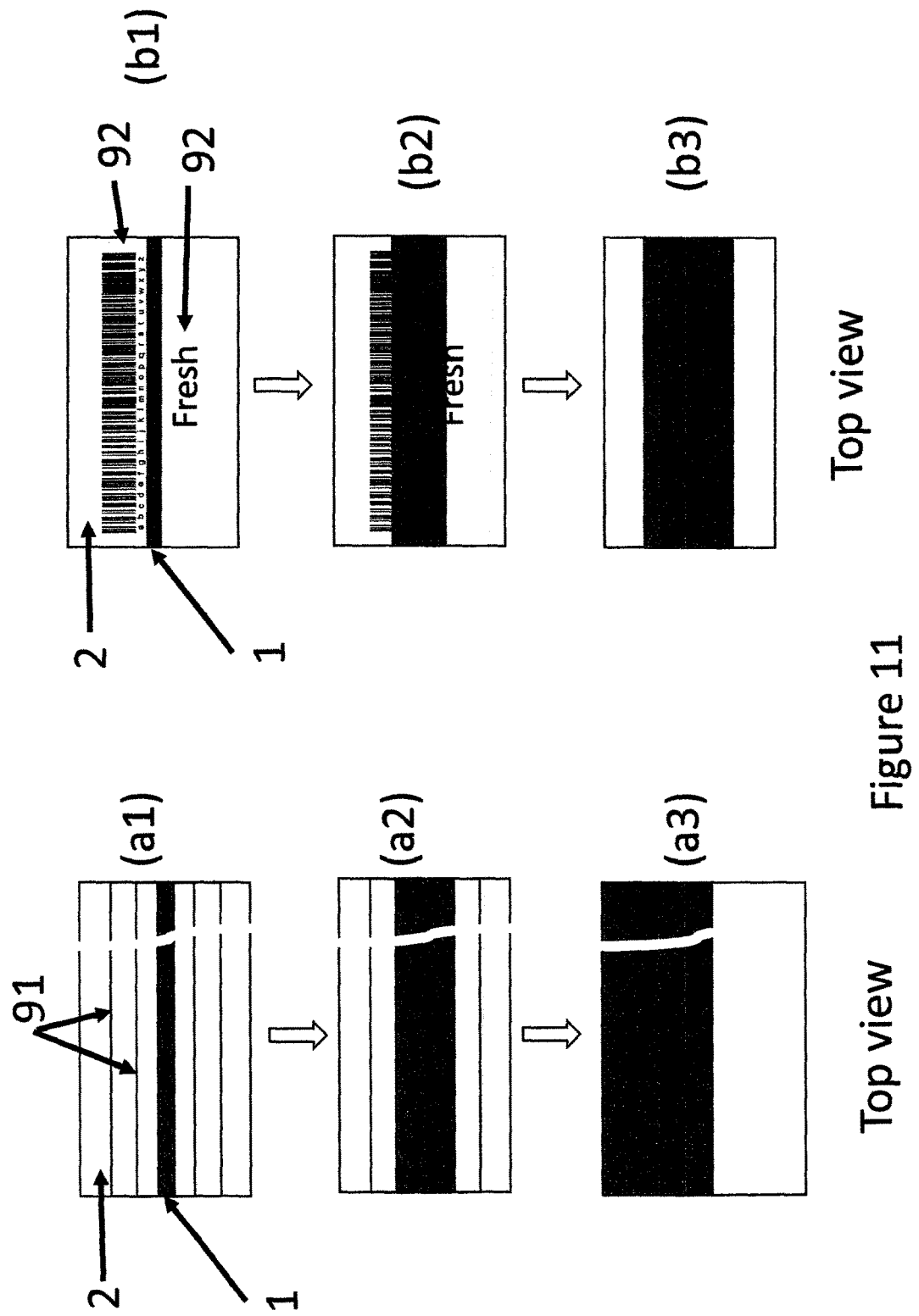
FIG. 11 shows top views of different stages of growth of MP in form of long narrow strip, a two tape packaging tape device having a thin MP layer of MP in the center of the SP layer.

The device can be inform of packaging tape which can be applied on a box of articles such as perishables for monitoring shelf life without opening the box. FIG. 11 shows different stages of growth of MP in form of long strip, a two tape packaging tape device having a thin MP layer of MP in the center of the SP layer. In the packing tape, the MP, 1 is in form of a line or a thin bar in the center of a substrate as shown in FIG. 11(a1). If the MP is linear instead of a circular spot, it can grow in form of strip as shown FIGS. 11(a2)-11(a3). The device can have means of reading the progress such as parallel lines, 91 as shown in FIGS. 11(a1)-11(a3), messages 92 such as Fresh or barcode as shown in FIG. 11(b1)-11(b3). As the boundary grows, the barcode will become invisible/non-readable and message such as Fresh will disappear (FIG. 11(b3).

Figure 12:
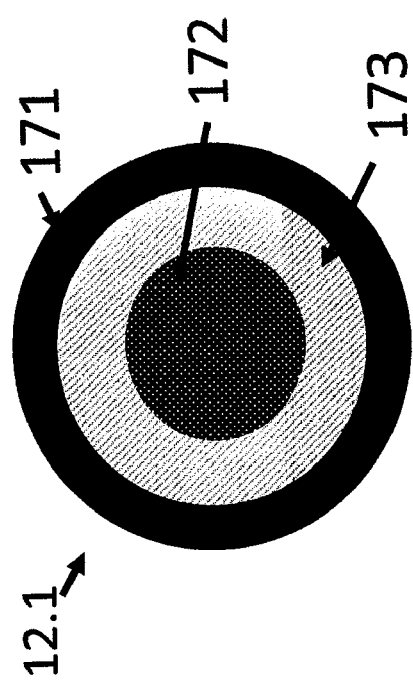
FIG. 12 shows a schematic presentation of a circular multisensor combination indicating device for temperature, time-temperature and freeze indicators.

FIG. 12 shows a schematic presentation of a circular multisensor combination indicating device 12.1 for temperature 171, time-temperature 173 and freeze indicator 172. This multisensor device can be a combination of two or more indicators chosen from time, temperature, time-temperature, freeze, thaw, humidity etc. with at least of them is a device of the current invention. The device can have any shape, e.g., square or rectangular, can be one device over the other or next two each other with or without a common substrate. They may undergo the same color change, e.g., blue-to-red, all changes to the same color from different colors or each can undergo a different color changes.

Figure 13:
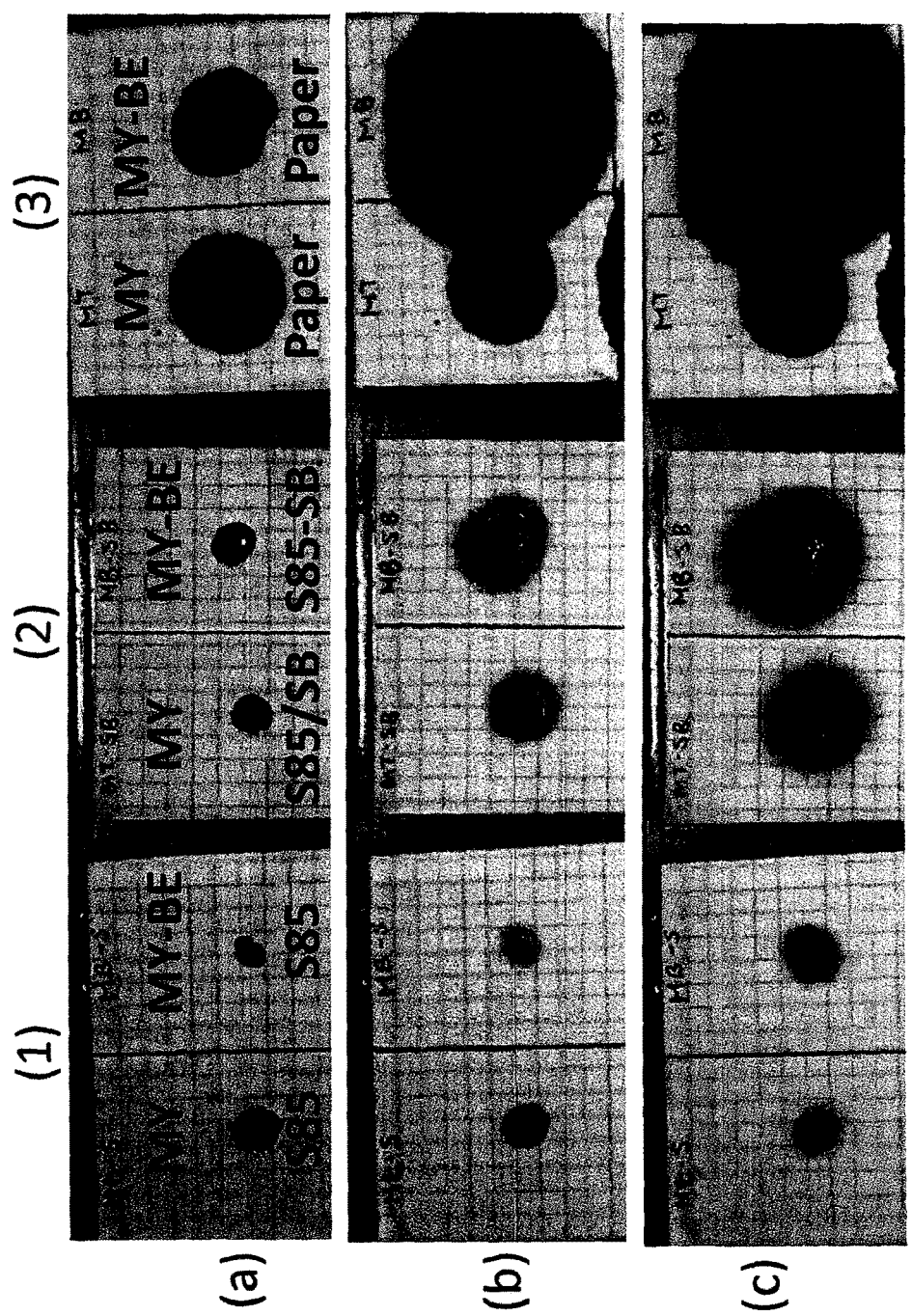
FIG. 13 shows growth of spots of methyl yellow dye with and without benzyl either as an accelerator, on three substrates (1) S85 PSA as a non-porous substrate, (2) S85 PSA with bis(2-ethylhexyl sebacate) as a non-porous plasticized substrate and (3) a copying paper as a porous substrate (a) a minute after spotting, (b) after 11 hrs at 60° C. and (c) after 4 days at 60° C.

FIG. 13 shows spots and their growth of dry methyl yellow (labeled as MY) dye (spotted from solution of tetrahydrofuran) and in benzyl ether (labeled as BE) as an accelerator for MP, on three substrates (1) S85 PSA as a non-porous substrate (labeled as S85), (2) S85 PSA with bis(2-ethylhexyl sebacate) as accelerator for SP), (labeled as SB) as a non-porous plasticized substrate and (3) a copying paper (HP office paper, 100 micron thick) (labeled as Paper) as a porous substrate. S85 is 58510 PSA (a pressure sensitive solvent based adhesive) supplied by Avery Dennison, Painesville, Ohio.

The spots were smaller on coatings S85 PSA and plasticized S85 as shown in FIGS. 13(a1 and a2). Almost as soon as a drop of tetrahydrofuran (THF) solution of methyl yellow was spotted on paper, it grew to the size shown in FIG. 13(a3). THF evaporated and a dry coating of methyl yellow was obtained on the paper.

The spot of methyl yellow in benzyl ether on paper grew within a minute to the size shown in FIG. 13(a3) and grew to the size shown in FIG. 13(b3) after 11 hrs at 60° C. and followed by very little growth as shown in FIG. 13(c3) even after 4 days at 60° C. Based on known art and as expected, the spot of methyl yellow in benzyl ether on paper grew rapidly in the beginning (FIG. 13b3) and then rapidly slowed down to essentially stopped growing (FIG. 13c3). The spot of dry methyl yellow did not grow on paper indicates that a fluid is essential for movement of the dye if the substrate is porous.

The spot of methyl yellow without benzyl ether (MY) as accelerator grew only slightly on S85 as shown in FIGS. 13(a1, b1 and c1). However, this spot continued to grow even larger with time and temperature (not shown here) but that on the paper did not grow. The spot of methyl yellow in benzyl ether (MY-BE) as accelerator grew on S85 as shown in FIGS. 13(a2, b2 and c2).

The spot of methyl yellow without benzyl ether as accelerator grew faster on plasticized S85 (FIG. 13c2) than unplasticized S85 (FIG. 13 c1). These spots continued to grow even larger with time and temperature at a faster rate than that on unplasticized S85. The spot of methyl yellow in benzyl ether as accelerator grew fastest on plasticized S85 as shown in FIG. 13(c2). This spot continued to grow even larger with time and temperature and grew largest and still most of dye was left in the center.

The spots of MP (methyl yellow) did not grow or grew rapidly in the beginning and then stop growing on the porous substrate, paper (FIG. 13-3) indicates that porous substrate such as paper cannot be used to make TTI for the current system. The spots of MP on the non-porous substrate, adhesive grew with time and temperature (FIGS. 13-1 and 13-2) indicates that a non-porous substrate such as a layer of adhesive can be used to make TTI for the current system. The above results of FIG. 13 clear differentiate known art from current invention and show the novelty of the current invention. Additionally, we demonstrated that an accelerator (e.g., benzyl ether) in MP and/or an accelerator bis(2-ethylhexyl sebacate) can increase the rate of the reaction.

Devices shown schematically in FIGS. 4-11 were made and we studied effect of many variables. FIG. 14(a) shows different stages of diffusion of methyl yellow dye with time at 60° C. in a 50 micron thick layer of S85 (plasticized with bis (2-ethylhexyl sebacate). The dye diffused through SP and created a circle which grew with time and temperature. The spot of the dyes was created by pouring its solution in tetrahydrofuran (THF). The solvent evaporated leaving solid powder of the dye attached to the adhesive.

FIG. 14(b) shows different stages of diffusion of Sudan II dye with time at 60° C. in a 25 micron thick layer of an acrylic hot melt adhesive (a polyester film coated with an acrylic hot melt adhesive supplied by Transilwrap, Bethlehem, Pa.). The dye diffused through SP and created a circle which grew with time and temperature. The spot of the dyes was created by pouring its solution in tetrahydrofuran (THF). The solvent evaporated leaving solid powder of the dye attached to the adhesive. As can be seen from the FIG. 14b, the spot grew larger with time. When the SP is an acrylic hot melt adhesive the growth of the spot was lower than that of PSA.

Figure 15:
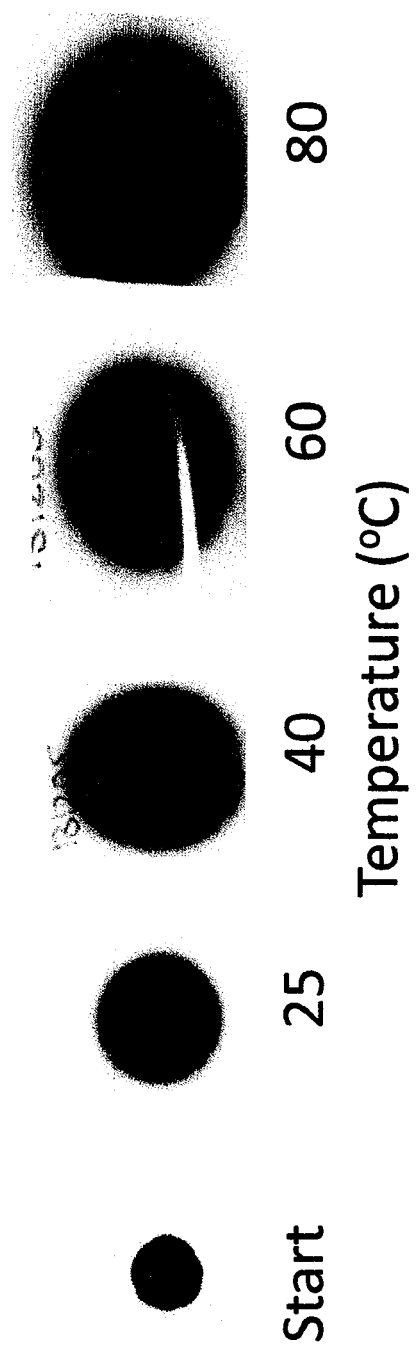
FIG. 15 shows different stages of growth of a spot of methyl yellow in a 50 micron thick layer of S85 PSA after 11 days at different temperatures (° C.).
Figure 16:
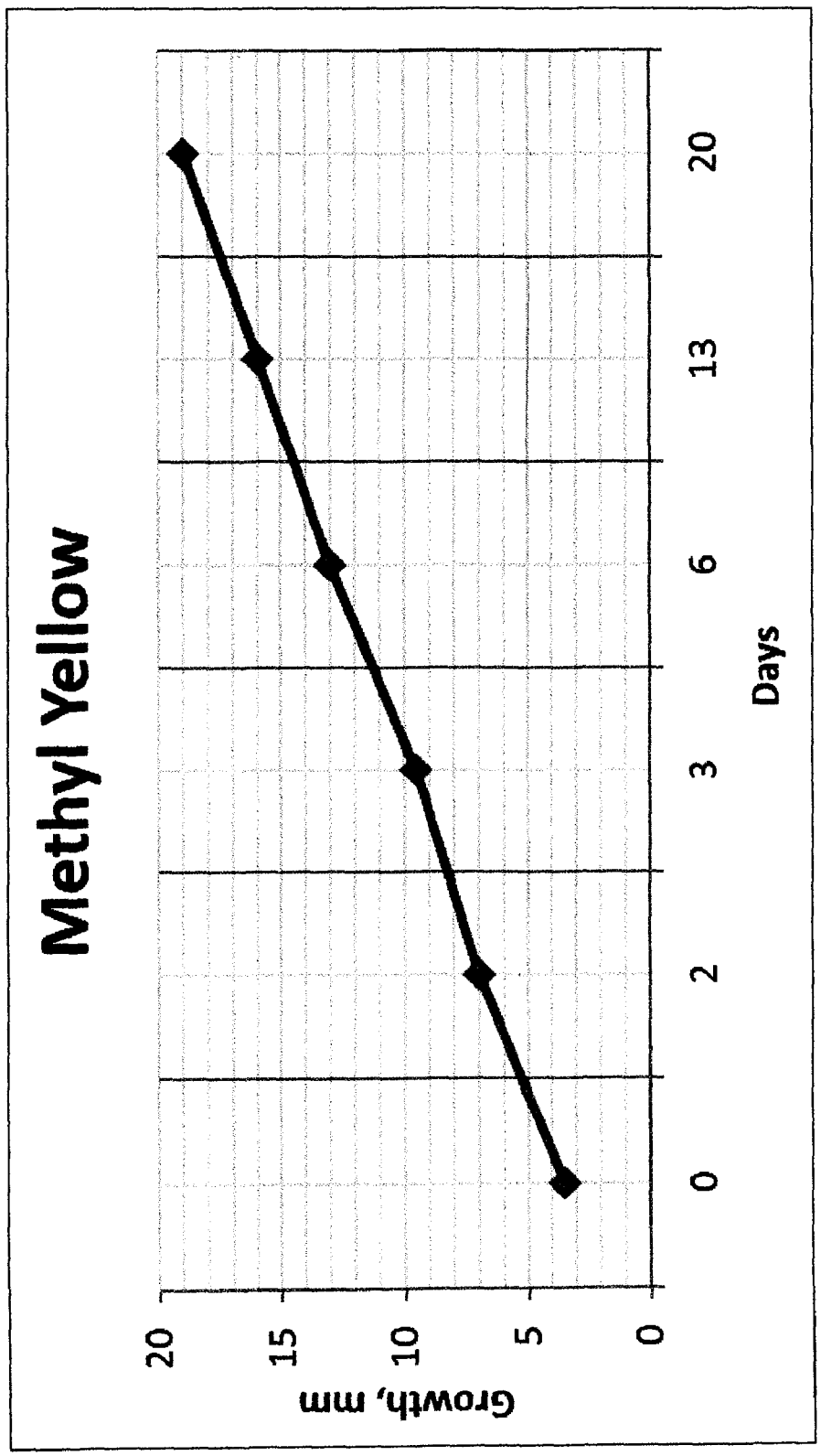
FIG. 16 shows a plot of size of a methyl yellow spot in S85 PSA layer with time.

FIG. 15 shows different stages of growth of a spot of methyl yellow dye in a 50 micron thick layer S8510 PSA (a pressure sensitive solvent based adhesive supplied by Avery Dennison, Painesville, Ohio) after 11 days at different temperatures. As can be seen from the FIG. 15, higher the temperature faster the growth of the spot. The spot initially grew linearly as shown in FIG. 16.

Figure 17:
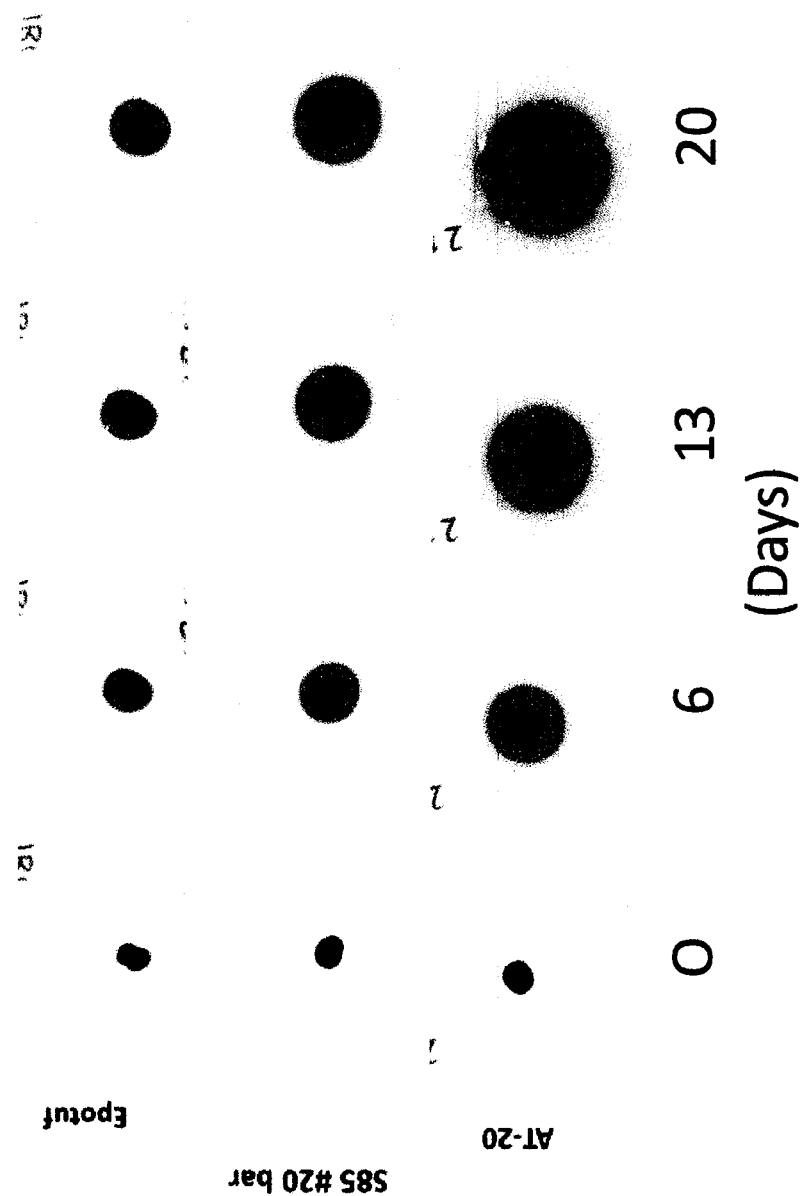
FIG. 17 shows effect of nature of pressure sensitive adhesive SP on growth of a spot of Sudan II at 80° C.

In addition to time and temperature, the growth of the spot of the boundary depends upon many other factors, such as nature of the SP (as shown in FIG. 17), MP, indicator, activator, additives etc. FIG. 17 shows effect of nature of pressure sensitive adhesive as SP on growth of a spot of Sudan II at 80° C. The growth in Epotuf (an epoxy PSA of Reichhold, Durham N.C.) PSA was slowest and that of AT20 (an acrylic resin of Avery Dennison, New York, N.Y.) was the fastest.

Figure 18:
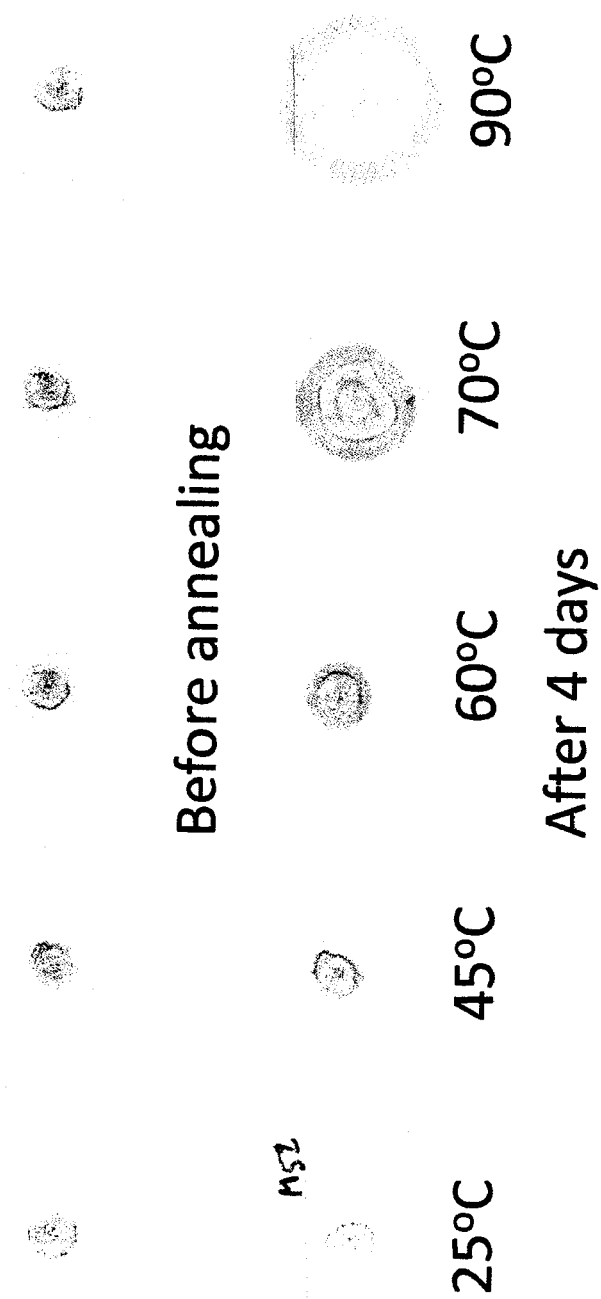
FIG. 18 shows different stages of growth of spots of diaminodecane as an activator and a universal indicator as an indicator in a 50 micron thick S85 PSA layer before (a), and after 18 hours (b) at different temperatures (° C.).
Figure 19:
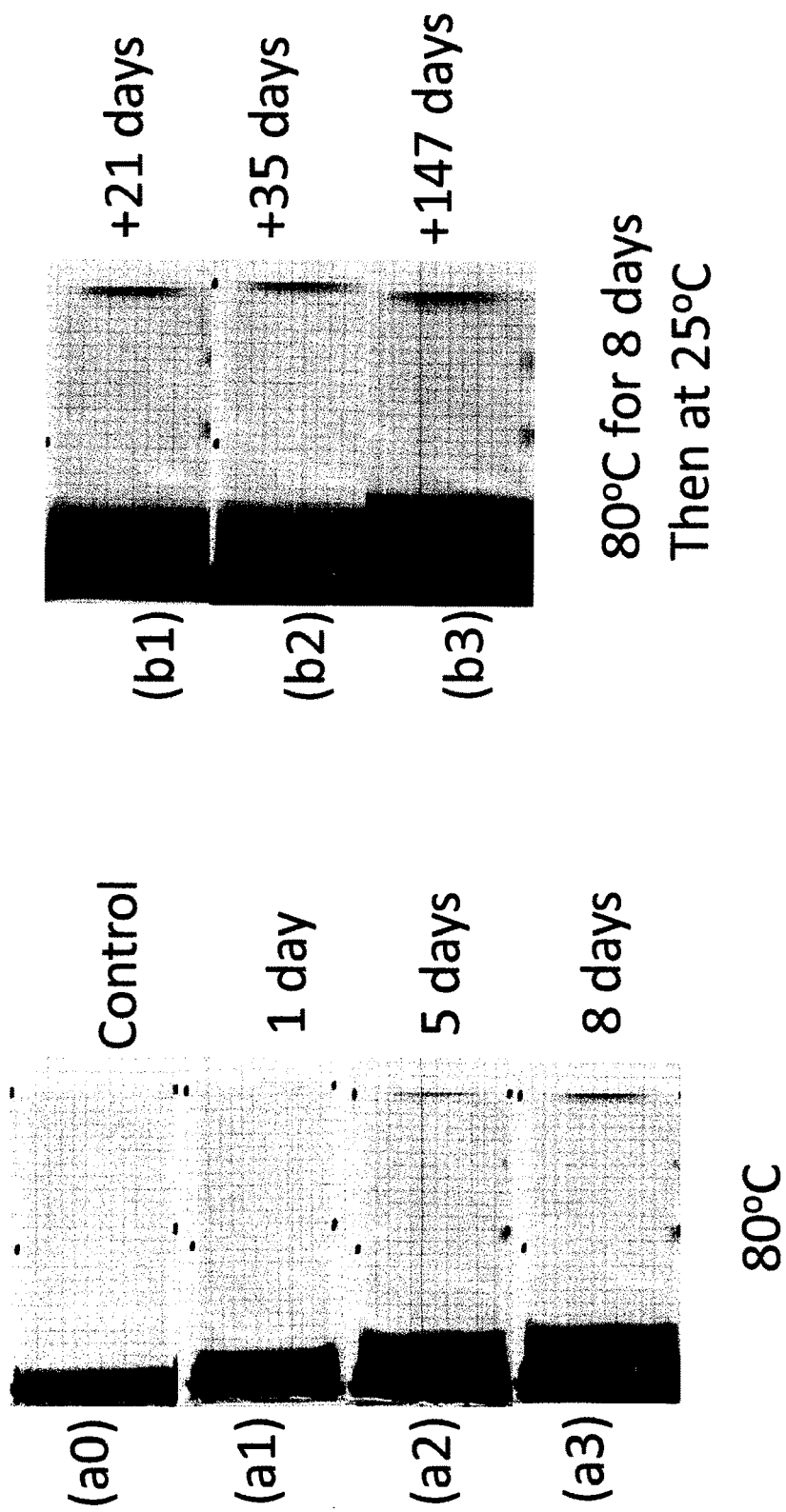
FIG. 19 shows movement of a moving boundary of a strip device of present invention.

FIG. 18 shows different stages of growth of a spot of diaminodecane as an activator and a universal indicator pH dyes as an indicator in a 50 micron thick layer S85 PSA after 18 hours at different temperatures (° C.). The universal indicator was prepared by dissolving 0.50 g phenolphthalein, 0.30 bromothymol blue, 0.03 g thymol blue sodium salt, 0.06 g methyl red in 20 g THF. As can be seen from the FIG. 18, when MP is not a coloring material, colored circle or boundary can be created by using an activator-indicator pairs which produce colored material. The melting point of diaminodecane was 70° C. (literature melting point is 75° C. but the diaminodecane we used was a technical grade material and melting point was 70° C. because of the impurities). As diaminodecane has very little vapor pressure below 70° C., it did not migrate below 70° C. However, in molten/liquid form, it can diffuse through SP and circles were created above 70° C. FIG. 18 is an example of the threshold time-temperature indicator. Though we used an amine as an activator one can use an acid as well. We also made a number of devices similar to that shown in FIG. 18, using a number of other indicator-activator pairs, including chelates as activator and metal salts, e.g., ferric acetate and organometallic compounds, e.g., potassium ferricyanide as indicator. An example of selective activator-indicator pair and a rectangular strip type moving boundary TTI is shown in FIG. 19.

Wicking type indicating devices are usually rectangular. The devices of current invention can be of essentially any shape. For example, one can create rectangular indicating devices by placing MP at one end of a rectangular shape SP rather than at the center, as shown in FIG. 19. A substrate was coated with a PSA containing an iron compound, nitrosonaphthol (NN) as MP was coated at one end of the SP rectangular strip of the SP and sealed from at all edges as shown in FIG. 19(a0). The device is sealed from all edges, NN moves only in one direction as shown in FIGS. 19(a1-a3) at 80° C. and 19b1-19b3 at room temperature thereafter. As can be seen, the boundary moved towards the other end with time and temperature.

Figure 20:
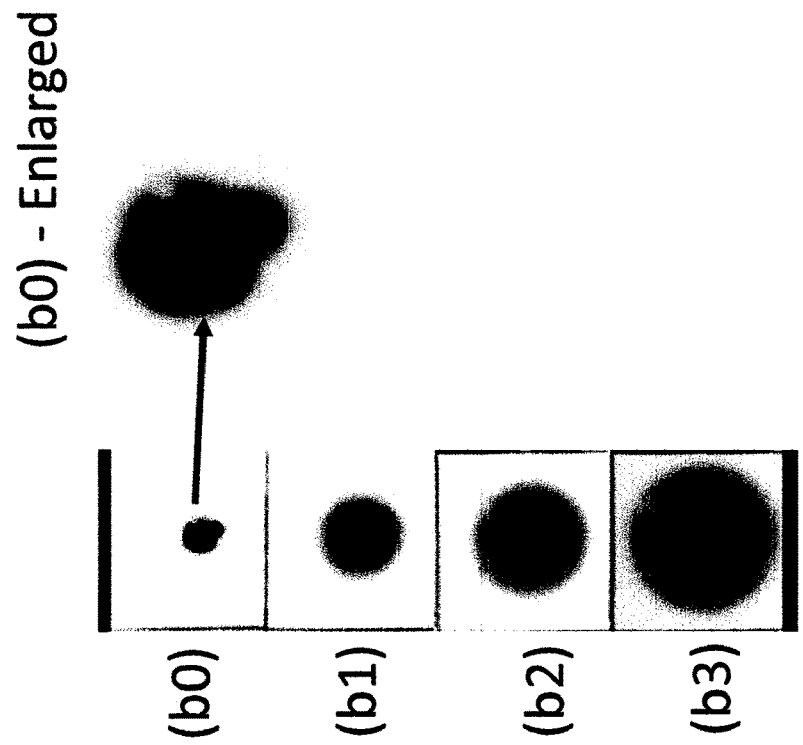
FIG. 20 show two irregular shapes MP spots becoming nearly perfect circles.
Figure 20:
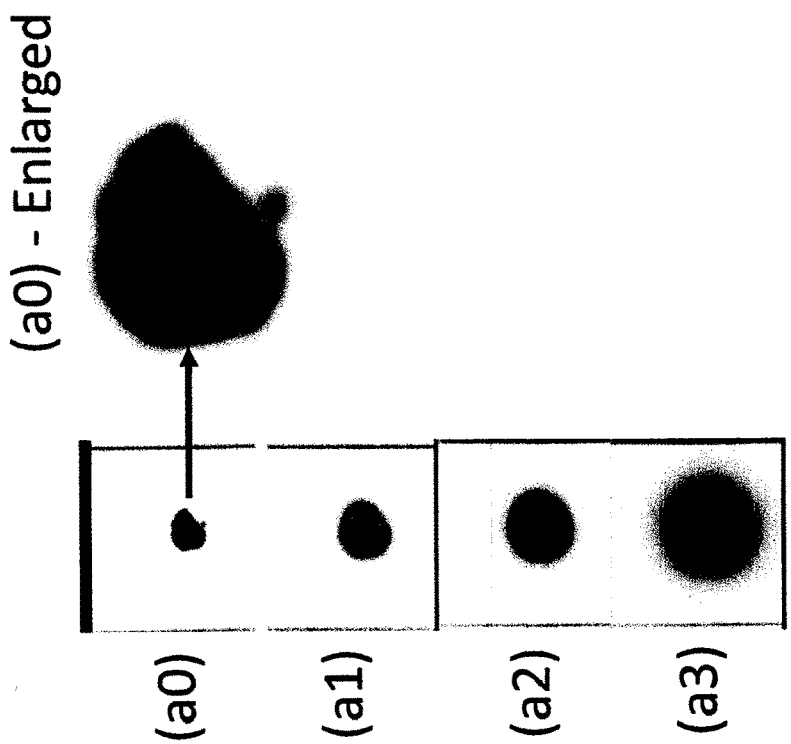

FIG. 20 shows a uniqueness of the current invention. Even if a mistake is made in printing shape of MP, MP corrects itself as it progresses and becomes nearly perfect circle as exemplified in FIG. 20. A half circle, triangular, square, star shaped and rough edged MP become nearly perfect circle at the end. As shown in the enlarge image of MP in FIGS. 20(a0) and 20(b0), a half circle (FIG. 20(a0)) and two circles (one large and one small in FIG. 20(b0)), ultimately become one nearly perfect circle (FIGS. 20(a3) and 20(b3)) with time and temperature. This irregular shape of MP becoming nearly uniform circle, i.e., self-shape-correcting phenomenon/device is unique and novel for an indicating device and is a preferred embodiment of this invention.

Figure 21:
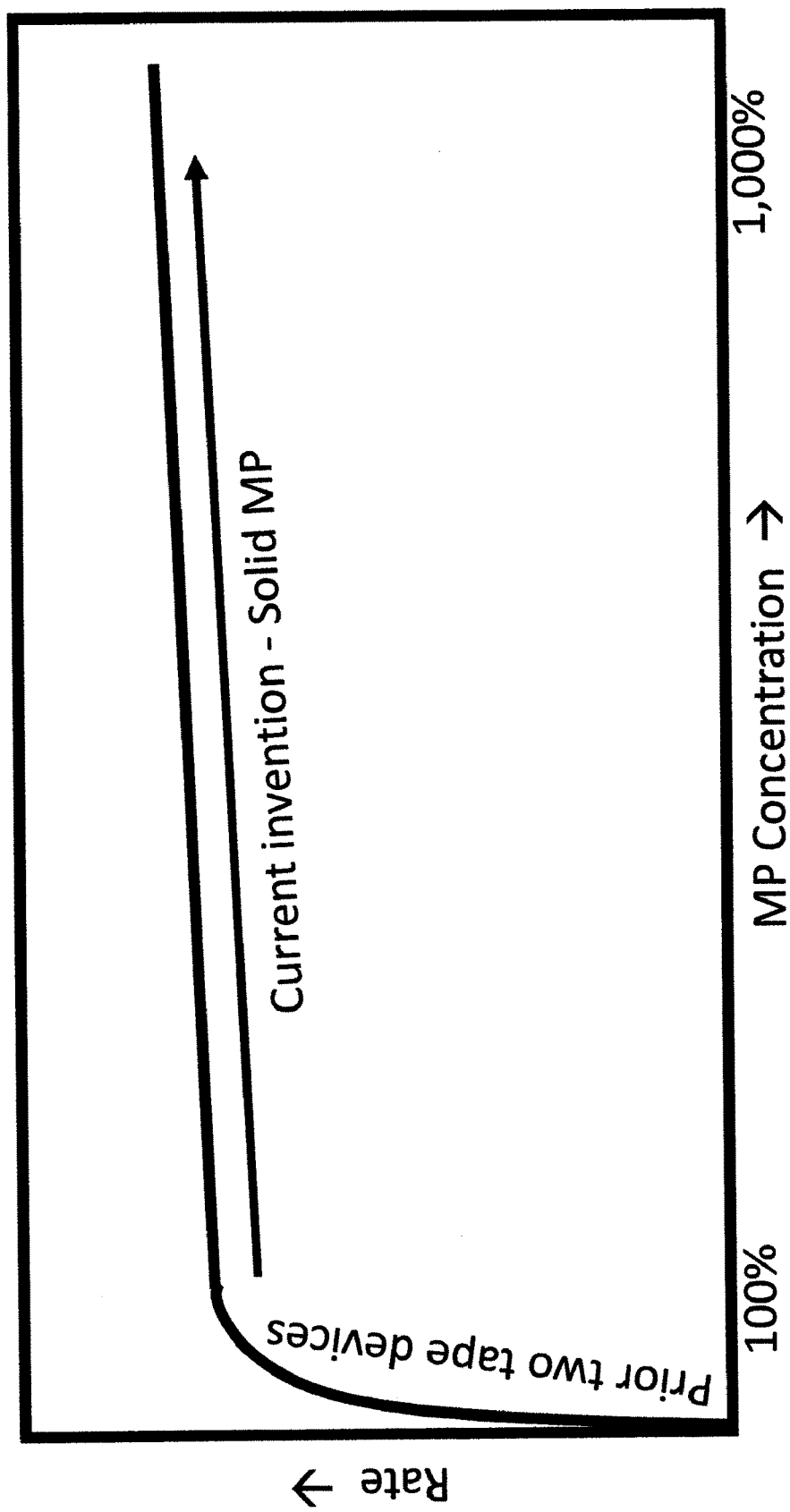
FIG. 21 shows a schematic presentation of a plot of rate of diffusion of MP with concentration or weight of MP.

It was also discovered that the concentration of MP, in this case amount or thickness of MP has very little effect of time and temperature on indicating device of instant invention. As shown in Example 11 and Table 2, the amount of MP has very little effect on the rate of growth of MP spot. FIG. 21 explains why there is a little effect of concentration/amount of MP on the rate of movement of the boundary. FIG. 21 is a schematic presentation of rate of growth of the circle vs concentration of MP. Typical concentration of an activator/MP in its binder in a typical two tape device of FIG. 2(a) where the diffusion of MP is vertical, is usually less 10% and the time can be varied from hours to months by varying the concentration 2-10% the activator. Indicating devices of FIG. 2(a) are highly sensitive to concentration of MP. In the case of the current horizontal diffusion devices, the rate increases initially as the concentration of MP increases up to 100%. The 100% concentration means essentially solid MP or no dilution. Once the MP is solid or neat (i.e., no dilution) then there is only a slight increase in the rate. After 100% concentration, one can only increase the quantity of MP and hence there is very little effect of concentration or quantity of MP, once MP is nearly 100%. Very little effect of concentration or quantity of MP on the reaction rate is unique and novel for an indicating device and is a preferred embodiment of this invention.

Figure 22:
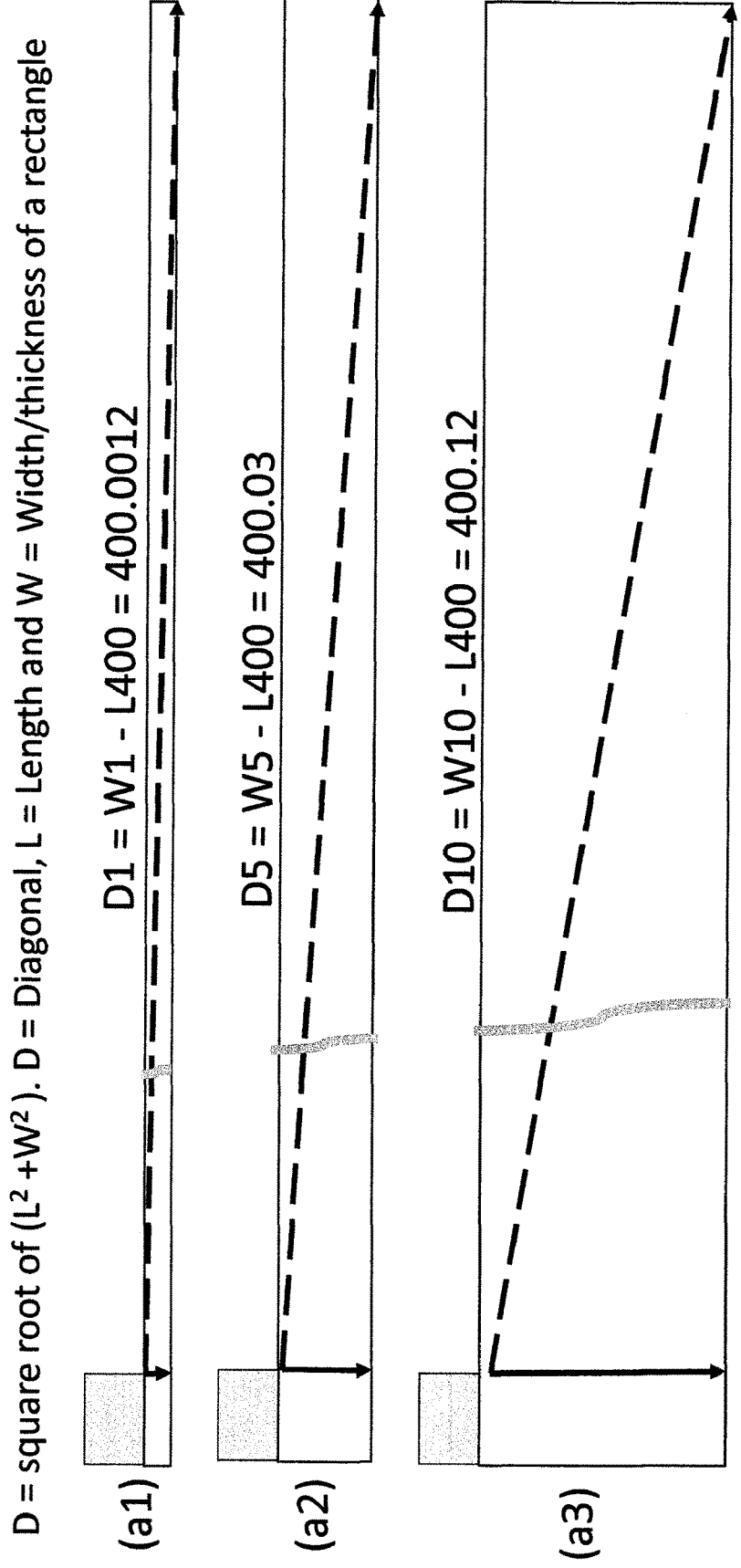
FIG. 22 shows a schematic presentation of vertical and lateral diffusion of MP in the indicating devices of different thicknesses.

It was further discovered that the thickness of SP also has very little effect of time and temperature on indicating device of instant invention. As shown in Example 15, the thickness of SP has very little effect on the rate of growth of MP spot. FIG. 22 explains why there is a little effect of thickness of SP on the rate of movement of the boundary. FIG. 22 shows a schematic presentation of the indicating devices having different thicknesses of MP and distance to be traveled by MP. The maximum distance MP has to travel is diagonally the end of the device. The ratio of length or radius of the device to that of the thickness of the SP layer is very high, usually higher than 100. For example, for a typical device having 1, 5 and 10 mil (25, 125, and 250 micron) thick SP layer and 1 cm (400 mil or 10,000 microns) long, the diagonal or the maximum distant the MP has to travel is 400.001 mil for 1 mil thick SP, 400.03 mil for 5 mil SP and 400.12 mil for 10 mil SP, i.e., insignificant difference. Example 15 demonstrate and FIG. 22 explains that the thickness of SP has almost negligible effect on time required for the boundary to travel a reasonable distance of about 1 cm. Typically, two tape indicating devices of FIG. 2(a) where the diffusion of MP is vertical, are usually highly sensitive to the thickness of the SP or barrier layer. Very little effect of thickness of SP layer on the distance traveled by MP is unique and novel for an indicating device and is a preferred embodiment of this invention.

The current indicating devices on the first glance may appear to be somewhat similar to that of the known art moving boundaries and other similar indicating devices and processes. However, the current devices are not only significantly different but very innovative, novel, unique and differ in many ways from the devices of the known art and hence offer many of the desired properties and many advantages over the known art devices as shown herein. Some of the unique and novel features of the current devices are not possible with the known art devices. The major difference between the known art and current invention are outlined in Table 1.

TABLE 1

Comparison of known art moving boundary devices based on diffusion of a liquid MP through a porous SP with that of current invention based on diffusion of a MP through a non-porous SP.

|  | KNOWN ART | THIS INVENTION |
| --- | --- | --- |
| Nature of MP | Viscous liquid | Mainly solid |
| Use of solid MP | Does not work | Solid MP preferred & used |
| Nature of SP | Porous | Non-porous |
| State of SP | Solid/Non-glassy | Solid/Semi-solid/amorphous |
| Typical SP | Paper | Adhesive |
| Device design | Complex | Simple - thin sticker or strip |
| Migration process | Absorption based diffusion | Non-absorptive diffusion |
| Mechanism | Wicking/capillary action | Permeation |
| Kinetics | Asymptotic | Initially linear |
| Effect of gravity | Slight | None |
| Speed of the boundary | Fast | Sufficiently slow |
| Service life at 25° C. | Hours to days | Hours to years |
| Activation energy | Difficult to vary | Easy to vary |
| Size | Limited/restricted | Essentially unlimited |
| Cost | High | Low |
| Manufacturing | Complex | Simple |
| Activation of devices | Complex | Simple, lamination |

The major differences are, for example, (1) MP of the known art devices must be liquid while that of current invention can be solid. As shown in Example 1, solid MP cannot be used for the known art devices, (2) SP of the known art devices are porous while that of current invention are non-porous and hence quantity of MP required is less, (3) The diffusion of liquid MP in the known art devices occurs due to the wicking/capillary action and liquid MP fills the pores as it advances while the solid or liquid MP of the current invention permeates through a non-porous polymeric layer, (4) Movement of the boundary is asymptotic with known art devices while it is linear initially with the devices of the current invention, and (5) The known art devices are complex to manufacture, need to be pre-assembled or require special activation while that the devices of current invention can be manufactured by lamination and hence easy to activate when desired. Example 1 and FIG. 13 show results of control and comparison experiments of known art with a fluid MP and current invention with a solid MP. The current device can be very thin and small and hence can be applied even on a small cap of a vial.

A two tape devices of the current invention can be activated by applying the activator tape or MP tape on the indicator tape or SP tape. The device can be applied on to an object by removing the release liner. In order to make the indicating devices activatable on demand, one can use microencapsulated activator and/or indicator. The device can be created by applying a layer of microencapsulated MP which can be ruptured e.g., by application of heat or pressure.

In order to store a tape having a PSA as the top layer may have a release layer and/or release liner (which is not shown in Figures), so it can wound on itself and stored until used. In order to minimize diffusion of MP of the activator tape or sticking to the other side of the substrate during the storage, the spot or bar of MP can be coated with a permeable but not sticky polymer layer. The release layer could be composed of a nonstick material which does not bond or bonds very weakly with a PSA. The release materials include silicone, fluoropolymers such polytetrafluoroethylene, highly cross-linked resins, and oils. The preferred release material is a silicone and a fluoro-polymer.

The indicating devices of current invention can have many additional layers. These layers can have any color, shape, thickness, size and nature as desired. The position of these and other optional layers relative to one another can often be changed and can often be interchanged. Most of these layers could be whole, partial or discontinuous. Some of these layers could be in form of a pattern, message or image. These optional layers, such as top message layer, activation layer, tamper indicating layer and mask layers and are preferred embodiments of this invention. These optional layers may be composed of a microencapsulated material, such as an activator.

The devices can be in form of wrist band or foldable modifications. The activator and indicator tapes can be attached or directly coated/applied at different locations and sides on a substrate which is in form of a strip or open band. A band (e.g., wrist band) can also be created by jointing activator and activator tapes at the ends. They can be joined by many sealing methods, such as with an adhesive or by ultrasonic welding.

A tamper indicating device can also be made by using the substrates made from a destructible/breakable plastic, such as polystyrene, polyvinyl chloride (PVC) and cellulose acetate. These and other tamper indicating materials and processes described in US Patent Application No. 20120244623.

The current technology offers an opportunity to make sealing tape and label TTI. Activator and indicator tapes dispensed from a double-tape/two-tape dispenser and applied on a perishable box will seals the box and will also monitor shelf life. The person opening the box will easily notice whether the perishable inside the box is of good quality or shelf life expired.

Tape dispensers are known in the art. Typically, a tape dispenser is comprised of a system capable of retaining and dispensing a single roll of tape. The current two-tape dispenser is a dispenser for holding two rolls (activator and indicator rolls), mechanism for their lamination/activation and cutting laminated/activated tape of desired length. A box can be sealed with an indicator tape in form a large label and activated with an activator tape.

The packaging tape can be pre-activated by applying an activator tape on to the indicator tape, stored cold to stop the reaction till needed.

The sealing tapes and labels could have the many of those features of other indicating device described in this application, for example, other basic and optional layers to get moving boundary, barcodes, numbers, patterns, colors, images and messages.

The activated sealing tape could be applied only on the top closers/flaps or whole box and even crossing the previously applied activated sealing tape.

The size of the indicating devices can be as small as a few square millimeters to several centimeters or larger. The thickness of the device typically can be from a thousandth of a centimeter to a millimeter, or thicker, if desired.

The device can also be in form of a very long tape which can be wrapped on any object including boxes containing food packages or cut into small pieces and applied on individual object. The long tape indicating device can also be applied on closer of a perishable container so it can be easily noticed and shelf life can be monitored.

The device can also be in form of large labels, stickers and alike.

As the indicator layer of the current device is environmentally highly stable, the indicator tape can be pre-applied on any object including perishable containers and activated when desired, e.g., when container is filled with a perishable.

In order to avoid effect of undesirable, adverse effects of ambient conditions, such as humidity, oxygen, carbon dioxide and UV light, one may select materials for the devices which are either not affected by them or protect them. If the materials are humidity sensitive, the effect can be minimized by selecting barrier films which minimize the diffusion of humidity in the devices. If the materials are UV sensitive, one can add UV absorbers in the system and/or select substrates which are UV absorbing. Similarly, if a materials diffuses out of the substrate, one can select a substrate, such as high barrier films as substrate and the system can be seals from all sides.

As explained earlier, in Example 11 and in FIG. 21, the device is almost insensitive to quantity of MP. Similarly, as explained earlier, in Example 15 and FIG. 22, the device is almost insensitive to thickness of SP. Additionally, as explained earlier, in Example 10 and FIG. 20, the device is almost insensitive to shape of MP. This make the device of current invention robust, unique and novel.

It is possible to create multi-indicator devices as shown in FIG. 12 for monitoring more than one processes. For example, the indicator changing color with temperature and also with time and temperature. An example of this is a partially polymerized diacetylene, such as 4BCMU used as an indicator, it changes from blue-to-red at ~85° C. and when amyl phenol is used as a MP, it creates a moving boundary devices. Similarly a system can be developed for other processes, for examples, one create a thaw indicator by selecting a proper indicator material which melts and start diffusing through SP and/or permeable barrier when thawed.

Another way of creating multi-sensor devices is to add one indicating devices on, below or on the side of the current devices. For example, one can apply a freeze or temperature indicating device on or below a current indicating device as shown in FIG. 12.

The thaw (freeze to thaw) indicating device for monitoring frozen state and shelf life of the frozen items/perishables, such as frozen foods will be essentially identical to that of time-temperature indicating device, e.g., composed of an activator tape and an indicator tape, and made essentially by the same methods as described herein. The major difference will be the state of the activator or activator layer. The activator/MP for the thaw indicating device will become essentially solid and/or non-migratable/nondiffusable in case of the thaw indicating devices when the item it is applied on is frozen.

By using MP and/or SP which freeze or stop the diffusion, one can develop a freeze-thaw indicator. When benzyl ether was used, the movement of the boundary stopped in the freeze (e.g., about −10° C.) and when it was brought to room temperature or placed in a refrigerator (~7° C.), the boundary started moving. Benzyl ether freezes at 2-3° C. One can develop freeze indicator by using a SP who glass transition temperature is near 0° C.

In addition to process indicating devices which indicate that an object has gone through a process of sterilization, higher classes of indicating devices, integrators and emulators can also be created by using proper activators, indicators, devices and processes disclosed herein.

The devices can be activated by many different ways including those reported in the literature. The devices can be pre-activated/assembled and frozen to stop the diffusion of MP. The device becomes active when brought to a predetermined higher temperature. The device can be in form of two tapes, an activator tape, often referred as MP tape and an indicator tape often referred as SP tape. Both tapes can be stored separately. The devices can be activated by applying one tape over the other and laminating. The device can be kept in inactive form placing a spacer between the activator and indicator and activating by pulling the spacer. If the MP is a liquid, the device can be designed similar to those disclosed in known devices on moving boundary devices listed herein and are incorporated as references. The devices activated by applying pressure on the liquid reservoir. If MP can be micro-encapsulated, the device can be activated by applying pressure. The prefer method activation is applying activator tape on to the indicator tape.

The devices can have many designs and modifications. Some examples are shown in FIGS. 4-12. In its simplest form, a tiny spot of a solid or semi-solid MP can be placed in the center of a circular SP or at one end of SP. In order to make the device machine readable, the indicator and the SP can be printed in form of barcode. Barcodes can also be printed, for example, with a black ink on the devices. The barcode can be two-dimensional and in color. If there is a change in conductivity during movement of boundary, one can create a RFID type devices. The device can be heat sealed to prevent at the edges to prevent MP diffusing out or directing the movement of MP in a direction, e.g., in case of a strip type device. The device can be linear strip, square, circular, triangular or any other shape desired. An MP can be on or under SP. MP can be inside a cavity in SP. It may form a small bump in the device. The MP and SP can be coated or printed using commercially available equipment. MP can be at center (moving from center to periphery), at one edge (moving to the other edge) or at the periphery to move towards center. The size and the rate of movement and size of the boundary will also depend upon the shape of the device. Activators can be spotted from molten state. It is also possible that area for MP can be empty in the SP layer and when laminated the empty space is filled with MP.

Service life and activation energy can be varied by varying the nature of SP, SP and other additives in them. Service life and activation will depend upon the nature of MP and SP, for example, non-polar mobile phase through nonpolar stationary phase, polar mobile phase through polar stationary phase, polar mobile phase and nonpolar stationary phase or vice versa, and non-ionic mobile phase through ionic stationary phase and vice versa. Activation energy can be lowered by using MP which has ability to crosslink. Activation energy can be increased by using a MP which has ability to degrade or decrease the viscosity of SP. Nature of non-plasticizing and plasticizing diluent for MP and SP is one of the major factors for controlling the rate and the activation energy (Ea). Higher concentration of diluent makes the boundary move faster.

The activation energy can be increased by adding additives which decrease the viscosity of SP with increase in temperature, for example adding additives having different melting points or by a mixture of SP having different glass transition temperatures. Similarly, the activation energy can be increased by using a very broad molecular weight distribution SP compared to that having relatively narrow distribution of molecular weight of SP.

Activation energy can also be varied by selecting SP and additives having different thermal expansion coefficient and glass transition temperatures.

The movement of the boundary is usually almost linear in the beginning but becomes asymptotic as it progresses. The "t" (time required for the boundary to move a certain distance, i.e., the rate of its movement) can be varied from hours to years by varying the variables listed herein. Ea and "t" can be varied by varying the nature of MP and SP and other parameters listed herein. The Ea can be varied from about 5 to 60 kcal/mole. Lower and higher Ea is possible.

The devices can be made with service life of hours to years. Preferred service life is 1 to 30 days. The devices can be made to use from −40° C. to 200° C. The preferred temperature range −20° C. to 60° C. The concentration of MP can be varied from a few percent to 100%. Preferred concentration of MP is 70-100%. The concentrations of accelerator can be varied from a 5 to 90%. Preferred concentration is 5-50%. The quantity of MP used can vary from 0.1 mg-1 g depending upon the size of the device, preferred weight is 1-10 mg. The size of MP depend on the shape of the device. For a circular device, the size of MP can vary from 0.1 mm to a few centimeter, the preferred range is 1-10 mm. The thickness of SP layer can be from a 10 nm to 1 mm, preferred thickness is 10 to 100 microns, the thickness of substrates can be from 10 microns to 1 mm, preferred thickness is 10-100 microns. The activation energy of the devices can be varied from essentially zero kcal/mole to about 100 kcal/mole, preferred ranges are 20 to 30 kcal/mole for time-temperature indicating devices, 40-100 kcal/mole for steam sterilization indicator and 0-15 kcal for time indicating devices.

The nature of the MP is one of the major factors for controlling the rate and the Ea. High molecular weight MPs migrate slower than low molecular weight ones. Polar MP/activator migrate faster in polar SP/adhesive and non-polar migrate faster in non-polar SP/adhesive. Polar MP/activator migrate slower in non-polar SP/adhesive and vice versa. The time required for the circle to grow ~5 mm can be been varied from hours to years at room temperature by selecting proper MP/SP pair. Polarity and molecular weight of the diluent can have effect.

Sublimation is a process whereby a solid is vaporized without it going through an intermediate liquid state. Subliming solid have vapor pressure at any given temperature, most solids have very low vapor pressures. An organic, inorganic, organometallic with low heat of fusion, material which decompose can also be used as MP. MP can be a very viscous material with low volatility or solid which sublimes. Subliming dyes, iodine, camphor, benzoic acid, naphthalene, nitrobenzaldehyde (preferably which don't recrystallize, especially rapidly on the surfaces of the devices or don't get adsorb or absorb), unaffected by light humidity etc., preferably solid to vapor/gas but can go through liquid phase can also be used as MP.

The following is list of compounds which are reported to be subliming at different temperatures and can be used as MP for the indicating devices: 2,4,6-tri-tert-butylphenol; pentaerythritol tetrabromide; tantalum(V) chloride; cis-1,2-cyclohexanediol; trans-1,2-cyclohexanediol; malonic acid; trans-2-hexenoic acid amide; (±)-1,3-diphenylbutane; tris(2,4-pentanedionate)cobalt(III); 4,4'-dichlorobiphenyl; hydroquinone; 1,4-dihydroxy-2,2,6,6-tetramethylpiperidine; phenazine; 2-aminobenzoic acid; tris(2,4-pentanedionato)vanadium(III); terephthalic acid monomethyl ester; 4-aminophenol; hexamethylene tetramine; 2-methoxybenzoic acid; 3-chloroaniline hydrochloride; aluminum(III) chloride; 2-diazo-5,5-dimethylcyclohexane-1,3-dione; valeramide; cis-2-butenoic acid amide; 2,6-dimethylnaphthalene; 1-bromo-4-nitrobenzene; furan-2-carboxylic acid; 1,2-dibromotetrachloroethane; trimethylamine borontrifluoride complex; 2,3-dimethylnaphthalene; perfluorohexadecane; bis(cyclopentadienyl)manganese; tetracyanoethylene; succinic anhydride; tellurium(IV) fluoride; ferrocene; 1,2,3-trihydroxybenzene; thiophene-2-carboxylic acid; cyclohexyl ammonium benzoate; tris(2,4-pentanedionato)manganese(III); benzoic acid; dicyclohexl ammonium nitrite; 1-adamantanol; 2-chloroaniline hydrochloride; 1,8,8-trimethylbicyclo[3.2.1]octane-2,4-dione; o-carborane; tungsten(VI) oxochloride; phthalic anhydride; aniline hydrochloride; trans-2-penenoic acid amide; salicylic acid;

1,4-diiodobenzene; dimethyl terephthalate; 2-adamantanone; trans-6-heptenoic acid amide; hexamethylbenzene; quinhydrone; 4-fluorobenzoic acid; niobium(V) chloride; molybdenum(V) chloride; [2.2]metacyclophane; trichloro-1,4-hydroquinone; pyrrole-2-carboxylic acid; trichloro-1,4-benzoquinone; oxalic acid; 2,6-dichloro-1,4-benzoquinone; 2-adamantanol; 1,8-cyclotetradecadiyne; maleic anhydride; benzofurazan; fumaronitrile; chromium hexacarbonyl; 1-bromo-4-chlorobenzene; 1,4-diazabicyclo[2.2.2]octane; carbon tetrabromide; 1,2,4,5-tetramethylbenzene; octafluoronaphthalene; molybdenum hexacarbonyl; gallium(III) chloride; 4-methylpyridine; trimethylboron complex; 4-chloroaniline; hexachloroethane; 2,5,dimethylphenol; 1,4-benzoquinone; 2,3-dimethylphenol; niobium(V) fluoride; 1,4-dibromobenzene; tungsten hexacarbonyl; adamantine; m-carborane; 4,4'difluorobiphenyl; azulene; trans-syn-trans-tetradecahydroanthracene; N-(trifluoroacetyl)glycine; 1-hydroxy-2,2,6,6-tetramethyl-4-oxopiperidine; 2,2'-difluorobiphenyl; bromopentachloroethane; acetamide; biphenylene; 2,5-dimethyl-1,4-benzoquinone; 4-tert-butylphenol; pentafluorobenzoic acid; and butyramide.

Volatile fragrances such as vanilin, ethyl maltol, naphthol methyl ether, Lactones such as decalactone, nonalactone, octalactone, ketones such as cyclopentadecanone, dihydrojasmone, esters such as fructone, hexyl acetate, ethyl methylphenylglycidate, aldehydes such as hexyl cinnamaldehyde, cuminaldehyde, alcohols such as furaneol, and menthol can also be used as accelerator.

Examples of suitable volatile dyes for high temperature devices such as dry heat and steam sterilization include Dupont Oil Red (an azo dye), Amaplast red AAP, Amacel red GG, Organol Vermillion, Amaplast green OZ, Amacel yellow G, Amacel blue BBN, Auramine base, and Orasol yellow 3G. The foregoing dyes, which all belong to a class of dyes known as "solvent dyes", are characterized by high vapor pressure at temperatures such as the temperatures attained by a heat absorbing material located on the exterior surface of flash lamps when flashed, i.e., from about 150° C. to 250° C. primary importance for use in the present invention so long as it is sufficiently volatile and chemically stable at lamp-flashing temperature. Other dyes that can be used in the present inventions include azo dyes, anthraquinone, quinophthalone, styryl, di- or triphenylmethane, oxazine, triazine, xanthene, methine, azomethine, acridine, diazine, 1,4-dimethylaminoanthraquinone, 1,5-dihydroxy-4,8-diaminoanthraquinone bromide or chloride, 1,4-diamino-3,3-dichloroanthraquinone, 1-aminohydroxyanthraquinone, 1-amino-4-hydroxy-2-(β-methoxyethoxy)anthraquinone, methyl, ethyl, propyl, or butyl 1,4-diaminoanthraquinone-2-carboxylate, 1-amino-4-anilidoanthraquinone, 1-amino-2-cyano-4-anilido(or cyclohexylamino)anthraquinone, 1-hydroxy-2-(p-acetaminophenylazo)-4-methylbenzene, 3-methyl-4-(nitrophenylazo)pyrazolone, 3-hydroxyquinophthalone, etc., malachite green, methyl violet, basic dyes modified with sodium acetate, sodium ethanolate, sodium methanolate, etc.

A volatile dye may include, for example, any dye, color or pigment capable of being selectively removed from the bulk material of a given medical device when exposed to the treatment processes described herein. Some examples of volatile dyes include, but are not limited to Color Index (C.I.) No. 74160 (copper phthalocyanine, [phthalocyaninato (2-)] copper, also referred to as copper tetrabenzoporphyrazine or tetrabenzo-5,10,15,20-diazaporphyrinephthalocyanine); C.I. No. 61565 (D&C Green No. 6 (principally 1,4-bis[(4-methylphenyl)amino]-9,10-anthracenedione)); C.I. No. 73000 (D&C Blue No. 6 ([Δ-2,2'-biindoline]-3,3'-dione) or 2-(1,3-dihydro-3-oxo-2H-indol-zylidene)-1,2-dihydro-3H-indol-3-on); and C.I. No. 60725 (D&C Violet No. 2 (principally 1-hydroxy-4-[(4-methyphenyl)amino]-9,10-anthracenedione)) or 1,4-hydroxy-1-(p-toluidino)anthroquinone. It is preferred that at least one volatile dye is selected from the group consisting of copper phthalocyanine, D&C Green No. 6, D&C Blue No. 6, D&C Violet No. 2, and combinations thereof.

It is not necessary to use dye or a coloring material as an activator or MP. There are many pairs of indicators and activators that can be used for the devices proposed here. Any chemical which can react with another material and can introduce a noticeable or measurable change can be used as an activator. Activators could have a co-activator. Co-activator could be a moderator/modulator/controller and could increase or decrease the effect of an activator as desired. Sometimes two activators can have synergistic effect. A solvent, wetter, surfactant or plasticizer can also be used as co-activator. The terms, co-activator, moderator and modulators are used interchangeably herein.

In one embodiment activators can be monomeric, oligomeric, polymeric, monofunctional or multi-functional compounds.

In another embodiment activator can be a halide, oxide, nitrate, nitrite, phosphate, phosphate, phosphonate, sulfate, bisulfate, silicate, sulfite, sulfide, bisulfide, sulfonate, cyanate, cyanide, thiocyanate, acetylacetonate, carboxylate, percarboxylate, carbonate or bicarbonate anion of a mono, di and trivalent cation of a metal or polyatomic anion of nitrogen, mono or polyfunctional compounds or mixture thereof.

When a pH dye is used as an indicator, one can use an acid or a base as an activator or MP for the devices. A variety of amines are available which can be used as a base for the pH dye. Amines, such as primary, secondary, tertiary and quaternary amines of mono or multi-substituted or un-substituted aliphatic, acyclic and aromatic compounds can be used as activators for some of the devices. Examples of amines and their salts include: adamantanamine, adenine, amino cyclohexanol, amino diethylaminopentane, amino dodecanoic acid, amino ethyl dihydrogen phosphate, amino ethyl hydrogen sulphate, amino pentenoic acid, amino propyl imidazole, amino propyl pipecoline, amino sorbitol, amino undecanoic acid, amino-butanol, aminodeoxy-d-sorbitol, aminoethyl dihydrogen phosphate, aminopropyl imidizole, ammonium acetate, ammonium bromide, ammonium carbaminate, ammonium carbonate, ammonium chloride, ammonium dihydrogen phosphate, ammonium ferrocyanide hydrate, ammonium formate, ammonium hydrogen carbonate, ammonium hydroxide, ammonium iron (11) sulfate, ammonium iron (111) citrate, ammonium iron (111) oxalate trihydrate, ammonium nitrate, ammonium per sulfate, ammonium phosphate dibasic, ammonium sulfamate, ammonium sulfate, benzyl-n-methylethanolamine, benzyltrimethylammonium chloride, bis(dimethylamino) benzophenone, chloroethylamine monohydrochloride, chlorohydroxypropyl trimethyl hydrochloride, chloronitroaniline, choline, choline chloride, choline hydroxide, choline iodide, cyclohexyamine, decylamine, diallyl dimethyl ammonium chloride, diaminodiphenylamine, diaminododecane, diaminoheptane, diaminohydroxypropane, diaminononane, diaminooxapentane, diaminopropane, dibutylamino propylamine, dibutyl amino benzaldehyde, diethanolamine, diethyl amine, diethyl aminopropylamine, diisopropyl ethylamine, dimethyl amine, dimethyl amino ethylmethyl-amino ethanol, dimethyl amino benzaldehyde, dimethyl aminopropoxy benzaldehyde, dimethyl aminopropylamine, dimethyl ammopyridine, dimethyl glycine, dimethyl glyoxine, dimethyl imidizole, dimethyl imidizolidinone, dimethyl propane-diamine, diphenyl amine, diphenylamine, diphenylbenzidine, dodecylamine, dodecyltrimethylammoniumbromide, ethanolamine, ethanolamine hydrochloride, ethyl amine, ethyl aminobenzoate hydrochloride, glycidil trimethyl ammonium chloride, histidine, hydroxylamine hydrochloride, hydroxylamine sulphate, imidazole, imidazolidone, iminodiacetic acid, methyl amine, methyl imidizole, nitro aniline, nitro diphenylamine, octa decylamine, phenylenediamine, polyethylenimine, tetrabutyl ammonium hydroxide, tetrabutyl ammonium iodide, tetraethylammonium bromide, tetraethylammonium hydroxide, tetrafluorophenylimidizole, tetrahexylammonium bromide, tetramethyl ammonium acetate, tetramethyl ammonium chloride, tetramethyl ammonium hydroxide, tetramethyl ethylenediamine, tetramethyl ethylethylenediamine, tetramethyl hexanediamine, tetramethyl propanediamine, tetramethyl guanidine, triallylamine, triethanolamine, triethylamine, triethylenetetramine, triethylenetetramine hydrochloride, triethylethylenediamine, tridecylamine, trimethyl ammonium chloride, trimethyl-propanediamine, trimethylamine hydrochloride, trioctylamine, trioxa-tridecanediamine, triphenylamine, tris(hydroxymethyl) aminomethane and tris (methoxyethoxy) ethylamine.

Acids, bases and salts can be used as activators or MP and hence if desired their reaction can be monitored with pH, cation and anion sensitive dyes. For example, bromophenol blue when exposed to a base, such as sodium hydroxide turns blue. When blue-colored bromophenol blue is exposed to acids, such as acetic acid it will undergo a series of color changes, such as blue to green to green-yellow to yellow. Aluminum ion reacts with alizarins to give a red precipitate; copper ions react with cuproine to give a pink purple color, ferrous ion gives a red color with 2,2'-dipyridyl, ferric ion reacts with potassium ferrocyanide to give a blue color, magnesium ion gives a blue color with magnesium and nickel ion reacts with dimethylglyoxime to give a red color. Test methods are also well known for the detection of inorganic compounds, their cations and anions, which are associated with a color change. These reactions and corresponding compounds can also be used in the device, especially if a color change is also desired. Inorganic compounds and indicators for their detection are described in references: J. Bassett, R. C. Denney, G. H. Jeffery and J. Mendham, Vogel's Textbook of Quantitative Inorganic Analysis, Longman Scientific and Technical, p. 294, 1986; Fritz Feigl, Vinzenz Anger and Ralph E. Oesper, Spot Test in Inorganic Analysis, Elsevier Publishing Company, 1972, p. 526-616; Products for Analysis, Catalog of Hach Company, 1986-87 (are cited as references herein).

These are dyes or compounds which react almost instantly with activators to introduce a color change can be used as indicators to indicate activation of the device. These are typically pH dyes. The preferred material is a colored dye which becomes colorless when contacted with the activator or vice versa. The reaction between the activation indicator and the activator should occur almost instantly as the label applicator will apply hundreds of labels a minutes and hence in order to monitor activation, the color change should be as fast as possible. It is highly desirable to have this feature. Just an application of an activator tape on the indicator tape does not mean the device is activated. The activation indicators will confirm that the device is activated and also visually noticed.

A large number of reactions are associated with a change in fluorescence rather than a color change in the visible region. Such compounds can be used as indicator and for security in the device. All colors herein could also be fluorescence colors as well.

Mobile phase can be an ionic liquid. A polar MP will diffuse easily through a polar SP and vice versa.

In case of non-selective pairs of indicators and activators, an activator reacts with a large number of indicators and vice versa. For example, in case of a pH dye as a non-selective indicator, a numbers of activators, e.g., acids or amines can change the color of the pH dye and vice versa. In addition to non-selective pairs of indicators and activators, this invention also comprises selective pairs of indicators and activators. Many classes of compounds react selectively only with certain small number of compounds. For example, a chelate will react only with certain metal ions and vice versa to produce color metal chelate complexes. Indicators which selective react with a small number of activators and vice versa are referred pairs of indicators and activators. Further preferred selective pairs of indicators and activators are chelates and metals ions or metal complexes. Still further preferred selective pairs of indicators and activators are chelates which reacts with low toxicity metals such as iron, for example a pair of 1,10-phenanthroline and iron chloride or iron acetate.

An MP can be a chelating or complexing agents. The choice of chelating or complexing agents will depend on metal atom (either as a salt or complex) used in SP and nature of SP. Examples of chelating or complexing agents include, carbonyl compounds (e.g., acetylacetonates), simple carboxylates (e.g., acetates, aryl carboxylates), carboxylates containing one or more hydroxyl groups (e.g., glycolates, lactates, gluconates, gallic acid and salts thereof), di-, tri-, and poly-carboxylates (e.g., oxalates, phthalates, citrates, succinates, tartarates, malates, edetates (e.g., dipotassium EDTA), mixtures thereof), carboxylates containing one or more sulfonic and/or phosphonic groups, and the like. Suitable chelating or complexing agents also can include, for example, di-, tri-, or polyalcohols (e.g., ethylene glycol, pyrocatechol, pyrogallol, tannic acid) and amine-containing compounds (e.g., ammonia, amino acids, amino alcohols, di-, tri-, and polyamines).

Other examples of chelating agents include trisodium pyrophosphate, tetrasodium diphosphate, sodium hexametaphosphate, sodium trimetaphosphate, sodium tripolyphosphate, potassium tripolyphosphate, phosphonic acid, diphosphonic acid compound, tri-phosphonic acid compound, and a salt of a phosphonic acid compound, ethylene diamine-tetra-acetic acid, gluconate, or another ligand-forming compound. The chelating agents also include phosphonic acid-based chelating agents, such as aminotri(methylenephosphonic acid), 1-hydroxyethylidene-1,1-diphosphonic acid and ethylenediaminetetramethylenephosphonic acid; aminocarboxylate-based chelating agents, such as ethylenediaminetetraacetates and nitrilotriacetates; hydroxyaminocarboxylate-based chelating agents, such as dihydroxyethylglycine; or mixtures thereof.

Still further examples of chelating agents include amino acids, such as glycine, serine, proline, leucine, alanine, asparagine, aspartic acid, glutamine, valine, lysine, etc.; polyamine complexes and their salts, including ethylenediaminetetraacetic acid, N-hydroxyethylethylenediaminetriacetic acid, nitrilotriacetic acid, iminodiacetic acid, diethylenetriaminepentaacetic acid, and ethanoldiglycinate; polycarboxylic acids, including phthalic acid, oxalic acid, malic acid, succinic acid, mandelic acid, mellitic acid; alkali metal or ammonium salts of acetic acid, citric acid, tartaric acid, gluconic acid, lactic acid, propionic acid, or mixtures thereof.

Some example of compounds which react with ferrous and ferric salts and organo-iron compounds include ammonium ferrocyanide (II) hydrate, ammonium iron (III) oxylate hydrate, ammonium iron (III) sulfate hexahydrate, ammonium iron (III) sulfate dodecahydrate, ammonium thiocyanate, ammonium thiosulfate, aluminum chloride hexahydrate, luminum nitrate nonahydrate, copper (II) acetate monohydrate, copper (II) bromide, copper (II) chloride hydrate, copper (II) sulfate pentahydrate, ferrocene, iron (II) sulfate heptahydrate, nickel (II) chloride, sodium diethyldithiocarbamate trihydrate, sodium iodide, sodium thiosulfate pentahydrate, tin (II) bromide, tin (II) 2-ethylhexanoate, zinc acetylacetonate hydrate, zinc bromide and zinc chloride.

Some examples of organic compounds which react with ferrous and ferric salts and organo-iron compounds includes fast orange base GC, 2-amino-p-cresol, benzenesulfonic acid, tert-butylhydroquinone, 2,6-di-tert-butyl-4-methylphenol, diphenylamine, diazoaminobenzene, hydroquinonesulfonic acid potassium salt, DL-malic acid, mandelic acid, methylhydroquinone, octadecylamine, trimethylhydroquinone, and 2,3,4-trihydroxybenzophenone.

Accelerators are compositions which can increase diffusion of MP through SP. They can be used to increase the speed of movement of the boundary created by MP. They can also change the activation energy of the system. Accelerator can be in a SP and/or MP. Accelerator can be a solvent, preferably high boiling and a plasticizer. Accelerator can also be solid compounds which rapidly diffuse through the SP. Compounds which sublime can also increase the speed of the boundary. If accelerator is only in the mobile phase and an indicator or dye is in the stationary phase it can create a line or ring or an edge/wave if the device the movement is restricted in one direction.

High boiling and solid solvents which can dissolve an activator can be used to facilitate migration of activator. If required, a solvent can be used for a solid activator. High boiling solvents, such as cinnamoyl alcohol, xylenol, phenolethanol, diphenylether and a large number of other organic and inorganic compounds can be used as solvents for activators.

It has been observed that often solvents, expedite the diffusion of the activator and reaction with the indicators.

Solvents or liquids as aids, facilitator, promotors to migration of activator useful in the invention devices includes the following: water, $C_1$-$C_{15}$ aliphatic, aromatic and substituted aliphatic and aromatic amides preferably acetamide, dimethylformamide and chloroacetamide; alcohols, preferably amyl alcohol, hexyl alcohol, and dichloropropanol; esters, preferably methylpropionate, amylformate, diethyl maleate, ethylene glycol diacetate, ethylsalicylate, and triacetin; nitroalkanes preferably nitropropane; aldehydes, preferably butyraldehyde; carbonates, preferably diethylcarbonate and propylene carbonate; aromatic alcohols/phenols, preferably dihydroxy benzene, benzyl alcohol and phenol; amines, preferably diethanolamine, dimethylpyridine and cyclohexane diamine; ether-esters preferably ethoxyethylacetate, trioxane, tetraethylene glycol dimethylether, benzyl ether, phenylether, propylene glycol ethylether acetate and propylene glycol butylether; alcohol-esters, preferably ethylene glycol monoacetate; acids, preferably glutaric acid, isobutyric acid, mandelic acid, and toluene sulfonic acid; ketones, preferably methylethylketone and hydroxyacetophenone; ketone-esters, preferably methylacetoacetate; lactones, preferably propiolactone and butyrolactone, methylpyrrolidone and mixture thereof. One can use more than one activator solvent in varying proportions. One may use additives, such as co-solvents (especially highly polar organic solvents, such as alcohols, acids and amines, and ethers) surfactants and nucleating agents. Many of these solvents can also be used as a wetter.

Specific examples of solvents include butoxy-2-ethylstearate, butyrolactone, diethyl fumarate, dimethyl maleate, dimethylcarbonate, dioctyl phthalate, ethylene glycol dimethyl ether, ethyl salicylate, polyethylene glycol dimethylether, propylene carbonate, triacetin, benzyl ether, dodecyl-1,2-methyl pyrrolidone, ethoxyethylacetate, ethylene glycol diacetate, ethyltrichloroacetate, methylpyrrolidone, methyl sulfoxide, polyethylene glycols of different molecular weight, dimethylformamide, cyclohexane, p-dioxane, tetrahydrofuran, p-xylene, acetone, 2-butanone, ethyl acetate, propyl acetate, toluene, xylene and hexane. Many of these solvents can also be used as a wetter.

Plasticizers are preferred class of accelerator. They include sebacates, adipates, terephthalates, dibenzoates, gluterates, phthalates, azelates, and other specialty blends. Dicarboxylic/tricarboxylic ester-based plasticizers such as bis(2-ethylhexyl) phthalate, diisononyl phthalate, di-n-butyl phthalate, butyl benzyl phthalate, diisodecyl phthalate, di-n-octyl phthalate, diisooctyl phthalate, diethyl phthalate, diisobutyl phthalate, di-n-hexyl phthalate, trimellitates such as trimethyl trimellitate, tri-(2-ethylhexyl) trimellitate, tri-(n-octyl, n-decyl) trimellitate, tri-(heptyl, nonyl) trimellitate and n-octyl trimellitate, adipates such as bis(2-ethylhexyl) adipate, dimethyl adipate, monomethyl adipate and dioctyl adipate, sebacates such as dibutyl sebacate, maleates such as dibutyl maleate and diisobutyl maleate, benzoates, phthalates such as dioctyl terephthalate, and others such as 1,2-cyclohexane dicarboxylic acid diisononyl ester, epoxidized vegetable oils, alkyl sulphonic acid phenyl ester, sulfonamides such as N-ethyl toluene sulfonamide, N-(2-hydroxypropyl) benzene sulfonamide, N-(n-butyl) benzene sulfonamide, organophosphates such as tricresyl phosphate and tributyl phosphate, glycols/polyethers such as triethylene glycol dihexanoate and tetraethylene glycol diheptanoate, polymeric plasticizers such as polybutene, biodegradable plasticizers such as acetylated monoglycerides, alkyl citrates, triethyl citrate, acetyl triethyl citrate, tributyl citrate, acetyl tributyl citrate, trioctyl citrate, acetyl trioctyl citrate, trihexyl citrate (THC), acetyl trihexyl citrate, butyryl trihexyl citrate, trihexyl o-butyryl citrate, and trimethyl citrate.

Preferred MP is a non-solvent or poor solvent for the SP. If a MP is good solvent for SP, it swell and/or dissolve the substrate and will be used up. As a result, the movement of the boundary will be non-linear. When the concentration of indicator is high, higher amount of activator is required and that proportionally slows the movement of the boundary and vice versa. On the other hand, when the concentration of indicator is high, the boundary will be darker and vice versa.

The nature (hardness or softness) of SP/PSA is a major determining factor for the speed of the boundary and the Ea. Hardness of PSA can be depends upon the nature of PSA, molecular weight, crosslinking and plasticization. Higher the plasticization, faster the movement of the boundary. The time required for the circle to grow ~5 mm has been varied from hours to year+ at room temperature by selecting proper plasticizer for SP.

Any solid substrate can be used as a substrate for the indicating device. Preferred substrate is a flexible plastic film and natural (cellulose) and synthetic (e.g., spun bonded polyolefins, e.g., Tyvek™) papers. Fiber reinforced substrate can be used for sealing tape indicating device. Plastic substrate could be self-colored (pigmented) or coated with a color layer. It could be transparent, semi-transparent, translucent or colored with various intensities. The polymer films include polyolefins (linear or branched), polyamides, polystyrenes, nylons, polyesters, polyurethanes, polysulfones, styrene-maleic anhydride, styrene-acrylonitrile, ionomers based on sodium or zinc salts of ethylene methacrylic acid, polymethyl methacrylates, cellulosics, acrylic polymers (acrylates, such as ethylene methacrylic acid, ethylene methyl acrylate, ethylene acrylic acid and ethylene ethyl acrylate), polycarbonates, cellophane, polyacrylonitriles, ethylene-vinyl acetate and their copolymers can be used as substrate for the devices. The preferred substrates are polyethylene, polypropylene, polyester, cellulose acetate, polyvinyl chloride and their copolymers. These substrates can be metallized.

One may use high barrier film, such as EVOH (ethylene vinylalcohol copolymer) or plastic films coated with aluminum oxide and silicone oxide impermeable substrates are preferred. Impermeable to any component of the device, heat sealable, coatable, and transparent top and preferably opaque as the bottom, metallized films are preferred for the bottom substrate. Substrate should be non-permeable to dyes and all components of the devices. Porous SP, such as cellulose paper, cotton, polypropylene, glass paper (less absorptive) wetted with a liquid or amorphous solid which fill the pores can also be used.

The type of adhesive that can be used includes hot melt, PSA, repositionable, or film, such as polyethylene. SP can be wedge shaped. Thinner matrix is preferred as thicker will require more quantity of activator. Adhesives or viscoelastic materials, for example, include the use of synthetic elastomers, acrylates, silicone, synthetic latex and vinyl acetate, as representative examples of pressure sensitive adhesives (PSA) are one of the preferred material for the PSA layer of the SP. Included are pressure sensitive adhesives having an elastomer or rubbery polymer as the elastic component and a low molecular weight tackifying viscous component. Common rubber based pressure sensitive adhesives include natural elastomers, synthetic elastomers, such as polychloroprene, polyurethane, and random and block copolymers of styrene-butadiene, styrene-isoprene, polyisobutylene, butyl rubber, and amorphous polypropylene. An illustrative, but by no means exclusive, list of viscoelastic materials which may be suitable for use with the indicator of the present invention includes natural rubber, butyl rubber, polybutadiene and its copolymers with acrylonitrile and styrene, poly alpha olefins, such as polyhexene, polyoctene, and copolymers of these and others, polyacrylates, polychloroprene, silicone pressure sensitive adhesives, and block copolymers, such as styrene-isoprene block copolymers, and mixtures of any of the above. The pressure sensitive adhesive can comprise, for example, a polyisoprene, atactic polypropylene, polybutadiene, polyisobutylene, silicone, ethylene vinyl acetate, or acrylate based pressure sensitive adhesive, and can typically include a tackifying agent and/or a plasticizing agent. The adhesives also include isooctyl acrylate (IOA) or isooctyl acrylate/acrylic acid (IOA/AA) based pressure sensitive adhesive.

Common acrylic adhesives, such as polymers of 2-ethylhexylacrylate, butyl acrylate, ethylacrylate, and acrylic acid can be used. These acrylic adhesives are inherently pressure sensitive. Polymers and copolymers of vinyl ethers, such as vinylmethylether, vinylethylether and vinylisopropylethers are used as pressure sensitive adhesives. Two types of silicone gums; 1) all methyl based and 2) the phenyl modified can also be used as pressure sensitive adhesives.

The silicone resin is used as a tackifier and by adjusting the resin to gum ratio, they can be made with a wide range of adhesion properties. High silicone gum content adhesives are extremely tacky. Silicone adhesives are also crosslinked (cured) by catalysts, such as benzoyl peroxide and amino silane.

A PSA which is least affected by activator or does not affect activator is preferred. PSA is preferred but any other adhesives, such as hot melt adhesive can be used. For certain devices, such as time indicating devices or visitor badges, it is preferred that the bonding of the PSA layer is much stronger with the indicator layer so it can't be easily tampered. UV and peroxide curable adhesive can also be used.

There is a significant effect of nature of SP/PSA on the rate and the Ea. The boundary moves slower in a harder SP/PSA and vice versa. Hardness of PSA can depends on factors such as the nature of PSA, molecular weight, crosslinking, additives and plasticization. The time required for the circle to grow ~5 mm has been varied from hours to year+ at room temperature by selecting proper MP/SP pair.

The SP and MP can have many additives to vary service life and activation energy. These additives can be solid, semi-solid or liquid. Solid additives for SP and MP can be porous or non-porous, adsorbing or non-adsorbing, permeable or non-permeable, viscous, crystalline or amorphous, soluble or insoluble, size varying from nano meter to several microns, organic or inorganic, polymeric, oligomeric or monomeric, neutral or reactive and others disclosed herein.

In one experiment, the following high boiling liquids, some of which are plasticizers, were tested for acceleration of diffusion of methyl yellow in about 25 micron coating of S85 PSA and an acrylic hot melt adhesive of Transilwrap: benzyl ether, dibutyl adipate, dibutyltin diacetate, diethylene glycol monoethyl ether, diethyl malate, diethyl malonate, diethyl succinate, dimethyl carbonate, dimethyl maleate, dimethyl malonate, 2-ethyl-1,3-hexanediol, 2-phenoxyethanol, Tetradecane and tridecene.

Hot melt pressure sensitive adhesives typically comprise a block copolymer, a tackifying resin and a plasticizing oil can also be used. The block copolymer provides flexibility, integrity and smooth peel adhesion properties. It also further provides a medium for dissolution or suspension of the tackifying resin and the plasticizing oil. The tackifying resin enhances tack properties and adhesion and reduces viscosity and the plasticizing oil reduces peel values, viscosities, glass transition temperatures and storage modulus and increases flexibility.

Tackifiers are chemical compounds used in formulating adhesives to increase the tack, the stickiness of the surface of the adhesive. They are usually low-molecular weight compounds with high glass transition temperature and softening temperature above room temperature, providing them with suitable viscoelastic properties. In hot melt adhesives they can comprise up to about 40% of total mass. Tackifiers are usually resins (e.g. rosins and their derivatives, terpenes and modified terpenes, aliphatic, cycloaliphatic and aromatic resins (C5 aliphatic resins, C9 aromatic resins, and C5/C9 aliphatic/aromatic resins), hydrogenated hydrocarbon resins, and their mixtures, terpene-phenol resins (used often with ethylene-vinyl acetate adhesives)). Many pressure-sensitive adhesives are a blend of rubbers (natural or synthetic) and a tackifying resin. Some acrylic adhesives also include an additional tackifier. Silicone rubber-based pressure-sensitive adhesives require special tackifiers based on "MQ" silicate resins, composed of a monofunctional trimethyl silane ("M") reacted with quadrafunctional silicon tetrachloride ("Q").

Many water soluble/swellable polymeric systems, such as those based on plasticized and unplasticized polyethylene glycol, cellulose ethers, polyvinylpyrrolidone, polyvinyl methyl ether, polyaminomethylmethacrylate, polyacrylates, copolymer of methyl and/or ethylesters of acrylic acid and methacrylic acid, vinyl pyrrolidone/vinyl acetate, vinyl pyrrolidone, methacrylic acid, and natural products, such as dextrin, gelatin, casein and starch can also be used a binder/PSA for activator for monitoring humidity/moisture. The system described in U.S. Pat. Nos. 4,215,025; 4,331,576; 4,490,322; 4,775,374; 5,133,970; 5,296,512; 5,296,512; 5,395,907; 5,565,268; 6,326,524; 6,444,761 and 7,465,493; EP1458366; U.S. Patent Applications 20090018514; 20090030361 and 20090062713 and WO/1995/005416; WO0230402; WO0021582 and WO 0154674 and references, formulations and processes cited therein can also be used as a SP for activator and indicator. These patents and patent applications are hereby incorporated by reference into the specification of the present invention.

Materials which form a gel can also be used as a binder. Polymers which are crosslinked or can be crosslinked can also be used. They include natural and synthetic polymers, such as gelatin, agar, agarose, "Super Slurper", which is a sodium salt of 60% graft copolymer of starch, polyacrylamide and acrylic acid. The advantage of using Super Slurper (commercially available from the Aldrich Chemical, Milwaukee, Wis.) is that a gel can be formed at room temperature without the necessity of heating followed by cooling to room temperature. One can use a variety of polymers, copolymers and their mixtures as binders to get desired properties, such as high gel strength and high gelling temperature. Polymers which can retain solvent or activator are preferred. Water insoluble polymers which form a gel in a combination of solvent and nonsolvent can also be used for this device. Reversible gel forming polymers listed in the following books and reviews can also be used: (1) "Reversible Polymeric Gels and Related Systems", Paul S. Russo, ACS Symposium Series #350, Washington, D.C., 1987; (2) L. L. Hench and J. K. West, Chem. Rev., 90, 33 (1990); (3) "Hydrogels" reported by Nagasaki and K. Kataoka, in Chemtech, p 23 Mar. 1997; E&E News, Jun. 9, 1997 p 26, Encyclopedia of Polymer Science Technology, 7, 783 (1986); (4) "Reversible Crosslinking", Encyclopedia of Polymer Science Technology, 4, 395, (1986), L. Z. Rogogovina and G. L. Slonimiski, and Russian Chemical Review, 43, 503 (1974) and (5) "Polymer Handbook" by A. Hiltner, Third Edison (J. Brandrup and E. H. Immergut Eds), John Wiley and Sons, New York, N.Y. 1989.

Permeable layer as defined herein is a layer which is permeable to activator or MP. Any material which lets activator diffuse or migrate through under controlled conditions can be used to make a permeable layer. Preferred permeable layer is a polymer. The nature of the permeable layer will depends on the activator. It is mainly used to vary/increase the time required for the transparency change and vary the activation energy of the reaction/device. Permeable layer materials include glassy polymers, semi-crystalline polymers, physically and chemically crosslinked elastomers, segmented polyesters, polyamides, radiation crosslinked polybutadiene, and pressure sensitive adhesives. Examples of suitable glassy polymers include polystyrene, polyvinyls, and halopolymers, such as polyvinylchloride, polyepichlorohydrin and acrylates, such as polymethyl methacrylate. Examples of suitable semi-crystalline polymers include polyethylene, polypropylene and polyesters. Examples of suitable physically crosslinked elastomers include triblock copolymers, such as styrene-isoprene-styrene block copolymers, and segmented polyurethane elastomers. An example of a suitable chemically cross-linked elastomer is sulfur crosslinked natural rubber. In the one embodiment, the permeable layer material is a pressure sensitive adhesive including acrylic pressure sensitive adhesives, silicone pressure sensitive adhesives, rubber resin blend pressure sensitive adhesives, triblock copolymer pressure sensitive adhesives, and vinyl ether polymer pressure sensitive adhesives. Rubber resin blend pressure sensitive adhesives include natural rubber, polybutadiene, polyisobutelene, styrene butadiene random copolymers, synthetic polyisoprene, and butyl rubber. Useful triblock copolymer pressure sensitive adhesives include styrene-isoprene-styrene copolymers, styrene-butadiene-styrene copolymers, styrene-ethylene butylene-styrene copolymers, and styrene-ethylene propylene-styrene copolymers. Commercially available latexes, and the raw (without any color) materials for making inks, paints, lacquers, varnishes and adhesives can be used as a permeable layer materials. Thickness of the permeable layer can be in the range of 0.001 mm to 0.1 mm. Permeable layer could have a neutralizer of activator.

Polyvinyl alcohol, polyvinyl acetate, partially hydrolyzed polyvinyl acetate, polyvinyl ether, cellulose derivatives, such as nitrocellulose, cellulose acetate, cellulose acetate butyrate, methyl cellulose, ethyl cellulose, gums, such as guar gums, starch, proteins, such as gelatin can be used as permeable layer.

Water soluble polymers can also be used as a binder for activator, adhesive and permeable layer. The examples of water soluble polymers include: agar, agarose, alginic acidamylase, beta-glucan, carboxymethylcellulose, carrageenan, cellulose etherschicle gum, chitin, dammar gum, ethylcellulose, gelatin, gellan gum, guar gum, gum arabic, gum ghatti, gum tragacanth, gum xanthan, hydroxy ethyl cellulose, hydroxy ethyl starch, karaya gum, locust bean gum, mastic gum, partially hydrolyzed polyacrylamide, poly acrylamide, poly acrylic acid, poly crotonic acid, poly hydroxy-2-ethylmethaacrylate, poly hydroxy-3-butyric acid, poly lysine, poly methacrylic acid, poly methyl vinyl ether, poly propylene glycol, poly vinyl acetate—partially hydrolized, poly vinyl alcohol, poly vinyl methyl ether, poly vinyl phenol, poly vinyl pyrrolidone, polyacrylates, polyacrylic acids, polyallylamine, polyaminoacids, polyethylene/acrylic acid, polycarboxylates, polyethylene glycol, polyethyleneimine, polystyrene sulfonic acid, polyvinylamine, polyvinylpyrrolidone, sodium alginate, spruce gum, tara gum, xanthan gum, their copolymers, block copolymers, derivatives, including copolymers with water insoluble polymers. Water soluble polymers are preferred binders for activator for thaw indicating device because when water is used as a solvent for activator, it can freeze the whole layer and may either prevent or minimize the migration of activator and provide controlled release of the activator.

The following is a list of examples of dyes tested as indicator: Acid red 1, Acid alizarin violet N, Acid black 24, Acid black 48, Acid blue 113, Acid blue 120, Acid blue 129, Acid blue 161, Acid blue 25, Acid blue 29, Acid blue 40, Acid blue 41, Acid blue 45, Acid blue 80, Acid blue 92, Acid fuschin, Acid green 25, Acid green 27, Acid green 41, Acid orange 74, Acid red 1, Acid red 114, Acid red 151, Acid red 88, Acid violet 17, Acid violet 7, Acid yellow 99, Acridine orange, Acridine orange base, Acridine yellow G, Acriflavine HCl, Alacian blue 8GX, Alcian yellow, Alizarin, Alizarin blue black SN, Alizarin complexone dihydrate, Alizarin complexone hydrate, Alizarin red, Alizarin violet 3R, Alizarine yellow GG, Alizarine yellow R, Alizarin blue black B, Alkali blue 6B, Alkali fast green 10GA, Alphazurine A, Aluminon, Aminoacridine HCl, Aminoanthraquinone, Aminophthathylhydrazide, Aniline blue, Water soluble, Astra blue 6GLL, Astrozon orange G, Auramine O, Azocarmine B, Azocarmine B, Azure A, Azure B, Azure B thiocyanate, Azure C, Basic blue 3, Basic blue 41, Basic blue 66, Basic fuchsin, Basic red 29, Basic yellow 11, Benzo purpurin 4B, Biebrich scarlet, Na salt, Bismarck brown Y, Bismark brown R, Blue tetrazolium, Bordeaux R, Brilliant blue G, Brilliant blue R, Brilliant cresyl blue ALD, Brilliant crocein MOO, Brilliant green, Brilliant sulphaflavine, Brilliant yellow, Bromochlorophenol blue-Na salt, Bromocresol green, Bromocresol green-water soluble, Bromocresol purple, Bromocresol purple-water soluble, Bromophenol blue, Bromophenol blue-water soluble, Bromopyrogallol red, Bromothymol blue, Bromothymol blue-water soluble, Bromoxylenol blue, Calmagite, Carbol fushsin, Carminic acid, Carotene beta, Celestine blue, Chicago sky blue, Chlorophenol red, Chrome azurol S, Chromotrope 2B, Chromotrope 2R, Chromoxane cyanine R, Chrysoidin, Chrysophenine, Cibacron brilliant red 3BA, Congo red, Copper (ii) phthalocyanine, m-Cresol purple, m-Cresol purple-water soluble, Cresol red, Cresol red-water soluble, Cresolphthalein complexone, Cresolphthalein-O, Crystal violet, Curcumin, Darrow red, Diaminoacridine hemisulfate, Diazo red RC, Diazo-2-naphthol, Diazo-4'-methoxydiphenylamine, 4,5-dibromofluorescein, Dichlorofluorescein, Dichloroindophenol-Na salt, Dicinnamalactone, 3,3-diethyl-ethylthiacyanine iodide, Diethylaminomethylcoumarin, 3,3-diethyloxacarbocyanine iodide, 3,3-diethylthiatricarbocyanine-iodide, dilithium phthalocyanine, Dimethyl methylene blue, 3,6-dimethyl-2-4dimethylaminophenyl benzoate, 2,4-dimethylaminostyryl-1-methyl quinolinium iodide, Dimethylglyoxime, Dimethylindoaniline, Dinitro-2-biphenylamine, 1,5-diphenycarbazide, Diphenylamine-$H_2SO_4$, Diphenylthiocarbazone, Direct blue 71, Direct green 6, Direct red 23, Direct red 75, Direct red 81, Direct violet 51, Direct yellow 62, Disperse blue 1, Disperse blue 14, Disperse blue 3, Disperse orange, Disperse orange 11, Disperse orange 25, Disperse red 1, Disperse red 13, Disperse yellow 7, Disodium phthalocyanine, Emodin, Eosin B, Spirit soluble, Eosin Y, Eosin Y free acid, Eriochrome black T, Eriochrome blue black B, Erioglaucine, Erythrosin B, Ethyl eosin K-salt, Ethyl orange-Na salt, Ethyl red, Ethyl violet, Evans blue, Fast black K salt, Fast blue 2B salt, Fast blue 3GL, Fast blue B salt, Fast blue BB, Fast blue BB salt, Fast blue RR, Fast blue RR salt, Fast blue VB salt, Fast corinth V salt, Fast garnet GBC base, Fast garnet GBC salt, Fast green FCF, Fast red 3G salt, Fast red AL salt, Fast red B salt, Fast red ITR, Fast red TRT salt, Fast red PDC salt, Fast red TR salt, Fast red violet LB salt, Fast scarlet 2G salt, Fast scarlet R salt, Fast violet B salt, Fast yellow GC salt, Fat brown RR, Flavazin L, Flavianic acid, Hydrate, Fluorescein, Fluorescein-water soluble, Fluorexon, Gallocyanine, Glyoxal bis(2-hydroxynil), Guinea green B, Haba (2-4-hydroxyphenylazo)benzoic, Hematoxylin, Hydroxy naphthol blue, 2-Hydroxy-1,4-naphthoquinone, 2-Hydroxy-naphthoic acid-1, 7-Hydroxy-4methylcoumarin, Indigo, Indigo carmine, Indoline blue, Iron (ii) phthalocyanine, Janus green B, Lacmoid, Leishman stain, Leuco crystal violet, Leucomalachite green, Leucoquinizarin, Light green SF yellowish, Lissamine green B, Litmus, Luxol fast blue MBSN, Malachite green base, Malachite green HCl, Malachite green oxalate, Metanill yellow, Methyl eosin, Methyl green, Methyl orange, Methyl red, Methyl red HCl, Methyl red Na-salt, Methyl violet 2B, Methyl violet B base, Methyl yellow, Methylene blue, Methylene green, Methylene violet 3RAX, Methylesculetin, Methylthymol blue water soluble, Mordant blue 9, Mordant brown 24, Mordant brown 4, Mordant orange 1, Mordant orange 6, Mordant red 19, Mordant yellow 10, Morin hydrate, Murexide, Naphthochrome green, Naphthol AS, Naphthol AS-BO, Naphthol AS-BS, Naphthol AS-G, Naphthol AS-MX, Naphthol AS-OL, Naphthol AS-SW, Naphthol blue black, Naphthol green B, Naphthol yellow, Alpha naphtholbenzein, Neutral red, New coccine, New fuchsin, New methylene blue N, Nigrosin, Alcohol soluble, Nile blue A, Nile blue chloride, Nitrazine yellow, Nitro red, Nitro-phenanthroline, 2-nitrophenol, 3-nitrophenol, 4-nitrophenol, 4,4-nitrophenylazo-resorcinol, Nitrophenylazo-resorcinol, Nuclear fast red, Oil blue N, Oil red EGN, Oil red O, Orange G, Orange II, Palatine chrome black 6BN, Palatine fast yellow BLN, Pararosaniline acetate, Pararosaniline base, Pararosaniline chloride, Patent blue VF, Pentamethoxytriphenyl methanol, 1,10-phenanthroline, Phenazine, Phenol red, Phenol red-water soluble, Phenolphthalein, Phenolphthalein diphosphate, Phenothiazine, 4-phenylazoaniline, 4-phenylazodiphenylamine, 2-phenylazoformic acid, 4-phenylazophenol, Phloxine B, Phthalocynine, Pinacyanol chloride, Plasmocorinth B., Ponceau S, Primuline, Procion red MX-5B, Procion yellow H-E3G, Prussian blue, Purpurin, Pyridylazoresorcinol-Na salt, Pyrocatechol violet, Pyrogallol red, Pyronin B, Quinaldine red, Quinizarin, Quinoline yellow, Spirit soluble, Reactive black 5, Reactive blue 15, Reactive blue 2, Reactive blue 4, Reactive orange 16, Resazurin, Resorcin crystal violet, Rhodamine B, Rhodamine B base, Rhodamine GG, Rhodamine S, Rhodanine, Rosalic acid, Rose bengal, Rose bengal lactone, Safranine), Solvent blue 35, Solvent blue 59, Solvent green 3, SPANDS, Stains all, Styryl, Sudan black B, Sudan II, Sudan orange G, Sudan red 7B, Sulfobromophthalein-Na salt, Sulforhodamine B, Tartrazine, Tetrabromophenol blue, Tetrabromophenol blue-Na salt, Tetrabromophenolphthalein, Tetrabromophenolphthalein water soluble, Tetrabromophenolsulfonephthalein, Tetraiodophenolphthalein, Tetraiodophenolphthalein-water soluble, Tetraphenyl-butadiene, Tetrazolium violet, Thiazol yellow G, Thioflavin S, Thioflavin, Thionin, Thymol blue, Thymol blue, Sodium salt, Thymolphthalein, Thymolphthalein monophosphate, Thymolphthalein monophosphate, Toluidine blue O, Triphenylmethyl bromide, Tropaelin O, Trypan blue, Turmeric, Vanillin azine, Variamine blue RT salt, Variamine blue RT salt, Victoria blue B, Victoria blue R, Victoria pure blue BO, Wright stain, Xilidine ponceau 2R, Xylenol blue, and Xylenol orange-water soluble.

The following is a list of examples of organic compounds tested as MP: 4-acetamidophenol, acetone oxime, 2-amino-p-cresol, 4-tert-amylphenol, ascorbic acid vc, azodicarbonamide, benzilic acid, 2-(2H-benzotriazol-2-yl)-6-dodecyl-4-methylphenol, benzotriazole, benzenesulfonic acid, benzyl sulfoxide, 2-benzoylbenzoic acid, 4,4-bis (4-hydroxyphenyl)-valeric acid, tert-butylhydroquinone, caffeine, trans-cinnamic acid, 2,6-di-tert-butyl-4-methylphenol, 2,7-dihydroxynaphthalene, 4,5-dihydroxy-2,7-naphthalenedisulfonic acid, 4,5-dihydroxy-2,7-naphthalenedisulfonic acid disodium salt, 6,7-dihydroxy-2-naphthalenesulfonic acid sodium salt hemihydrate, dimethylglyoxime, diphenylamine, 4-diazodiphenylamine sulfate, diazoaminobenzene, dinitronaphthalene, 1,8-dinitronaphthalene, 2,4-dinitrodiphenylamine, ethylenediaminetetraacetic acid, ethylenediaminetetraacetic acid iron (III) sodium salt hydrate, ethyl gallate, gallic acid monohydrate, gallic acid stearyl ester, gluconic acid, sodium salt, 97% (sodium gluconate), 8-gluconolactone, glycerophosphate (calcium salt), 2-hydroxycinnamic acid, 4-hydroxycoumarin, 4-hydroxycoumarin, 2-hydroxy-4-methoxybenzophenone, 7-hydroxy-4-methyl coumarin, 2-hydroxy-1,4-naphthalene, hydroquinonesulfonic acid potassium salt, lauryl gallate, DL-malic acid, mandelic acid, methylhydroquinone, methyl 3,4,5-trihydroxybenzoate, 5-nitroguaiacol (=3-hydroxy-4-methoxynitrobenzene), octadecylamine, 1,10 phenanthroline, phenothiazine, phenylboronic acid, N-phenyl-2-naphthylamine, 4-phenylphenol, phytic acid 50 wt % solution in water, poly (ethylene glycol) dimethyl ether Mn-500, propyl gallate, pyrogallic acid, salicylic acid, salicylamide, salicylaldoxime, tetrabutyl ammonium hydrogen sulfate, tetrabutylphosphonium bromide, tannoform, tetra-n-hexylammoinium bromide, tetrahexylammonium bromide, p-toluenesulfonic acid monohydrate, trichloroacetamide, trimethylhydroquinone, 2,3,4-trihydroxybenzophenone, trichloromethylphenyl carbinyl acetate, ascorbic acid, benzoin oxime, benzophenone hydrazone, 1,4-benzoquinonedioxime, 2-2(2H-benzotriazol-2-yl)-4,6-bis(1-methyl-1-phenylethyl)phenol, 4,4-bis(4-hydroxyphenyl)-valeric acid, chloranilic acid, 2-chloro-phenothiazine, 2,4-dihydroxybenzophenone, 2,3-dihydroxy naphthalene, 2,7-dihydroxynaphthalene, dimethylglyoxime, diphenylglyoxime, 2-2'-dipyridyl, 4,4'-dipyridyl, gallic acid isoamyl ester, gallic acid monohydrate, gallic acid n-octyl ester, glyoxal trimeric dihydrate, 4-hydroxycoumarin, methyl-3,4,5-trihydroxybenzoate, 1-nitroso-2-naphthol, 4-nitrosophenol, phenothiazine, propyl gallate, pyrogallic acid, resorcinol, rutin hydrate, salicylaldoxime, tannoform, 2,2',4,4'-tetrahydroxybenzophenone, 2,3,4-trihydroxybenzophenone, 4-tert-amylphenol, benzamide, benzilic acid, benzoic acid, benzyl sulfoxide, 4-(benzyloxy) phenol, 2-2'-biphenol 99%, 4-4'-biphenol 97%, 4-4'-bipyridyl, bisphenol A, tert-butylhydroquinone, cinnamyl alcohol, citric acid, 2,6-di-tert-butyl-4-methylphenol, dibutyltin bis (acetylacetonate), diethanolamine, 2,4-dihydroxy-benzophenone, dimethyl carbonate, N—N-dimethylethanolamine, glyoxal trimeric dihydrate, L-lactic acid, resorcinal, rutin hydrate, tetrabutylammonium bromide, tetrabutylammonium iodide, tetraethylammonium iodide, 2,2'-4,4'-tetrahydroxybenzophenone, fast orange base GC, benzilic acid, 2-2'-biphenol, 4-phenylphenol, salicylic acid, tetrabutylammonium hydrogen sulfate and tetrabutylphosphonium bromide.

The following is a list of examples of inorganic compounds tested as MP: ammonium acetate, ammonium bromide, ammonium carbamate, ammonium carbonate, ammonium chloride, ammonium dihydrogen phosphate, ammonium ferrocyanide (II) hydrate, ammonium iron (III) citrate, ammonium iron (III) oxylate hydrate, ammonium iron (III) sulfate dodecahydrate, ammonium iron (III) sulfate hexahydrate, ammonium sulfate, ammonium sulfite monohydrate, ammonium thiocyanate, ammonium thiosulfate, alumina, aluminum acetylacetonate, aluminum ammonium sulfate dodecahydrate, aluminum chloride hexahydrate, aluminum hydroxide, aluminum nitrate nonahydrate, aluminum sulfate hexadecahydrate, aluminum sulfate octadecahydrate, benzeneboronic acid, borane-tert-butylamine, borane dimethylamine, boric acid, boric acid tri-n-butyl ester, calcium acetate monohydrate, calcium acetyl acetonate hydrate, calcium bromide anhydrous, calcium bromide monohydrate, calcium chloride, calcium ferrocyanide, calcium hydroxide, calcium orthophosphate, calcium sulfide, copper, copper (II) acetate monohydrate, copper (II) acetylacetonate hydrate, copper (II) bromide, copper (I) chloride, copper (II) chloride hydrate, copper pyrophosphate, copper (II) sulfate pentahydrate, copper (I) thiocyanate, cupric benzoate, lithium acetylacetonate, lithium tetra-borate, lithium chloride, lithium formate monohydrate, lithium hydroxide monohydrate, ferric acetylacetonate, iron (II) bromide, iron (II) chloride tetrahydrate, iron (III) chloride hexahydrate, ferric ferrocyanide, ferrocene, p-gluconic acid iron (II) salt dihydrate, ferric salicylate, iron (II) sulfate heptahydrate, iron (III) sulfate pentahydrate, magnesium acetate tetrahydrate, magnesium chloride hexahydrate, magnesium oxide, magnesium sulfate heptahydrate, nickel, nickel (II) bromide, nickel (II) chloride, nickel sulfate, potassium acetate, potassium benzoate, potassium bromide, potassium carbonate, potassium chloride, potassium ferrocyanide (II) trihydrate, potassium ferricyanide, potassium formate, potassium iodide, potassium nitrate, potassium phosphate, dibasic trihydrate, tripotassium phosphate, potassium pyrophosphate, potassium sodium tartrate tetrahydrate, sodium acetate, sodium acetylacetonate, sodium bromide, sodium carbonate, sodium chloride, sodium cyanate, sodium dihydrogen phosphate, sodium diethyldithiocarbamate trihydrate, sodium fluoroborate, sodium hexametaphosphate, sodium iodide, sodium metasilicate, sodium nitrate, sodium nitrite, sodium oxalate, sodium thiosulfate pentahydrate, sodium phosphate dibasic, sodium sulfate anhydrous, sodium sulfite anhydrous, sodium tetraborate, sodium thiocyanate, sodium trimetaphosphate, sodium tripolyphosphate, tin (II) bromide, tin (II) 2-ethylhexanoate, zinc acetate dihydrate, zinc acetylacetonate hydrate, zinc bromide, zinc chloride, zinc iodide, zinc sulfate heptahydrate, zinc sulfide, ammonium bromide, ammonium chloride, ammonium thiocyanate, potassium iodide, potassium carbonate, sodium iodide and sodium thiocyanate.

The following is a list of examples of subliming compounds tested as accelerators: Butyramide, (±)-camphor, 2,3-dihydroxy naphthalene, (±)-isoborneol, (−)-menthol, (±)-menthol, naphthalene, 1,10 phenanthroline, (−)-β-pinene, propyl gallate, 8-quinolinol, salicylaldoxime and 2,3,4 trihydroxybenzophenone.

The following is a list of examples of polymers tested as matrix for a top indicator layer of the device shown in FIG. 8: polyvinylbutyral, cellulose acetate butyrate, chlorinated rubber, polyepichlorohydrin, polyisobutylmethacrylate and polyvinylacetate.

The following is a list of examples of organic compounds tested as a plasticizer for S85 PSA as a SP: benzyl ether, tris (2-butoxyethyl) phosphate, bis (2-ethylhexyl) adipate, bis (2-ethylhexyl) sebacate, diethyl oxalate, diethyl phthalate, dimethyl phthalate, dioctyl phthalate and Dover Chemical's PhosBooster 681, Halstab plastistab 2808.

The following is a list of examples of PSA and hot melt adhesives tested as organic compounds tested as SP: Actega RAQUE-BOND 5565 RAWA006500 and RAQUA-BOND P22AQDF RAWA00501 (ACTEGA WIT, Lincolnton, N.C.), 58510 and AT-20 (Avery Dennison Corporation, Glendale, Calif.), Covinax 210-05 (Franklin International, Columbus, Ohio), Rovene 6001 and Rovene 9423 (Mallard Creek Polymers Inc, Charlotte, N.C.), EPOTUF 91-263 and TYLAC #68221-00 (Reichhold Inc, Research Triangle Park, N.C.), AS-203 (Adhesives Research, Glen Rock, Pa.), Lutanol, (BASF, Ludwigshafen, Germany), hot melt adhesive HRJ-12531, Scotchgrip 4693 & 9731 and HD 2058-01 polyester, double coated acrylic tape (3M, St. Paul, Minn.), 23-FEP, tape with silicon adhesive (CS Hyde Company, Lake Villa, Ill.), polyurethane hot melt adhesive on polyester (Can-Do National Tape, Nashville, Tenn.), custom made acrylic hot melt adhesive on polyester film #847321-001-2 (Transilwrap Co Inc, Franklin Park, Ill.), acrylic hot melt by DRYTAC Corp, Richmond, Va., acrylic hot melt adhesive (Fastel Adhesives & Substrate Products, San Clemente, Calif.).

The shelf-life of un-activated devices will be sufficiently long there is nothing in this system that can influence shelf-life. Even if a slight loss of activator/MP occurs over years of storage at high temperatures, it will be very little and will barely affect the kinetics, rate of movement of the boundary "t" and activation energy Ea, unless some highly volatile or environmentally sensitive activator/MP or SP/indicators are used. In case of TTI, activated devices will require freezing. Shelf-life of activated devices will depend upon the natures of activator/MP, indicator and PSA/SP.

The service life (e.g., time required for the boundary to travel a certain distance or a color change) and the activation energy of the current indicating devices can be varied by one or more of the following major parameters:

The service life of the devices can be changed by parameters such as thickness of SP, quantity of MP, size and shape of the device, thickness of a permeable barrier layer if used, concentration of an activator and co-activator, concentration of an indicator and co-indicator, concentration of accelerator, concentration of a precursor, and concentration of an additive.

The service life and activation energy of the devices can be change by parameters such as nature of a SP, nature of MP, nature of an activator, nature of an indicator, nature of accelerator, nature of a permeable layer, and nature of an additive.

The indicating devices based on lateral diffusion of vapor through a non-porous SP are unique and novel. Solid MP can be used. Quantities of MP and SP required are small. MP does not wet SP. SP of the current devices has no pores. As liquid is not used, the current devices don't require a container type reservoir. The system is much simpler. Boundary is sharper than known art devices. The thickness of the SP layer is very thin. A large number of polymeric materials, especially adhesives including pressure sensitive or heat activated adhesives can be used. The initial movement of the boundary linear with time, which is one of the most desired properties.

In addition to advantages mentioned above, the indicating devices disclosed herein offer many advantages including:

SP is non-porous solid or semi-solid. A typical SP is an adhesive, PSA or hot melt and hence a self-laminating device. It is essentially a solid state device and if a liquid is used it is very little. They are easy to manufacture and significantly less expensive. By selecting proper ingredients, the devices can be made essentially unaffected by undesirable ambient conditions, such as humidity and UV light. The devices can be made by using commercially available printing and coating equipment. The service life of the device can be varied from hours to years. There is a very wide choice of materials which are commercially available to make the devices. The boundary of the devices remain sharp all the time.

The TTI devices of current invention are the simplest, thinnest and smallest solid state moving boundary TTI. The devices are sufficiently small (a few mm to a few cm) to apply on caps of any small perishable, such as vaccine vials and syringes. A solid or open circle with sharp boarder can be created. If required, diffuse edge circles can also be created. Even though solid black color is preferred, essentially any color circles (yellow, red, blue to black) can be created. It has features of color changing and moving boundary. There are many non-toxic MP/activators, indicators and SP to choose from to make the devices. Threshold TTI can be made by selecting MP or additive for MP and/or SP having proper melting point. The devices are ideal for small perishables such as vaccines. It will be easier to make reproducible devices. Long strip (~5 cm) moving boundary TTI can be created by sealing the edges. Even though TTI device is small, one can still prepare combination indicator with freeze and/or temperature indicators. It is easy to modify the device by printing circles, masks, barcodes, appearing or disappearing messages.

The devices are highly precise and easy to read and will provide more than required precision. There is no confusion of color matching, the devices are essentially self-reading. They do not require color reference bars. The devices require very little or no training required to read.

Self-reading (1, 2, 3 . . . etc) devices can be made. Two messages, Go/No-Go type devices (with induction period) can also be made. Devices with induction period can be made by masking (it can be used to replace use-by/sell-by dates due to the induction period). The induction period of 90+% with uncertainty of 10% is possible. It has advantages of self-reading, moving boundary and color changes with disadvantages of none. Machine readable (including 2D barcode) devices can also be made.

The devices are least effected by concentration or amount of MP (e.g., ~5 folds), other devices are highly concentration dependent. The devices are least effected by variation in thickness or uneven thickness of SP (e.g., ~5 folds) layer while other devices are highly thickness dependent. They are self-shape-correcting for minor errors in shape or thickness of MP. They have very wide tolerance zones. They are highly reliable and reproducible devices and can be manufactured with least efforts as they are almost insensitive to many manufacturing variables. They are not affected by gravity and by selecting proper materials can be made insensitive to undesirable ambient parameters such as humidity and UV/sunlight. They are mainly sensitive to time and temperature only, a true TTI. They are essentially mistake proof, fail proof, fool proof. They have potentials of being widely accepted by the perishable industry. The validation and acceptance of the devices will be easier/faster. Essentially anyone label manufacturer can make good quality devices.

The devices can be made tamper resistant by using a hot melt adhesive as SP. TTEye with hot melt adhesive works essentially as good as that with PSA (only slightly slower). Using tamper evident films as a substrate, one can make the devices tamper evident (i.e., if peeled from the container, it will be evident). Breakable plastic films can be used as substrates to make tamper evident devices.

The devices don't require color printing and hence fewer printing stations will be required to manufacture the devices. Basically only one coating (for MP) on a SP tape and one printing station (black ink) is required for manufacturing. Solvent based, water based, UV curing inks can be used. Ink jet and digital printing can be used to provide serial number for each device (2D dot barcode). The devices can be activated online or pre-activated and shipped frozen.

The devices will not require cold storage as two tapes can be stored for years at room temperature, a huge saving in energy, space and shipping. The rolls can be shipped at room temperature around the world by (surface shipping). Print the top surface (circles, mask, barcode etc), laminate and ship when order is received.

These devices will be significantly less expensive in material, equipment, space, labor and overhead. They would be essentially, no unacceptable batches due to human errors. The devices need simple basic equipment, no heat sealing of edge of moving boundary or special equipment required. They do not require multilayer coating and cold storage or shipping and can be manufactured at a faster rate. They will be significantly less expensive than the other devices of similar nature.

The above and those disclosed herein are some common examples of possible variations, alterations, modifications and options of the materials, devices and processes. By permutation—combination, it is possible to have a very large number of variations, modifications and options for the devices and processes, e.g., by changing properties of components, position of a layer, multiplicity of a layer, adding an extra layer, changing nature of additives, activators, indicator, MP and SP, adding image/message, by varying the size and shape of a layer or the device, varying nature of the materials, and many other parameters including those mentioned in this application.

The current inventions can be used to improve performance of a large number of the known art indicating devices (mentioned herein or not) by many different ways. Inventions disclosed herein can be combined with known art compositions, processes and devices to make best of the both technologies.

The following examples are illustrative of carrying out the claimed inventions but should not be construed as being limitations on the scope or spirit of the instant inventions.

EXAMPLES

Example 1: Control and Comparison Experiments of Known Art and Current Invention with a Fluid MP and a Solid MP In order to obtain a solid MP on SP, 0.1 g of methyl yellow was dissolved in 0.25 g of THF, a volatile solvent. In order to get liquid or semi-solid MP, 0.1 g of methyl yellow was dissolved in 0.25 g of benzyl ether, a non-volatile solvent. A drop each of these two solutions was placed on three SP (i) cellulose/copying paper as a porous SP, (ii) a polyester film coated 50 microns of S85 PSA without any accelerator and (iii) a polyester film coated with 50 microns of S85 PSA containing 50% bis(2-ethylhexyl sebacate) as shown in FIGS. 13($a1$), 13($a2$) and 13($a3$). S85 is a pressure sensitive solvent based acrylic adhesive supplied by Avery Dennison, Painesville, Ohio. THF being highly volatile solvent (boiling point 66° C.), it evaporated within minutes at room temperature and spots of dry powder of the dye ware obtained. The spots of benzyl ether remained wet as it is a high boiling (boiling point 298° C.) with little volatility. The above samples were mounted on a glass plates and place in a special heating block at different temperatures.

FIG. 13 shows growth of methyl yellow spots in THF and in benzyl either as an accelerator, on three different SP: (i) S85 PSA as a non-porous SP, FIGS. 13($a1$), 13($b1$) and 13($c1$), (ii) S85 PSA plasticized with bis(2-ethylhexyl sebacate) as a non-porous SP, FIGS. 13($a2$), 13($b2$) and 13($c2$) and (iii) a copying paper as a porous SP, FIGS. 13($a3$), 13($b3$) and 13($c3$).

The spots were smaller on coatings S85 PSA and plasticized S85 as shown in FIGS. 13($a1$) and 13($a2$) respectively. Almost as soon as a drop of THF solution methyl yellow was placed on paper, it grew to the size shown in FIG. 13($a3$). THF evaporated and a dry coating of methyl yellow was obtained on the paper. That spot did not grow at all even after a week as shown in FIG. 13($c3$). The spot of methyl yellow in benzyl ether on paper grew slowly within a minute to the size shown in FIG. 13($a3$) and grew to the size shown in FIG. 13($b3$) after 11 hrs at 60° C. and followed by very little growth as shown in FIG. 13($c3$) even after 4 days at 60° C. Based on known art and as expected, the spot of methyl yellow in benzyl ether grew rapidly in the beginning and then rapidly slowed down to essentially stopped growing. The spot of dry methyl yellow as shown in FIGS. 13($a3$), 13($b3$) and 13($c3$) did not grow on paper indicates that a fluid is essential for movement of the dye if the SP is porous.

The spot of methyl yellow without benzyl ether as accelerator grew only slightly on S85 as shown in FIG. 13($c1$). However, this spot continued to grow with time and temperature (not shown here) but that on the paper did not grow. The spot of methyl yellow in benzyl ether as accelerator grew on S85 as shown in FIG. 13($c1$).

The spot of methyl yellow without benzyl ether as accelerator grew faster on plasticized S85 than unplasticized S85 as shown in FIG. 13($c2$). This spot continued to grow with time and temperature at a faster rate than that on unplasticized S85. The spot of methyl yellow in benzyl ether as accelerator grew fastest on plasticized S85 as shown in FIG. 13($c2$). This spot continued to grow with time and temperature and grew largest and still most of solid dye was left in the center.

Similar results were obtained with (i) a large number of other dyes, such as Sudan II and oil blue N, (ii) acids and bases as activators and universal indicator as an indicator and (iii) chelates as activators and a metal ion, especially ferric ion as an indicator.

The above results clear differentiate known art from current invention. The current invention of using solid MP does not work with porous SP to use as TTI. Dry power of an indicator or MP does not migrate on porous SP while it does on non-porous SP.

The above results also show that by adding an accelerator (benzyl ether and bis(2-ethylhexyl sebacate)) the movement of the boundary can be accelerated.

In another experiment, a paper was wetted with benzyl ether and allowed to drip for two hours to make a porous SP non-porous (pores filled). A spot of methyl yellow was created with its dry (red colored) powder. After about one hour a yellow boundary was created and the boundary moved with time and temperature.

Other devices were made by spreading fine powders with solid MP on a PSA layer of SP.

Example 2: A PSA as a SP

A large number of dyes were dissolved in proper solvents and spotted on 50 micron thick layer of S85 on 40 micron polyester film, let the solvents evaporate, laminated with another 40 micron polyester film and stored in an over at about 80° C. Colored spots of many dyes grew at different speeds depending upon the nature of the dyes. Ionic dyes either did not grow or grew very slowly. The spots of dyes with lower molecular weight, such as methyl yellow usually grew rapidly. Dyes with moderate molecular weight, such as Sudan II grew slowly while dyes with very high molecular weight grew very slowly or did not grow.

Figure 14:
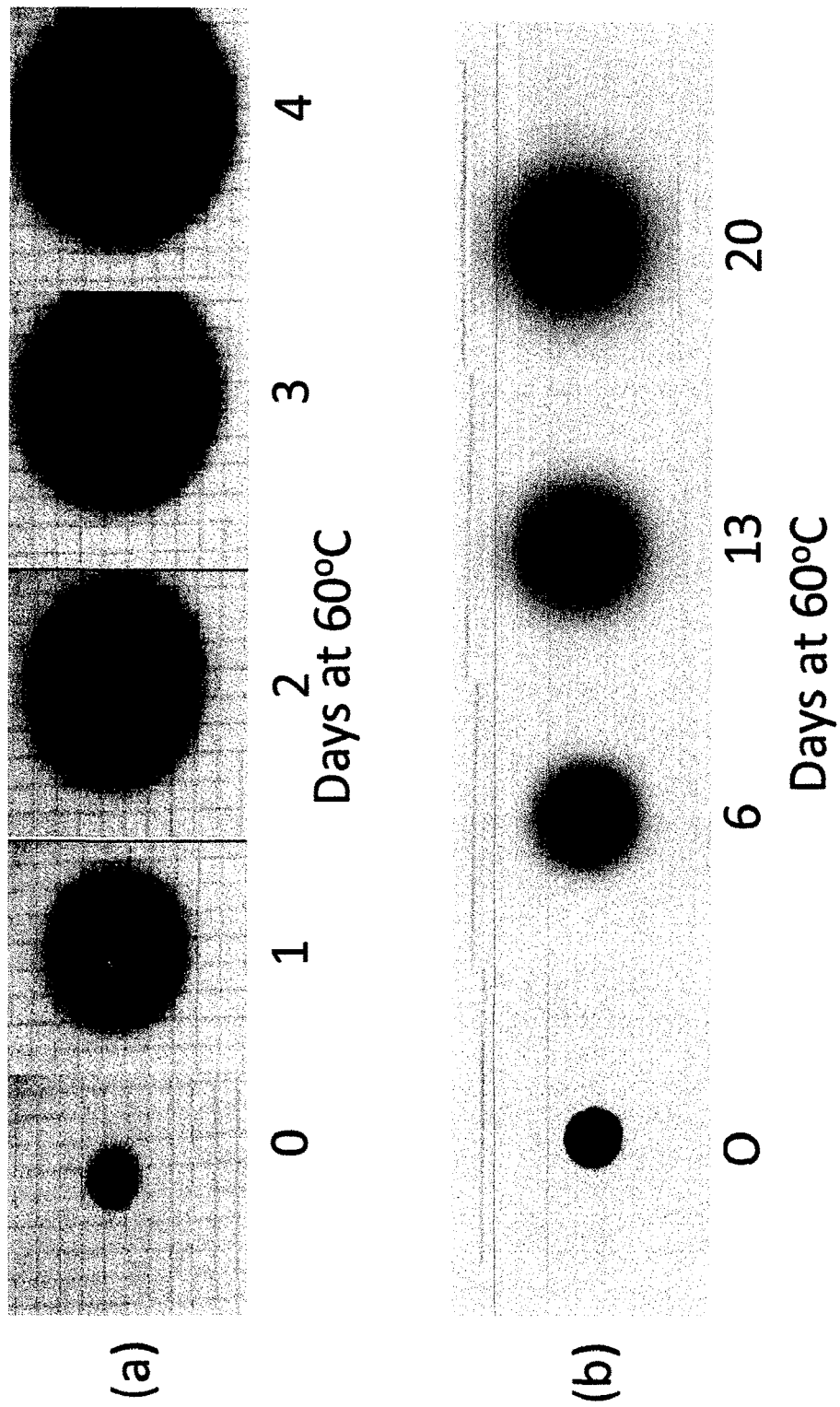
FIG. 14 shows different stages of diffusion of (a) methyl yellow in a 50 micron thick layer of plasticized S85 PSA and (b) Sudan II with time at 60° C. in a 25 micron thick layer of an acrylic hot melt adhesive.

In order to study effect of time on migration of the boundary, 0.1 g methyl yellow was dissolved in 0.25 g of THF. Drops of the solution were placed on a 40 micron polyester film coated with 50 micron thick layer of S85. THF evaporated within minutes at room temperature and spots of dry powder of the dye ware obtained. The coating was laminated with a clear polyester film. The samples were annealed at different temperatures. FIG. 14($a$) shows different stages of growth of the dye with time at 60° C. The spots of dye grew rapidly at higher temperatures and slower at lower temperatures.

Example 3: Hot Melt Adhesive as a SP

We discovered that it is not necessary to have a PSA as SP for the devices of this invention. A number of hot melt, non-tacky polyurethane and acrylic hot melt adhesives coated on polyester films were obtained from different distributors and manufacturers. Dry spots of methyl yellow and Sudan II in THF were prepared on the hot melt adhesive and laminated either with a clear polyester film or with the same hot melt adhesive film using a heat laminator between 110° C. and 150° C. depending upon the nature of the hot melt adhesive. The samples were annealed at different temperatures. FIG. 14(b) shows different stages of growth of the Sudan II on a 25 micron thick layer of an acrylic hot melt adhesive (a polyester film coated with an acrylic hot melt adhesive supplied by Transilwrap, Bethlehem, Pa.) with time at 60° C. When the SP is an acrylic hot melt adhesive the growth of the spot was lower than that of PSA.

In another experiment, a 25 micron polyethylene was spotted with methyl yellow dye and heat laminated between two polyester film. The spot grew with time and temperature.

Example 4: Effect of Temperature

Drops of the solution of methyl yellow were placed on a 40 micron polyester film coated with 50 micron thick layer of S85 PSA. THF evaporated within minutes at room temperature and spots of dry powder of the dye ware obtained. The coating was laminated with a clear polyester film. The samples were annealed at different temperatures. FIG. 15 shows different stages of growth of a spot after 11 days at different temperatures (° C.). As can be from the FIG. 15, higher the temperature faster the growth of the spot. The spot initially grew linearly as shown in FIG. 16.

Example 5: Effect of Nature of SP

Drops of the solution of methyl yellow in THF were placed on layers of different PSA and hot melt on polyester. After drying, the films were laminated with a clear polyester film and the samples were annealed at temperatures for different time. FIG. 17 shows effect of nature of pressure sensitive adhesive as SP on growth of a spot of Sudan II at 80° C. The growth of Epotuf (an epoxy PSA) was slowest and that of AT20 (an acrylic PSA) was the fastest. The growth of the spot of the spots depends upon many other factors, such as nature of the SP, MP, indicator, activator, additives etc.

Example 6: Activator-Indicator Pair

In 5 g of S85 solution was added 0.25 ml of universal indicator. Universal indicator was prepared by dissolving 0.50 g phenolphthalein, 0.30 bromothymol blue, 0.03 g thymol blue sodium salt, 0.06 g methyl red in 20 g THF. The solution of S85 was coated on a polyester film and dried in an oven to obtain 50 micron thick dry coating. The coating was faint orange color. Drops of 50% solution of diaminododecane (mp~76° C.) in THF were placed on the S85-universal indicator coating. THF was allowed evaporate. The spot turned from colorless to blue. The samples were than laminated either with S85-universal indicator or with a clear polyester film. FIG. 18 shows different stages of growth of a spot of diaminododecane as an activator and a universal indicator as an indicator after 18 hours at different temperatures (° C.). As can be from the FIG. 18 when MP is not a coloring material, colored boundary can be created by using an activator-indicator pair which produces color. The spot did not grow below about 60° C. while it grew rapidly with time and temperature at temperatures above 70° C. The results indicate that one create a temperature-activable threshold time-temperature indicator which gets activated once a pre-determined temperature or temperature range is reached.

Though we used an amine as an activator, one can use an acid as well. We also made a number of devices similar to that shown in this example, using a number of chelates as activator and metal salts, e.g., ferric acetate and organometallic compounds, e.g., potassium ferricyanide as indicator.

Example 7: Strip Moving Boundary Indicator

A 50% solution of nitrosonaphthol in THF was coated in form a thin strip at the end of film coated S85 containing potassium ferricyanide. After letting the solvent evaporate, the film was laminated with a clear polyester film and heat sealed all around between two 50 micron polyester films. The device was placed in an oven at 80° C. A green boundary was created and moved at the other end with time as shown in FIG. 19. Any other chelate can be used as a MP activator and any other metal salt or metal complex can be used as an indicator.

Example 8: Threshold, Thaw or Temperature-Activable Time-Temperature Indicator

A solution of 5 g of S85 (40% solid acrylic polymer) and 2 g benzyl ether (melting point 2-3° C.) was coated on a polyester film and dried to get 50 micron thick coating. The spots of methyl yellow (0.1 g methyl yellow was dissolved in 0.25 g of THF) were created on S85-benzyl ether coating, dried and laminated with a clear polyester film. Some samples placed in a freezer (~10° C.) while the others were left at room temperature and refrigerator (~7° C.). The spots of the room temperature samples grew by a millimeter within a day while those in freezer did not grow at all even after a few months. The results indicates this type of system can be used to make thaw or threshold time-temperature indicators.

Example 9: Effect of Polymers and Permeability of Polymers

The devices of FIG. 5 were created by using different iron compounds such as iron stearate as the bottom indicator layer made of different polymers (for example, polyvinyl butyrol, cellulose acetate butyrate, chlorinated rubber, polyepichlorohydrin, polyisobutylmethacrylate and polyvinylacetate) and nitrosonaphthol and many other chelates as activator and a layer of S85 as SP. Polyvinyl acetate displayed higher activation energy but the spot grew at slower speed at room temperature but while polyvinyl butyrol displayed lower activation energy but the spot grew at a faster speed at room temperature.

Example 10: Self-Shape-Correcting System

During spotting different MP on SP, once in a while the MP spots were not circular shaped as shown in FIG. 20 (a0 and b0) as two examples. However as the spots grew with time and temperature, every irregular shaped spots became nearly perfect circle as shown in FIG. 20 (a3 and b3).

Minor defects in thickness and shape of MP is corrected because MP diffuses in all directions to fill the gaps/defects in shape and makes the circular shape. One of the unique features of this system is its ability to self-correct minor shape of MP, quantity of MP and thickness defects/imperfections in SP layer. Imperfection will be automatically corrected as the boundary advances, especially when it supposed to show expiration of service life. The imperfections will be not be noticed if MP has a mask.

Example 11: Effect of Concentration/Amount of Mobile Phase

Three different concentrations (15%, 30% and 60%) of methyl yellow and Sudan II were prepared in hot THF and spotted polyester film coated S85 adhesive. The solvent was allowed to evaporate and then laminated with a polyester film. The samples were annealed at 60° C. Table 2 shows sizes of the spots after 12 and 48 hours at 60° C.

TABLE 2

Area (square mm) of spot of different concentrations of methyl yellow and Sudan II at 60° C.

|  | Methyl Yellow | | | Sudan II | | |
| --- | --- | --- | --- | --- | --- | --- |
|  | 60% | 30% | 15% | 60% | 30% | 15% |
| Initial | 7 | 7 | 7 | 3 | 3 | 3 |
| After 12 hours | 20 | 20 | 17 | 7 | 7 | 7 |
| After 48 hours | 28 | 28 | 24 | 16 | 15 | 15 |

As can be seen from the Table 2, even if we varied the concentration/amount of MP four times, the growth of the spots of MP grow almost independent of concentration or the amount of the MP.

Example 12: Effect of Concentration of a Plasticizer/Diluent (Benzyl Ether) in S85 PSA as SP In 6 g of S85 (40% solution) were added varied amount of benzyl ether and coated to get 2 mil dry thickness on a polyester film. The coating were spotted with methyl yellow (0.1 g in 0.25 g of THF), dried and laminated with a polyester film. The samples were annealed for different times at different temperatures. Table 3 show the size of the spot after one day at different temperatures.

TABLE 3

Area (square mm) of spots of methyl yellow having different concentrations of a plasticizer/diluent (benzyl ether)

| Amount (g) of benzyl ether | Initial area | 25° C. | 45° C. | 55° C. | 80° C. |
| --- | --- | --- | --- | --- | --- |
| 0.25 | 8 | 17 | 33 | 28 | 43 |
| 0.50 | 8 | 24 | 36 | 36 | 52 |
| 1.00 | 8 | 36 | 64 | 64 | 104 |
| 1.50 | 8 | 44 | 80 | 113 | 197 |

As can be seen from table 3, as the concentration of plasticizer increases, the rate of growth of the spot increases.

Example 13: Effect of Sunlight 0.1 g of three dyes listed in Table 4 were dissolved in 0.25 g of THF and spotted on 2 mil S85 PSA and laminated with a polyester film. One set of samples were placed in a metallized plastic beg to protect from sunlight while the other set placed over it and left in the sunlight for 10 days. The size of the spots inside the metallized beg (in dark) and under sunlight are shown in Table 4.

TABLE 4

Area (square mm) of spots of three dyes under the sunlight and in dark after 10 days.

| Dye | Starting | Under sunlight | In dark |
| --- | --- | --- | --- |
| Methyl Yellow | 10 | 38 | 38 |
| Oil Blue N | 5 | 13 | 13 |
| Sudan II | 7 | 20 | 20 |

As can be seen from table 4, by selecting proper MP and SP, effect of sunlight can be eliminated.

Example 14: Effect of Humidity 0.1 g of three dyes listed in Table 5 were dissolved in 0.25 g of THF and spotted on 2 mil S85 PSA and that plasticized with bis(ethyl hexyl sebacate). One set of the samples were laminated with a polyester film and exposed to 100% relative humidity at 35° C. while the other set was placed in a bag to protect from humidity. Table 5 shows growth of the spots with and without humidity.

TABLE 5

Area (square mm) of spots of three dyes on S85 PSA with and without a plasticizer after 3 days at 35° C. outside (no humidity) and inside a camber at 100% relative humidity.

|  |  | Without plasticizer | | With plasticizer | |
| --- | --- | --- | --- | --- | --- |
| Dye | Starting | Inside | Outside | Inside | Outside |
| Methyl Yellow | 2 | 7 | 7 | 38 | 38 |
| Oil Blue N | 1 | 3 | 3 | 13 | 13 |
| Sudan II | 2 | 3 | 3 | 20 | 20 |

As can be seen from table 5, by selecting proper MP and SP, effect of humidity can be eliminated.

Example 15: Effect of Thickness of SP

S85 PSA solution was coated on a polyester film to obtain dry thicknesses of 20, 50 and 90 microns. The coatings were spotted with same amount of methyl yellow solution, dried and laminated with another polyester film. The samples were annealed at room temperature and 60° C. Irrespective of thickness of the SP layer, the size of the spots of methyl yellow was 28 mm$^2$ for the samples stored at room temperature and 62 mm$^2$ for samples stored at 50° C. after two days. The results indicate that thickness of SP layer has very little effect on movement of the boundary.

The invention claimed is:

1. An indicating device based on lateral diffusion of a mobile phase through a layer of a non-porous stationary phase comprised of a mobile phase layer; and a non-porous, non-adsorbing or non-absorbing stationary phase layer;
   wherein the mobile phase laterally diffuses through the stationary phase layer and creates a noticeable or measurable boundary;
   wherein the stationary phase layer and the mobile phase layer are sandwiched between two substrates;

wherein the mobile phase or the stationary phase are either coated on the same or different substrate; and wherein the lateral diffusion is in a plane parallel to the plane of the non-porous stationary phase.

2. The indicating device of claim 1 wherein the mobile phase is a solid, liquid or mixture thereof.

3. The indicating device of claim 1 wherein the mobile phase layer is substantially smaller in area than the stationary phase layer.

4. The indicating device of claim 1 wherein the mobile phase is a coloring material.

5. The indicating device of claim 1 capable of producing a noticeable or measurable change, including a change in conductivity, resistivity, phase, state or optical such as color, fluorescence, clarity and opacity.

6. The indicating device of claim 5 wherein the coloring material is a dye or pigment.

7. The indicating device of claim 1 wherein the mobile phase is a part of an activator-indicator pair which are capable of reacting to produce a coloring material or noticeable change.

8. The indicating device of claim 1 where the mobile phase is a part of a pair of (i) an acid, base, or salt and a pH dye, or (ii) metal ion or metal complex and a chelate.

9. The indicating device of claim 1 wherein the mobile phase layer is comprised of a mobile phase a coloring material, and either an activator or an indicator, and optionally comprises a binder and/or a controller.

10. The indicating device of claim 1 wherein the stationary phase is a pressure sensitive or hot melt adhesive polymeric material permeable to the mobile phase selected from the group of a polymer or copolymer of an acrylic, ether, imide, imine, urethane, cyanoacrylate, olefin, vinyl, styrene, silicone or epoxy.

11. The indicating device of claim 1 which further comprises a controller which is an adjuvant additive which can control, adjust, or modify the properties and performance including rate of reaction, rate of movement of the mobile phase, rate of movement of the boundary and activation energy of the indicating device.

12. The indicating device of claim 11 wherein the controller is a solvent, volatile or subliming solid, oligomer, plasticizer, viscosity modifier, crosslinking agent, retarder or accelerator.

13. The indicating device of claim 1 wherein a marker, scale, mask or message is printed on any surface of a layer of the indicating device.

14. The indicating device of claim 13 wherein the scale is in form of open or solid circles, lines, barcodes, or numbers.

15. The indicating device of claim 13 wherein the message is a word or symbol, two messages which do not start to become observable at the same time, indicates a condition or treatment, one message indicates un-doneness, freshness, freshness, usability, acceptability of the item and a second message alone or in combination with the first indicates doneness, spoilage, unusability and unacceptability of the item after a treatment or where the first message indicated non-sterility, non-usability, unacceptability of the item and the second message alone or in combination with the first indicates doneness, sterility, usability and acceptability of the item after a treatment.

16. The indicating device of claim 1 wherein the service life, rate of reaction, rate of permeation, rate of movement of boundary, and activation energy of the indicating devices are varied by varying parameters selected from the group of: nature and thickness of a stationary phase, nature and concentration or amount of the mobile phase or co-mobile phase, nature and concentration of an activator, nature and concentration of an indicator, nature and thickness of a layer of the device in a permeable layer and the nature and concentration of a controller.

17. The indicating device of claim 1 which comprises mobile phase tape composed of a mobile phase, an activator or an indicator, a binder and a controller on a substrate.

18. The indicating device of claim 1 comprising a stationary phase tape comprised of a stationary phase, an indicator or an activator, and a controller on a substrate.

19. The indicating device of claim 1 comprising (1) a mobile phase tape (2) a stationary phase tape which can be activated by applying one tape over the other so that the mobile phase comes in contact with the stationary phase.

20. The indicating device of claim 1 which further comprises an extra layer selected from permeable layer, non-permeable barrier layer, reactive layer, destroyable or degradable barrier layer, an expiration indicating layer, a tamper indicating layer, an activation indicating layer, a message or image creating layer, a separating layer, mask layer, a removable layer, a disappearing layer, an appearing layer, an activator layer, an indicator, a microencapsulated layer, a thermally printable layer, and a whole, partial or discontinuous layer, in form of a pattern, message or image.

21. A process of monitoring a change which comprises using an indicating device based on lateral diffusion of a mobile phase through a layer of a non-porous stationary phase to indicate a change in time, temperature, time-temperature, freeze, thaw, heating, cooling, humidity, doneness of food, microwave and sterilization including sterilization with steam, ethylene oxide, a peroxide, plasmas of a peroxide, formaldehyde and dry heat by monitoring a change in the indicating device wherein the lateral diffusion is in a plane parallel to the plane of the non-porous stationary phase.

* * * * *